Figure 1:
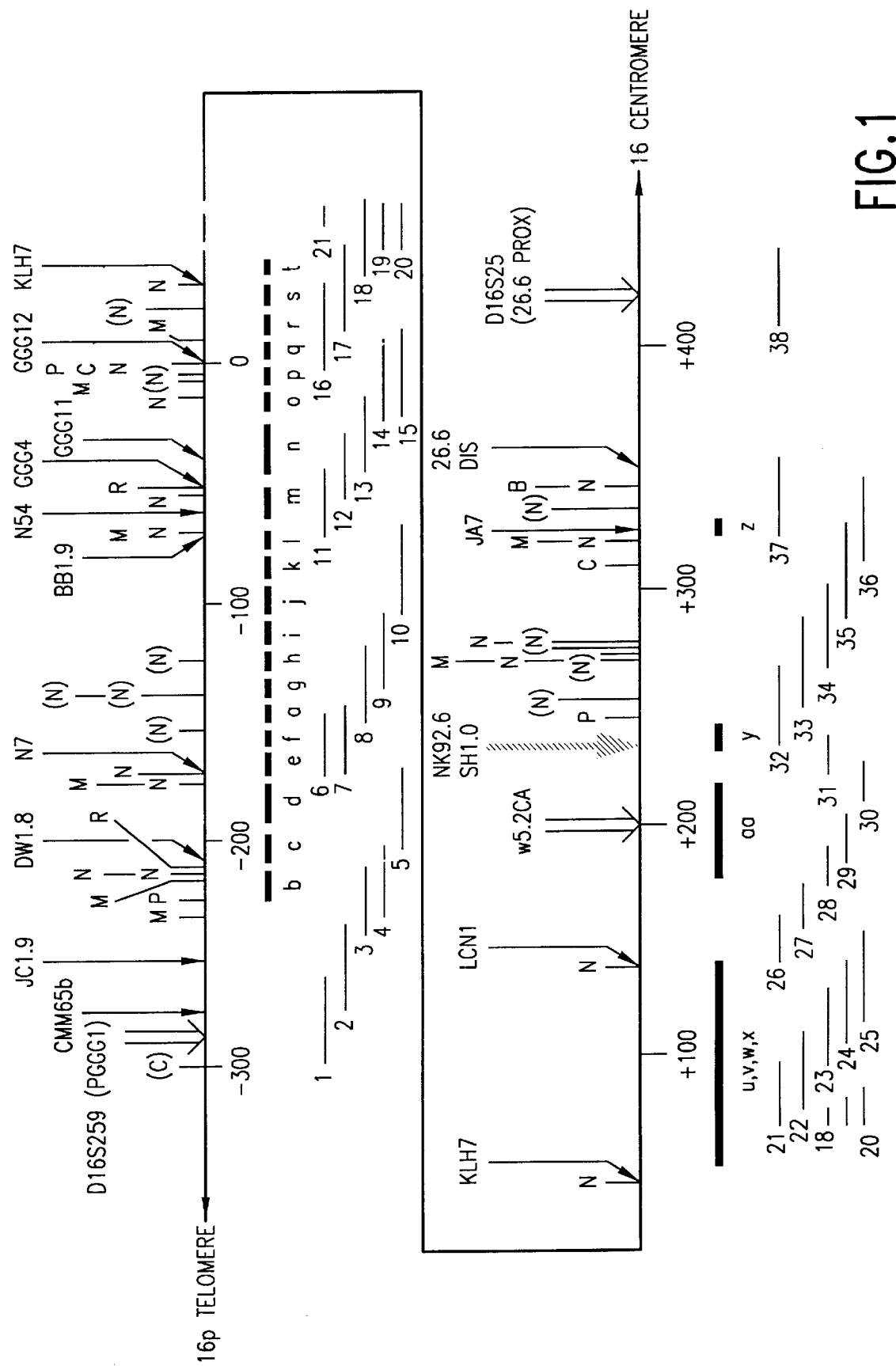

US005891628A

United States Patent [19]
Reeders et al.

[11] Patent Number: 5,891,628
[45] Date of Patent: Apr. 6, 1999

[54] IDENTIFICATION OF POLYCYSTIC KIDNEY DISEASE GENE, DIAGNOSTICS AND TREATMENT

[75] Inventors: Stephen Reeders, Newtonville; Michael Schneider, Boston; Maria Alexandra Glucksmann, Somerville, all of Mass.

[73] Assignees: Brigham and Women's Hospital, Boston; Millenium Pharmaceuticals, Cambridge, both of Mass.

[21] Appl. No.: 460,751

[22] Filed: Jun. 2, 1995

Related U.S. Application Data

[60] Division of Ser. No. 413,580, Mar. 30, 1995, which is a continuation-in-part of Ser. No. 253,524, Jun. 3, 1994, abandoned.

[51] Int. Cl.$^6$ .................................................. C12Q 1/68
[52] U.S. Cl. ............................... 435/6; 435/7.1; 435/7.9; 436/578; 530/387.1; 530/387.9; 530/389.1; 530/388.1
[58] Field of Search ................................ 530/387.1, 387.9, 530/389.1, 388.1; 436/518, 523–531; 435/6, 7.1, 7.9–7.95, 325, 331

[56] References Cited

U.S. PATENT DOCUMENTS 5,654,170  8/1997  Klinger et al. ......................... 435/69.1

OTHER PUBLICATIONS

Reeders, S. et al., 1989, "Mapping the Locus of Autosomal Dominant Polycystic Kidney Disease: Diagnostic Application", Clin. Chem. 35(7B):B13–B16.
Himmelbauer, H. et al., 1992, "Human–Mouse Homologies in the Region of the Polycystic Kidney Disease Gene (PKD1)", Genomics 13:35–38.
Wright, A. et al., 1993, "A Study of Genetic Linkage Heterogeneity in 35 Adult–Onset Polycystic Kidney Disease Families", Hum. Genet. 90:569–571.
Kimberling, W. et al., 1993, "Autosomal Dominant Polycystic Kidney Disease: Localization of the Second Gene to Chromosome 4q13–q23", Genomics 18:467–472.
Reeders, S. et al., 1985, "A Highly Polymorphic DNA Marker Linked to Adult Polycystic Kidney Disease on Chromosome 16", Nature 317:542–544.
Reeders, S. et al., 1988, "Regional Localization of the Autosomal Dominant Polycystic Kidney Disease Locus", Genomics 3:150–155.
Kaspareit–Rittinghausen, J., et al., 1989, "Hereditary Polycystic Kidney Disease Associated with Osteorenal Syndrome in Rats", Vet. Pathol. 26:195–201.
Breuning, M. et al., 1990, "Map of 16 Polymorphic Loci on the Short Arm of Chromosome 16 Close to the Polycystic Kidney Disease Gene (PKD1)", J. Med. Genet. 27:603–613.
Gabow, P., 1990, "Autosomal Dominant Polycystic Kidney Disease—More Than a Renal Disease", Am. J. Kidney Dis. 16:403–413.

Germino, G. et al., 1990, "Identification of a Locus Which Shows No Genetic Recombination with the Autosomal Dominant Polycystic Kidney Disease Gene on Chromosome 16", Am. J. Hum. Genet. 46:925–933.
Gillespie, G. et al., 1990, "Cosmid Walking and Chromosome Jumping in the Region of PKD1 Reveals a Locus Duplication and Three CpG Islands", Nucl. Acids Res. 18:7071–7075.
Wilson, P. et al., 1991, "Reversed Polarity of $Na^+-K^+$–ATPase: Mislocation to Apical Plasma Membranes in Polycystic Kidney Disease Epithelia", Am. J. Physiol. 260:F420–F430.
Germino, G. et al., 1992, "The Gene for Autosomal Dominant Polycystic Kidney Disease Lies in a 750–kb CpG–Rich Region", Genomics 13:144–151.
Reeders, S., 1992, "Multilocus Polycystic Disease", Nature Genetics 1:235–238.
Somlo, S. et al., 1992, "Fine Genetic Localization of the Gene for Autosomal Dominant Polycystic Kidney Disease (PKD1) with Respect to Physically Mapped Markers", Genomics 13:152–158.
The European Chromosome 16 Tuberous Sclerosis Consortium, 1993, "Identification and Characterization of the Tuberous Sclerosis Gene on Chromosome 16", Cell 75:1305–1315.
Carone, F. et al., 1994, "Biology of Polycystic Kidney Disease", Lab. Investigation 70:437–448.
The European Polycystic Kidney Disease Consortium, 1994, "The Polycystic Kidney Disease 1 Gene Encodes a 14 kb Transcript and Lies within a Duplicated Region on Chromosome 16", Cell 77:881–894. Errata published in Cell 78(4), (1994) and Cell 81(7), 1995.
Wunderle, V. et al., 1994, "Breakpoint Break for Consortium Studying Adult Polycystic Kidney Disease", Cell 77:785–786.
The American PKD1 Consortium, 1995, "Analysis of the Genomic Sequence for the Autosomal Dominant Polycystic Kidney Disease (PKD1) Gene Predicts the Presence of a Leucine–Rich Repeat", Human Molec. Genetics 4:575–582.
Hughes, J. et al., 1995, "The Polycystic Kidney Disease 1 (PKD1) Gene Encodes a Novel Protein with Multiple Cell Recognition Domains", Nature Genetics 10:151–159.
Adams, M. et al., 1993, "3,400 New Expressed Sequence Tags Identify Diversity of Transcripts in Human Brain", Nature Genetics 4:256–267.
Campbell, Monoclonal Antibody Technology, ed. Elsiever Science Publishers p. 1–32, 1986.
European Polycystic Kidney Disease Consortium Cell vol. 77 p. 881, Jun. 1994.

*Primary Examiner*—Sheela Huff
*Attorney, Agent, or Firm*—Pennie & Edmonds, LLP

[57] ABSTRACT

The present invention relates to the identification of the autosomal dominant polycystic kidney disease (PKD) gene and high throughput assays to identify compounds that interfere with PKD activity. Interfering compounds that inhibit the expression, synthesis and/or bioactivity of the PKD gene product can be used therapeutically to treat polycystic kidney disease.

30 Claims, 28 Drawing Sheets

FIG.5B (CONT. ON FIG. 5C)

| | SIZE | FUN53 | FUN54 | FUN59 | FUN52 | FHKB21 | NKG11 | FUN49 | FUN34 | BK156 | FK7 | FK11 | BK194 | BK241 | KC8 | cDNAPCR |
|---|---|---|---|---|---|---|---|---|---|---|---|---|---|---|---|---|
| EXON1 | 443 | | | | | | | | | | | | | | | |
| EXON2 | 72 | X | X | X | | | | | | | | | | | | |
| EXON3 | 72 | X | X | X | | | | | | | | | | | | |
| EXON4 | 170 | X | X | X | X | | | | | | | | | | | |
| EXON5 | 672 | X | X | X | X | X | | | | X | | | | | | |
| EXON6 | 184 | X | X | X | X | X | | | | X | | | | | | |
| EXON7 | 221 | | | | X | X | | | | | | | | | | |
| EXON7A | 163 | | | | | X | | | | X | | | | | | |
| EXON8 | 116 | | | | X | X | | | | | | | | | | |
| EXON9 | 127 | | | | X | X | | | | | | | | | | |
| EXON10 | 248 | | | | X | X | | | | | | | | | | |
| EXON11 | 756 | | | | X | | | | | | | | | | | |
| EXON12 | 136 | | | | | | | | | | | | | | | |
| EXON12A | 132 | | | | | | X | | | | | | | | | |
| EXON13 | 176 | | | | X | | X | | | | | | | | | |
| EXON14 | 134 | | | | X | | X | X | | | | | | | | |
| EXON15 | 3617 | | | | | | | | | | X | | | | | X |
| EXON15A | 89 | | | | X | | | | | | | | | | | |
| EXON15B | 327 | | | | | | | | | | | | | | | |
| EXON16 | 153 | | | | | | | X | | X | | | | | | |
| EXON17 | 172 | | | | | | | | | X | X | | | | | |
| EXON18 | 144 | | | | X | | | | X | X | X | | | | | X |
| EXON19 | 280 | | | | X | | | | X | X | X | X | | | | |
| EXON20 | 214 | | | | X | | | | X | X | X | X | | | | X |
| EXON21 | 160 | | | | | | | | X | X | X | X | | | | |
| EXON22 | 153 | | | | | | | | X | X | X | X | | | | |
| EXON23 | 145 | | | | | | | | X | X | X | X | | | | |
| EXON24 | 630 | | | | | | | | X | | X | | X | | | |

(FROM FIG. 5B)

| | SIZE | FUN53 | FUN54 | FUN59 | FUN52 | FHKB21 | NKG11 | FUN49 | FUN34 | BK156 | FK7 | FK11 | BK194 | BK241 | KG8 | cDNAPCR |
|---|---|---|---|---|---|---|---|---|---|---|---|---|---|---|---|---|
| EXON24A | 380 | | | | | | | | | | | X | | | | |
| EXON24B | 125 | | | | | | | | | | | X | | | | |
| EXON25 | 157 | | | | | | | | | | X | X | X | | | |
| EXON26 | 253 | | | | | | | | X | | X | X | X | | | |
| EXON27 | 196 | | | | | | | | | | X | X | | | | |
| EXON28 | 171 | | | | | | | | | | | | X | X | | |
| EXON29 | 144 | | | | | | | | | | | | X | X | | |
| EXON30 | 211 | | | | | | | | | | | | X | X | | |
| EXON31 | 127 | | | | | | | | | | | | X | X | | |
| EXON32 | 117 | | | | | | | | | | X | X | X | | | |
| EXON33 | 53 | | | | | | | | | | | | | X | | |
| EXON33A | 50 | | | | | | | | | | | | | | | |
| EXON34 | 185 | | | | | | | | | | | | X | | | |
| EXON35 | 94 | | | | | | | | | | | | | | | |
| EXON36 | 119 | | | | | | | | | | | | | | X | X |
| EXON37 | 203 | | | | | | | | | | | | | | X | X |
| EXON38 | 195 | | | | | | | | | | | | | | X | X |
| EXON39 | 140 | | | | | | | | | | | | | | X | X |
| EXON40 | 113 | | | | | | | | | | | | | | X | X |
| EXON41 | 157 | | | | | | | | | | | | | | X | |
| EXON42 | 111 | | | | | | | | | | | | | | X | |
| EXON43 | 175 | | | | | | | | | | | | | | X | |
| EXON44 | 292 | | | | | | | | | | | | | | X | |
| EXON45 | 135 | | | | | | | | | | | | | | X | |
| EXON46 | 1770 | | | | | | | | | | | | | | | |
| BOLD | DENOTES EXONS NOT INCLUDED IN FINAL PROTEIN | | | | | | | | | | | | | | | |

FIG. 5C

```
  1   ATG CCG CCC GCC GCG CCC GCC CGC CTG GCG CTG GCC CTG GGC CTG GGC CTG TGG CTC GGG   60
  1    M   P   P   A   A   P   A   R   L   A   L   A   L   G   L   G   L   W   L   G    20

61   GCG CTG GCG GGG GGG CCC GGG CGC GGC TGC GGG CCC TGC GAG CCC CCC TGC CTC TGC GGG  120
 21    A   L   A   G   G   P   G   R   G   C   G   P   C   E   P   P   C   L   C   G    40

121   CCA GCG CCC GGC GCC GCC TGC CGC GTC AAC TGC TCG GGC CGC GGG CTG CGG ACG CTC GGT  180
 41    P   A   P   G   A   A   C   R   V   N   C   S   G   R   G   L   R   T   L   G    60

181   CCC GCG CTG CGC ATC CCC GCG GAC GCC ACA GAG CTA GAC GTC TCC CAC AAC CTG CTC CGG  240
 61    P   A   L   R   I   P   A   D   A   T   E   L   D   V   S   H   N   L   L   R    80

241   GCG CTG GAC GTT GGG CTC CTG GCG AAC CTC TCG GCG CTG GCA GAG CTG GAT ATA AGC AAC  300
 81    A   L   D   V   G   L   L   A   N   L   S   A   L   A   E   L   D   I   S   N   100

301   AAC AAG ATT TCT ACG TTA GAA GAA GGA ATA TTT GCT AAT TTA TTT AAT TTA AGT GAA ATA  360
101    N   K   I   S   T   L   E   E   G   I   F   A   N   L   F   N   L   S   E   I   120

361   AAC CTG AGT GGG AAC CCG TTT GAG TGT GAC TGT GGC CTG GCG TGG CTG CCG CAA TGG GCG  420
121    N   L   S   G   N   P   F   E   C   D   C   G   L   A   W   L   P   Q   W   A   140

421   GAG GAG CAG CAG GTG CGG GTG GTG CAG CCC GAG GCA GCC ACG TGT GCT GGG CCT GGC TCC  480
141    E   E   Q   Q   V   R   V   V   Q   P   E   A   A   T   C   A   G   P   G   S   160

481   CTG GCT GGC CAG CCT CTG CTT GGC ATC CCC TTG CTG GAC AGT GGC TGT GGT GAG GAG TAT  540
161    L   A   G   Q   P   L   L   G   I   P   L   L   D   S   G   C   G   E   E   Y   180

541   GTC GCC TGC CTC CCT GAC AAC AGC TCA GGC ACC GTG GCA GCA GTG TCC TTT TCA GCT GCC  600
181    V   A   C   L   P   D   N   S   S   G   T   V   A   A   V   S   F   S   A   A   200

601   CAC GAA GGC CTG CTT CAG CCA GAG GCC TGC AGC GCC TTC TGC TTC TCC ACC GGC CAG GGC  660
201    H   E   G   L   L   Q   P   E   A   C   S   A   F   C   F   S   T   G   Q   G   220

661   CTC GCA GCC CTC TCG GAG CAG GGC TGG TGC CTG TGT GGG GCG GCC CAG CCC TCC AGT GCC  720
221    L   A   A   L   S   E   Q   G   W   C   L   C   G   A   A   Q   P   S   S   A   240

721   TCC TTT GCC TGC CTG TCC CTC TGC TCC GGG CCC CCG GCA CCT CCT GCC CCC ACC TGT AGG  780
241    S   F   A   C   L   S   L   C   S   G   P   P   A   P   P   A   P   T   C   R   260

781   GGC CCC ACC CTC CTC CAG CAC GTC TTC CCT GCC TCC CCA GGG GCC ACC CTG GTG GGG CCC  840
261    G   P   T   L   L   Q   H   V   F   P   A   S   P   G   A   T   L   V   G   P   280
```

FIG.6A

```
841  CAC GGA CCT CTG GCC TCT GGC CAG CTA GCA GCC TTC CAC ATC GCT GCC CCG CTC CCT GTC  900
281   H   G   P   L   A   S   G   Q   L   A   A   F   H   I   A   A   P   L   P   V   300

901  ACT GAC ACA CGC TGG GAC TTC GGA GAC GGC TCC GCC GAG GTG GAT GCC GCT GGG CCG GCT  960
301   T   D   T   R   W   D   F   G   D   G   S   A   E   V   D   A   A   G   P   A   320

961  GCC TCG CAT CGC TAT GTG CTG CCT GGG CGC TAT CAC GTG ACG GCC GTG CTG GCC CTG GGG  1020
321   A   S   H   R   Y   V   L   P   G   R   Y   H   V   T   A   V   L   A   L   G   340

1021 GCC GGC TCA GCC CTG CTG GGG ACA GAC GTG CAG GTG GAA GCG GCA CCT GCC GCC CTG GAG  1080
341   A   G   S   A   L   L   G   T   D   V   Q   V   E   A   A   P   A   A   L   E   360

1081 CTC GTG TGC CCG TCC TCG GTG CAG AGT GAC GAG AGC CTC GAC CTC AGC ATC CAG AAC CGC  1140
361   L   V   C   P   S   S   V   Q   S   D   E   S   L   D   L   S   I   Q   N   R   380

1141 GGT GGT TCA GGC CTG GAG GCC GCC TAC AGC ATC GTG GCC CTG GGC GAG GAG CCG GCC CGA  1200
381   G   G   S   G   L   E   A   A   Y   S   I   V   A   L   G   E   E   P   A   R   400

1201 GCG GTG CAC CCG CTC TGC CCC TCG GAC ACG GAG ATC TTC CCT GGC AAC GGG CAC TGC TAC  1260
401   A   V   H   P   L   C   P   S   D   T   E   I   F   P   G   N   G   H   C   Y   420

1261 CGC CTG GTG GTG GAG AAG GCG GCC TGG CTG CAG GCG CAG GAG CAG TGT CAG GCC TGG GCC  1320
421   R   L   V   V   E   K   A   A   W   L   Q   A   Q   E   Q   C   Q   A   W   A   440

1321 GGG GCC GCC CTG GCA ATG GTG GAC AGT CCC GCC GTG CAG CGC TTC CTG GTC TCC CGG GTC  1380
441   G   A   A   L   A   M   V   D   S   P   A   V   Q   R   F   L   V   S   R   V   460

1381 ACC AGG AGC CTA GAC GTG TGG ATC GGC TTC TCG ACT GTG CAG GGG GTG GAG GTG GGC CCA  1440
461   T   R   S   L   D   V   W   I   G   F   S   T   V   Q   G   V   E   V   G   P   480

1441 GCG CCG CAG GGC GAG GCC TTC AGC CTG GAG AGC TGC CAG AAC TGG CTG CCC GGG GAG CCA  1500
481   A   P   Q   G   E   A   F   S   L   E   S   C   Q   N   W   L   P   G   E   P   500

1501 CAC CCA GCC ACA GCC GAG CAC TGC GTC CGG CTC GGG CCC ACC GGG TGG TGT AAC ACC GAC  1560
501   H   P   A   T   A   E   H   C   V   R   L   G   P   T   G   W   C   N   T   D   520

1561 CTG TGC TCA GCG CCG CAC AGC TAC GTC TGC GAG CTG CAG CCC GGA GGC CCA GTG CAG GAT  1620
521   L   C   S   A   P   H   S   Y   V   C   E   L   Q   P   G   G   P   V   Q   D   540

1621 GCC GAG AAC CTC CTC GTG GGA GCG CCC AGT GGG GAC CTG CAG GGA CCC CTG ACG CCT CTG  1680
541   A   E   N   L   L   V   G   A   P   S   G   D   L   Q   G   P   L   T   P   L   560
```

FIG. 6B

```
1681 GCA CAG CAG GAC GGC CTC TCA GCC CCG CAC GAG CCC GTG GAG GTC ATG GTA TTC CCG GGC 1740
561   A   Q   Q   D   G   L   S   A   P   H   E   P   V   E   V   M   V   F   P   G  580

1741 CTG CGT CTG AGC CGT GAA GCC TTC CTC ACC ACG GCC GAA TTT GGG ACC CAG GAG CTC CGG 1800
581   L   R   L   S   R   E   A   F   L   T   T   A   E   F   G   T   Q   E   L   R  600

1801 CGG CCC GCC CAG CTG CGG CTG CAG GTG TAC CGG CTC CTC AGC ACA GCA GGG ACC CCG GAG 1860
601   R   P   A   Q   L   R   L   Q   V   Y   R   L   L   S   T   A   G   T   P   E  620

1861 AAC GGC AGC GAG CCT GAG AGC AGG TCC CCG GAC AAC AGG ACC CAG CTG GCC CCC GCG TGC 1920
621   N   G   S   E   P   E   S   R   S   P   D   N   R   T   Q   L   A   P   A   C  640

1921 ATG CCA GGG GGA CGC TGG TGC CCT GGA GCC AAC ATC TGC TTG CCG CTG GAC GCC TCC TGC 1980
641   M   P   G   G   R   W   C   P   G   A   N   I   C   L   P   L   D   A   S   C  660

1981 CAC CCC CAG GCC TGC GCC AAT GGC TGC ACG TCA GGG CCA GGG CTA CCC GGG GCC CCC TAT 2040
661   H   P   Q   A   C   A   N   G   C   T   S   G   P   G   L   P   G   A   P   Y  680

2041 GCG CTA TGG AGA GAG TTC CTC TTC TCC GTT CCC GCG GGG CCC CCC GCG CAG TAC TCG GTC 2100
681   A   L   W   R   E   F   L   F   S   V   P   A   G   P   P   A   Q   Y   S   V  700

2101 ACC CTC CAC GGC CAG GAT GTC CTC ATG CTC CCT GGT GAC CTC GTT GGC TTG CAG CAC GAC 2160
701   T   L   H   G   Q   D   V   L   M   L   P   G   D   L   V   G   L   Q   H   D  720

2161 GCT GGC CCT GGC GCC CTC CTG CAC TGC TCG CCG GCT CCC GGC CAC CCT GGT CCC CGG GCC 2220
721   A   G   P   G   A   L   L   H   C   S   P   A   P   G   H   P   G   P   R   A  740

2221 CCG TAC CTC TCC GCC AAC GCC TCG TCA TGG CTG CCC CAC TTG CCA GCC CAG CTG GAG GGC 2280
741   P   Y   L   S   A   N   A   S   S   W   L   P   H   L   P   A   Q   L   E   G  760

2281 ACT TGG GGC TGC CCT GCC TGT GCC CTG CGG CTG CTT GCA CAA CGG GAA CAG CTC ACC GTG 2340
761   T   W   G   C   P   A   C   A   L   R   L   L   A   Q   R   E   Q   L   T   V  780

2341 CTG CTG GGC TTG AGG CCC AAC CCT GGA CTG CGG CTG CCT GGG CGC TAT GAG GTC CGG GCA 2400
781   L   L   G   L   R   P   N   P   G   L   R   L   P   G   R   Y   E   V   R   A  800

2401 GAG GTG GGC AAT GGC GTG TCC AGG CAC AAC CTC TCC TGC AGC TTT GAC GTG GTC TCC CCA 2460
801   E   V   G   N   G   V   S   R   H   N   L   S   C   S   F   D   V   V   S   P  820

2461 GTG GCT GGG CTG CGG GTC ATC TAC CCT GCC CCC CGC GAC GGC CGC CTC TAC GTG CCC ACC 2520
821   V   A   G   L   R   V   I   Y   P   A   P   R   D   G   R   L   Y   V   P   T  840
```

FIG.6C

```
2521  AAC GGC TCA GCC TTG GTG CTC CAG GTG GAC TCT GGT GCC AAC GCC ACG GCC ACG GCT CGC  2580
841    N   G   S   A   L   V   L   Q   V   D   S   G   A   N   A   T   A   T   A   R   860

2581  TGG CCT GGG GGC AGT CTC AGC GCC CGC TTT GAG AAT GTC TGC CCT GCC CTG GTG GCC ACC  2640
861    W   P   G   G   S   L   S   A   R   F   E   N   V   C   P   A   L   V   A   T   880

2641  TTC GTG CCC GCC TGC CCC TGG GAG ACC AAC GAT ACC CTG TTC TCA GTG GTA GCA CTG CCG  2700
881    F   V   P   A   C   P   W   E   T   N   D   T   L   F   S   V   V   A   L   P   900

2701  TGG CTC AGT GAG GGG GAG CAC GTG GTG GAC GTG GTG GTG GAA AAC AGC GCC AGC CGG GCC  2760
901    W   L   S   E   G   E   H   V   V   D   V   V   V   E   N   S   A   S   R   A   920

2761  AAC CTC AGC CTG CGG GTG ACG GCG GAG GAG CCC ATC TGT GGC CTC CGC GCC ACG CCC AGC  2820
921    N   L   S   L   R   V   T   A   E   E   P   I   C   G   L   R   A   T   P   S   940

2821  CCC GAG GCC CGT GTA CTG CAG GGA GTC CTA GTG AGG TAC AGC CCC GTG GTG GAG GCC GGC  2880
941    P   E   A   R   V   L   Q   G   V   L   V   R   Y   S   P   V   V   E   A   G   960

2881  TCG GAC ATG GTC TTC CGG TGG ACC ATC AAC GAC AAG CAG TCC CTG ACC TTC CAG AAC GTG  2940
961    S   D   M   V   F   R   W   T   I   N   D   K   Q   S   L   T   F   Q   N   V   980

2941  GTC TTC AAT GTC ATT TAT CAG AGC GCG GCG GTC TTC AAG CTC TCA CTG ACG GCC TCC AAC  3000
981    V   F   N   V   I   Y   Q   S   A   A   V   F   K   L   S   L   T   A   S   N   1000

3001  CAC GTG AGC AAC GTC ACC GTG AAC TAC AAC GTA ACC GTG GAG CGG ATG AAC AGG ATG CAG  3060
1001   H   V   S   N   V   T   V   N   Y   N   V   T   V   E   R   M   N   R   M   Q   1020

3061  GGT CTG CAG GTC TCC ACA GTG CCG GCC GTG CTG TCC CCC AAT GCC ACG CTA GCA CTG ACG  3120
1021   G   L   Q   V   S   T   V   P   A   V   L   S   P   N   A   T   L   A   L   T   1040

3121  GCG GGC GTG CTG GTG GAC TCG GCC GTG GAG GTG GCC TTC CTG TGG ACC TTT GGG GAT GGG  3180
1041   A   G   V   L   V   D   S   A   V   E   V   A   F   L   W   T   F   G   D   G   1060

3181  GAG CAG GCC CTC CAC CAG TTC CAG CCT CCG TAC AAC GAG TCC TTC CCA GTT CCA GAC CCC  3240
1061   E   Q   A   L   H   Q   F   Q   P   P   Y   N   E   S   F   P   V   P   D   P   1080

3241  TCG GTG GCC CAG GTG CTG GTG GAG CAC AAT GTC ACG CAC ACC TAC GCT GCC CCA GGT GAG  3300
1081   S   V   A   Q   V   L   V   E   H   N   V   T   H   T   Y   A   A   P   G   E   1100
```

FIG.6D

```
3301  TAC CTC CTG ACC GTG CTG GCA TCT AAT GCC TTC GAG AAC CTG ACG CAG CAG GTC CCT GTG  3360
1101   Y   L   L   T   V   L   A   S   N   A   F   E   N   L   T   Q   Q   V   P   V   1120

3361  AGC GTG CGC GCC TCC CTG CCC TCC GTG GCT GTG GGT GTG AGT GAC GGC GTC CTG GTG GCC  3420
1121   S   V   R   A   S   L   P   S   V   A   V   G   V   S   D   G   V   L   V   A   1140

3421  GGC CGG CCC GTC ACC TTC TAC CCG CAC CCG CTG CCC TCG CCT GGG GGT GTT CTT TAC ACG  3480
1141   G   R   P   V   T   F   Y   P   H   P   L   P   S   P   G   G   V   L   Y   T   1160

3481  TGG GAC TTC GGG GAC GGC TCC CCT GTC CTG ACC CAG AGC CAG CCG GCT GCC AAC CAC ACC  3540
1161   W   D   F   G   D   G   S   P   V   L   T   Q   S   Q   P   A   A   N   H   T   1180

3541  TAT GCC TCG AGG GGC ACC TAC CAC GTG CGC CTG GAG GTC AAC AAC ACG GTG AGC GGT GCG  3600
1181   Y   A   S   R   G   T   Y   H   V   R   L   E   V   N   N   T   V   S   G   A   1200

3601  GCG GCC CAG GCG GAT GTG CGC GTC TTT GAG GAG CTC CGC GGA CTC AGC GTG GAC ATG AGC  3660
1201   A   A   Q   A   D   V   R   V   F   E   E   L   R   G   L   S   V   D   M   S   1220

3661  CTG GCC GTG GAG CAG GGC GCC CCC GTG GTG GTC AGC GCC GCG GTG CAG ACG GGC GAC AAC  3720
1221   L   A   V   E   Q   G   A   P   V   V   V   S   A   A   V   Q   T   G   D   N   1240

3721  ATC ACG TGG ACC TTC GAC ATG GGG GAC GGC ACC GTG CTG TCG GGC CCG GAG GCA ACA GTG  3780
1241   I   T   W   T   F   D   M   G   D   G   T   V   L   S   G   P   E   A   T   V   1260

3781  GAG CAT GTG TAC CTG CGG GCA CAG AAC TGC ACA GTG ACC GTG GGT GCG GGC AGC CCC GCC  3840
1261   E   H   V   Y   L   R   A   Q   N   C   T   V   T   V   G   A   G   S   P   A   1280

3841  GGC CAC CTG GCC CGG AGC CTG CAC GTG CTG GTC TTC GTC CTG GAG GTG CTG CGC GTT GAA  3900
1281   G   H   L   A   R   S   L   H   V   L   V   F   V   L   E   V   L   R   V   E   1300

3901  CCC GCC GCC TGC ATC CCC ACG CAG CCT GAC GCG CGG CTC ACG GCC TAC GTC ACC GGG AAC  3960
1301   P   A   A   C   I   P   T   Q   P   D   A   R   L   T   A   Y   V   T   G   N   1320

3961  CCG GCC CAC TAC CTC TTC GAC TGG ACC TTC GGG GAT GGC TCC TCC AAC ACG ACC GTG CGG  4020
1321   P   A   H   Y   L   F   D   W   T   F   G   D   G   S   S   N   T   T   V   R   1340

4021  GGG TGC CCG ACG GTG ACA CAC AAC TTC ACG CGG AGC GGC ACG TTC CCC CTG GCC CTG GTG  4080
1341   G   C   P   T   V   T   H   N   F   T   R   S   G   T   F   P   L   A   L   V   1360
```

FIG.6E

```
4081 CTG TCC AGC CGC GTG AAC AGG GCG CAT TAC TTC ACC AGC ATC TGC GTG GAG CCA GAG GTG 4140
1361  L   S   S   R   V   N   R   A   H   Y   F   T   S   I   C   V   E   P   E   V  1380

4141 GGC AAC GTC ACC CTG CAG CCA GAG AGG CAG TTT GTG CAG CTC GGG GAC GAG GCC TGG CTG 4200
1381  G   N   V   T   L   Q   P   E   R   Q   F   V   Q   L   G   D   E   A   W   L  1400

4201 GTG GCA TGT GCC TGG CCC CCG TTC CCC TAC CGC TAC ACC TGG GAC TTT GGC ACC GAG GAA 4260
1401  V   A   C   A   W   P   P   F   P   Y   R   Y   T   W   D   F   G   T   E   E  1420

4261 GCC GCC CCC ACC CGT GCC AGG GGC CCT GAG GTG ACG TTC ATC TAC CGA GAC CCA GGC TCC 4320
1421  A   A   P   T   R   A   R   G   P   E   V   T   F   I   Y   R   D   P   G   S  1440

4321 TAT CTT GTG ACA GTC ACC GCG TCC AAC AAC ATC TCT GCT GCC AAT GAC TCA GCC CTG GTG 4380
1441  Y   L   V   T   V   T   A   S   N   N   I   S   A   A   N   D   S   A   L   V  1460

4381 GAG GTG CAG GAG CCC GTG CTG GTC ACC AGC ATC AAG GTC AAT GGC TCC CTT GGG CTG GAG 4440
1461  E   V   Q   E   P   V   L   V   T   S   I   K   V   N   G   S   L   G   L   E  1480

4441 CTG CAG CAG CCG TAC CTG TTC TCT GCT GTG GGC CGT GGG CGC CCC GCC AGC TAC CTG TGG 4500
1481  L   Q   Q   P   Y   L   F   S   A   V   G   R   G   R   P   A   S   Y   L   W  1500

4501 GAT CTG GGG GAC GGT GGG TGG CTC GAG GGT CCG GAG GTC ACC CAC GCT TAC AAC AGC ACA 4560
1501  D   L   G   D   G   G   W   L   E   G   P   E   V   T   H   A   Y   N   S   T  1520

4561 GGT GAC TTC ACC GTT AGG GTG GCC GGC TGG AAT GAG GTG AGC CGC AGC GAG GCC TGG CTC 4620
1521  G   D   F   T   V   R   V   A   G   W   N   E   V   S   R   S   E   A   W   L  1540

4621 AAT GTG ACG GTG AAG CGG CGC GTG CGG GGG CTC GTC GTC AAT GCA AGC CGC ACG GTG GTG 4680
1541  N   V   T   V   K   R   R   V   R   G   L   V   V   N   A   S   R   T   V   V  1560

4681 CCC CTG AAT GGG AGC GTG AGC TTC AGC ACG TCG CTG GAG GCC GGC AGT GAT GTG CGC TAT 4740
1561  P   L   N   G   S   V   S   F   S   T   S   L   E   A   G   S   D   V   R   Y  1580

4741 TCC TGG GTG CTC TGT GAC CGC TGC ACG CCC ATC CCT GGG GGT CCT ACC ATC TCT TAC ACC 4800
1581  S   W   V   L   C   D   R   C   T   P   I   P   G   G   P   T   I   S   Y   T  1600

4801 TTC CGC TCC GTG GGC ACC TTC AAT ATC ATC GTC ACG GCT GAG AAC GAG GTG GGC TCC GCC 4860
1601  F   R   S   V   G   T   F   N   I   I   V   T   A   E   N   E   V   G   S   A  1620
```

FIG.6F

```
4861  CAG GAC AGC ATC TTC GTC TAT GTC CTG CAG CTC ATA GAG GGG CTG CAG GTG GTG GGC GGT  4920
1621   Q   D   S   I   F   V   Y   V   L   Q   L   I   E   G   L   Q   V   V   G   G  1640

4921  GGC CGC TAC TTC CCC ACC AAC CAC ACG GTA CAG CTG CAG GCC GTG GTT AGG GAT GGC ACC  4980
1641   G   R   Y   F   P   T   N   H   T   V   Q   L   Q   A   V   V   R   D   G   T  1660

4981  AAC GTC TCC TAC AGC TGG ACT GCC TGG AGG GAC AGG GGC CCG GCC CTG GCC GGC AGC GGC  5040
1661   N   V   S   Y   S   W   T   A   W   R   D   R   G   P   A   L   A   G   S   G  1680

5041  AAA GGC TTC TCG CTC ACC GTG CTC GAG GCC GGC ACC TAC CAT GTG CAG CTG CGG GCC ACC  5100
1681   K   G   F   S   L   T   V   L   E   A   G   T   Y   H   V   Q   L   R   A   T  1700

5101  AAC ATG CTG GGC AGC GCC TGG GCC GAC TGC ACC ATG GAC TTC GTG GAG CCT GTG GGG TGG  5160
1701   N   M   L   G   S   A   W   A   D   C   T   M   D   F   V   E   P   V   G   W  1720

5161  CTG ATG GTG GCC GCC TCC CCG AAC CCA GCT GCC GTC AAC ACA AGC GTC ACC CTC AGT GCC  5220
1721   L   M   V   A   A   S   P   N   P   A   A   V   N   T   S   V   T   L   S   A  1740

5221  GAG CTG GCT GGT GGC AGT GGT GTC GTA TAC ACT TGG TCC TTG GAG GAG GGG CTG AGC TGG  5280
1741   E   L   A   G   G   S   G   V   V   Y   T   W   S   L   E   E   G   L   S   W  1760

5281  GAG ACC TCC GAG CCA TTT ACC ACC CAT AGC TTC CCC ACA CCC GGC CTG CAC TTG GTC ACC  5340
1761   E   T   S   E   P   F   T   T   H   S   F   P   T   P   G   L   H   L   V   T  1780

5341  ATG ACG GCA GGG AAC CCG CTG GGC TCA GCC AAC GCC ACC GTG GAA GTG GAT GTG CAG GTG  5400
1781   M   T   A   G   N   P   L   G   S   A   N   A   T   V   E   V   D   V   Q   V  1800

5401  CCT GTG AGT GGC CTC AGC ATC AGG GCC AGC GAG CCC GGA GGC AGC TTC GTG GCG GCC GGG  5460
1801   P   V   S   G   L   S   I   R   A   S   E   P   G   G   S   F   V   A   A   G  1820

5461  TCC TCT GTG CCC TTT TGG GGG CAG CTG GCC ACG GGC ACC AAT GTG AGC TGG TGC TGG GCT  5520
1821   S   S   V   P   F   W   G   Q   L   A   T   G   T   N   V   S   W   C   W   A  1840

5521  GTG CCC GGC GGC AGC AGC AAG CGT GGC CCT CAT GTC ACC ATG GTC TTC CCG GAT GCT GGC  5580
1841   V   P   G   G   S   S   K   R   G   P   H   V   T   M   V   F   P   D   A   G  1860

5581  ACC TTC TCC ATC CGG CTC AAT GCC TCC AAC GCA GTC AGC TGG GTC TCA GCC ACG TAC AAC  5640
1861   T   F   S   I   R   L   N   A   S   N   A   V   S   W   V   S   A   T   Y   N  1880
```

FIG.6G

```
5641 CTC ACG GCG GAG GAG CCC ATC GTG GGC CTG GTG CTG TGG GCC AGC AGC AAG GTG GTG GCG 5700
1881  L   T   A   E   E   P   I   V   G   L   V   L   W   A   S   S   K   V   V   A   1900

5701 CCC GGG CAG CTG GTC CAT TTT CAG ATC CTG CTG GCT GCC GGC TCA GCT GTC ACC TTC CGC 5760
1901  P   G   Q   L   V   H   F   Q   I   L   L   A   A   G   S   A   V   T   F   R   1920

5761 CTA CAG GTC GGC GGG GCC AAC CCC GAG GTG CTC CCC GGG CCC CGT TTC TCC CAC AGC TTC 5820
1921  L   Q   V   G   G   A   N   P   E   V   L   P   G   P   R   F   S   H   S   F   1940

5821 CCC CGC GTC GGA GAC CAC GTG GTG AGC GTG CGG GGC AAA AAC CAC GTG AGC TGG GCC CAG 5880
1941  P   R   V   G   D   H   V   V   S   V   R   G   K   N   H   V   S   W   A   Q   1960

5881 GCG CAG GTC CGC ATC GTG GTG CTG GAG GCC GTG AGT GGG CTG CAG GTG CCC AAC TGC TGC 5940
1961  A   Q   V   R   I   V   V   L   E   A   V   S   G   L   Q   V   P   N   C   C   1980

5941 GAG CCT GGC ATC GCC ACG GGC ACT GAG AGG AAC TTC ACA GCC CGC GTG CAG CGC GGC TCT 6000
1981  E   P   G   I   A   T   G   T   E   R   N   F   T   A   R   V   Q   R   G   S   2000

6001 CGG GTC GCC TAC GCC TGG TAC TTC TCG CTG CAG AAG GTC CAG GGC GAC TCG CTG GTC ATC 6060
2001  R   V   A   Y   A   W   Y   F   S   L   Q   K   V   Q   G   D   S   L   V   I   2020

6061 CTG TCG GGC CGC GAC GTC ACC TAC ACG CCC GTG GCC GCG GGG CTG TTG GAG ATC CAG GTG 6120
2021  L   S   G   R   D   V   T   Y   T   P   V   A   A   G   L   L   E   I   Q   V   2040

6121 CGC GCC TTC AAC GCC CTG GGC AGT GAG AAC CGC ACG CTG GTG CTG GAG GTT CAG GAC GCC 6180
2041  R   A   F   N   A   L   G   S   E   N   R   T   L   V   L   E   V   Q   D   A   2060

6181 GTC CAG TAT GTG GCC CTG CAG AGC GGC CCC TGC TTC ACC AAC CGC TCG GCG CAG TTT GAG 6240
2061  V   Q   Y   V   A   L   Q   S   G   P   C   F   T   N   R   S   A   Q   F   E   2080

6241 GCC GCC ACC AGC CCC AGC CCC CGG CGT GTG GCC TAC CAC TGG GAC TTT GGG GAT GGG TCG 6300
2081  A   A   T   S   P   S   P   R   R   V   A   Y   H   W   D   F   G   D   G   S   2100

6301 CCA GGG CAG GAC ACA GAT GAG CCC AGG GCC GAG CAC TCC TAC CTG AGG CCT GGG GAC TAC 6360
2101  P   G   Q   D   T   D   E   P   R   A   E   H   S   Y   L   R   P   G   D   Y   2120

6361 CGC GTG CAG GTG AAC GCC TCC AAC CTG GTG AGC TTC TTC GTG GCG CAG GCC ACG GTG ACC 6420
2121  R   V   Q   V   N   A   S   N   L   V   S   F   F   V   A   Q   A   T   V   T   2140
```

FIG.6H

```
6421  GTC CAG GTG CTG GCC TGC CGG GAG CCG GAG GTG GAC GTG GTC CTG CCC CTG CAG GTG CTG  6480
2141   V   Q   V   L   A   C   R   E   P   E   V   D   V   V   L   P   L   Q   V   L   2160

6481  ATG CGG CGA TCA CAG CGC AAC TAC TTG GAG GCC CAC GTT GAC CTG CGC GAC TGC GTC ACC  6540
2161   M   R   R   S   Q   R   N   Y   L   E   A   H   V   D   L   R   D   C   V   T   2180

6541  TAC CAG ACT GAG TAC CGC TGG GAG GTG TAT CGC ACC GCC AGC TGC CAG CGG CCG GGG CGC  6600
2181   Y   Q   T   E   Y   R   W   E   V   Y   R   T   A   S   C   Q   R   P   G   R   2200

6601  CCA GCG CGT GTG GCC CTG CCC GGC GTG GAC GTG AGC CGG CCT CGG CTG GTG CTG CCG CGG  6660
2201   P   A   R   V   A   L   P   G   V   D   V   S   R   P   R   L   V   L   P   R   2220

6661  CTG GCG CTG CCT GTG GGG CAC TAC TGC TTT GTG TTT GTC GTG TCA TTT GGG GAC ACG CCA  6720
2221   L   A   L   P   V   G   H   Y   C   F   V   F   V   V   S   F   G   D   T   P   2240

6721  CTG ACA CAG AGC ATC CAG GCC AAT GTG ACG GTG GCC CCC GAG CGC CTG GTG CCC ATC ATT  6780
2241   L   T   Q   S   I   Q   A   N   V   T   V   A   P   E   R   L   V   P   I   I   2260

6781  GAG GGT GGC TCA TAC CGC GTG TGG TCA GAC ACA CGG GAC CTG GTG CTG GAT GGG AGC GAG  6840
2261   E   G   G   S   Y   R   V   W   S   D   T   R   D   L   V   L   D   G   S   E   2280

6841  TCC TAC GAC CCC AAC CTG GAG GAC GGC GAC CAG ACG CCG CTC AGT TTC CAC TGG GCC TGT  6900
2281   S   Y   D   P   N   L   E   D   G   D   Q   T   P   L   S   F   H   W   A   C   2300

6901  GTG GCT TCG ACA CAG AGG GAG GCT GGC GGG TGT GCG CTG AAC TTT GGG CCC CGC GGG AGC  6960
2301   V   A   S   T   Q   R   E   A   G   G   C   A   L   N   F   G   P   R   G   S   2320

6961  AGC ACG GTC ACC ATT CCA CGG GAG CGG CTG GCG GCT GGC GTG GAG TAC ACC TTC AGC CTG  7020
2321   S   T   V   T   I   P   R   E   R   L   A   A   G   V   E   Y   T   F   S   L   2340

7021  ACC GTG TGG AAG GCC GGC CGC AAG GAG GAG GCC ACC AAC CAG ACG GTG CTG ATC CGG AGT  7080
2341   T   V   W   K   A   G   R   K   E   E   A   T   N   Q   T   V   L   I   R   S   2360

7081  GGC CGG GTG CCC ATT GTG TCC TTG GAG TGT GTG TCC TGC AAG GCA CAG GCC GTG TAC GAA  7140
2361   G   R   V   P   I   V   S   L   E   C   V   S   C   K   A   Q   A   V   Y   E   2380

7141  GTG AGC CGC AGC TCC TAC GTG TAC TTG GAG GGC CGC TGC CTC AAT TGC AGC AGC GGC TCC  7200
2381   V   S   R   S   S   Y   V   Y   L   E   G   R   C   L   N   C   S   S   G   S   2400
```

FIG.61

```
7201 AAG CGA GGG CGG TGG GCT GCA CGT ACG TTC AGC AAC AAG ACG CTG GTG CTG GAT GAG ACC 7260
2401  K   R   G   R   W   A   A   R   T   F   S   N   K   T   L   V   L   D   E   T  2420

7261 ACC ACA TCC ACG GGC AGT GCA GGC ATG CGA CTG GTG CTG CGG CGG GGC GTG CTG CGG GAC 7320
2421  T   T   S   T   G   S   A   G   M   R   L   V   L   R   R   G   V   L   R   D  2440

7321 GGC GAG GGA TAC ACC TTC ACG CTC ACG GTG CTG GGC CGC TCT GGC GAG GAG GAG GGC TGC 7380
2441  G   E   G   Y   T   F   T   L   T   V   L   G   R   S   G   E   E   E   G   C  2460

7381 GCC TCC ATC CGC CTG TCC CCC AAC CGC CCG CCG CTG GGG GGC TCT TGC CGC CTC TTC CCA 7440
2461  A   S   I   R   L   S   P   N   R   P   P   L   G   G   S   C   R   L   F   P  2480

7441 CTG GGC GCT GTG CAC GCC CTC ACC ACC AAG GTG CAC TTC GAA TGC ACG GGC TGG CAT GAC 7500
2481  L   G   A   V   H   A   L   T   T   K   V   H   F   E   C   T   G   W   H   D  2500

7501 GCG GAG GAT GCT GGC GCC CCG CTG GTG TAC GCC CTG CTG CTG CGG CGC TGT CGC CAG GGC 7560
2501  A   E   D   A   G   A   P   L   V   Y   A   L   L   L   R   R   C   R   Q   G  2520

7561 CAC TGC GAG GAG TTC TGT GTC TAC AAG GGC AGC CTC TCC AGC TAC GGA GCC GTG CTG CCC 7620
2521  H   C   E   E   F   C   V   Y   K   G   S   L   S   S   Y   G   A   V   L   P  2540

7621 CCG GGT TTC AGG CCA CAC TTC GAG GTG GGC CTG GCC GTG GTG GTG CAG GAC CAG CTG GGA 7680
2541  P   G   F   R   P   H   F   E   V   G   L   A   V   V   V   Q   D   Q   L   G  2560

7681 GCC GCT GTG GTC GCC CTC AAC AGG TCT TTG GCC ATC ACC CTC CCA GAG CCC AAC GGC AGC 7740
2561  A   A   V   V   A   L   N   R   S   L   A   I   T   L   P   E   P   N   G   S  2580

7741 GCA ACG GGC CTC ACA GTC TGG CTG CAC GGG CTC ACC GCT AGT GTG CTC CCA GGG CTG CTG 7800
2581  A   T   G   L   T   V   W   L   H   G   L   T   A   S   V   L   P   G   L   L  2600

7801 CGG CAG GCC GAT CCC CAG CAC GTC ATC GAG TAC TCG TTG GCC CTG GTC ACC GTG CTG AAC 7860
2601  R   Q   A   D   P   Q   H   V   I   E   Y   S   L   A   L   V   T   V   L   N  2620

7861 GAG TAC GAG CGG GCC CTG GAC GTG GCG GCA GAG CCC AAG CAC GAG CGG CAG CAC CGA GCC 7920
2621  E   Y   E   R   A   L   D   V   A   A   E   P   K   H   E   R   Q   H   R   A  2640

7921 CAG ATA CGC AAG AAC ATC ACG GAG ACT CTG GTG TCC CTG AGG GTC CAC ACT GTG GAT GAC 7980
2641  Q   I   R   K   N   I   T   E   T   L   V   S   L   R   V   H   T   V   D   D  2660
```

FIG.6J

```
7981  ATC CAG CAG ATC GCT GCT GCG CTG GCC CAG TGC ATG GGG CCC AGC AGG GAG CTC GTA TGC  8040
2661   I   Q   Q   I   A   A   A   L   A   Q   C   M   G   P   S   R   E   L   V   C  2680

8041  CGC TCG TGC CTG AAG CAG ACG CTG CAC AAG CTG GAG GCC ATG ATG CTC ATC CTG CAG GCA  8100
2681   R   S   C   L   K   Q   T   L   H   K   L   E   A   M   M   L   I   L   Q   A  2700

8101  GAG ACC ACC GCG GGC ACC GTG ACG CCC ACC GCC ATC GGA GAC AGC ATC CTC AAC ATC ACA  8160
2701   E   T   T   A   G   T   V   T   P   T   A   I   G   D   S   I   L   N   I   T  2720

8161  GGA GAC CTC ATC CAC CTG GCC AGC TCG GAC GTG CGG GCA CCA CAG CCC TCA GAG CTG GGA  8220
2721   G   D   L   I   H   L   A   S   S   D   V   R   A   P   Q   P   S   E   L   G  2740

8221  GCC GAG TCA CCA TCT CGG ATG GTG GCG TCC CAG GCC TAC AAC CTG ACC TCT GCC CTC ATG  8280
2741   A   E   S   P   S   R   M   V   A   S   Q   A   Y   N   L   T   S   A   L   M  2760

8281  CGC ATC CTC ATG CGC TCC CGC GTG CTC AAC GAG GAG CCC CTG ACG CTG GCG GGC GAG GAG  8340
2761   R   I   L   M   R   S   R   V   L   N   E   E   P   L   T   L   A   G   E   E  2780

8341  ATC GTG GCC CAG GGC AAG CGC TCG GAC CCG CGG AGC CTG CTG TGC TAT GGC GGC GCC CCA  8400
2781   I   V   A   Q   G   K   R   S   D   P   R   S   L   L   C   Y   G   G   A   P  2800

8401  GGG CCT GGC TGC CAC TTC TCC ATC CCC GAG GCT TTC AGC GGG GCC CTG GCC AAC CTC AGT  8460
2801   G   P   G   C   H   F   S   I   P   E   A   F   S   G   A   L   A   N   L   S  2820

8461  GAC GTG GTG CAG CTC ATC TTT CTG GTG GAC TCC AAT CCC TTT CCC TTT GGC TAT ATC AGC  8520
2821   D   V   V   Q   L   I   F   L   V   D   S   N   P   F   P   F   G   Y   I   S  2840

8521  AAC TAC ACC GTC TCC ACC AAG GTG GCC TCG ATG GCA TTC CAG ACA CAG GCC GGC GCC CAG  8580
2841   N   Y   T   V   S   T   K   V   A   S   M   A   F   Q   T   Q   A   G   A   Q  2860

8581  ATC CCC ATC GAG CGG CTG GCC TCA GAG CGC GCC ATC ACC GTG AAG GTG CCC AAC AAC TCG  8640
2861   I   P   I   E   R   L   A   S   E   R   A   I   T   V   K   V   P   N   N   S  2880

8641  GAC TGG GCT GCC CGG GGC CAC CGC AGC TCC GCC AAC TCC GCC AAC TCC GTT GTG GTC CAG  8700
2881   D   W   A   A   R   G   H   R   S   S   A   N   S   A   N   S   V   V   V   Q  2900

8701  CCC CAG GCC TCC GTC GGT GCT GTG GTC ACC CTG GAC AGC AGC AAC CCT GCG GCC GGG CTG  8760
2901   P   Q   A   S   V   G   A   V   V   T   L   D   S   S   N   P   A   A   G   L  2920
```

FIG.6K

```
8761 CAT CTG CAG CTC AAC TAT ACG CTG CTG GAC GGC CAC TAC CTG TCT GAG GAA CCT GAG CCC 8820
2921  H   L   Q   L   N   Y   T   L   L   D   G   H   Y   L   S   E   E   P   E   P  2940

8821 TAC CTG GCA GTC TAC CTA CAC TCG GAG CCC CGG CCC AAT GAG CAC AAC TGC TCG GCT AGC 8880
2941  Y   L   A   V   Y   L   H   S   E   P   R   P   N   E   H   N   C   S   A   S  2960

8881 AGG AGG ATC CGC CCA GAG TCA CTC CAG GGT GCT GAC CAC CGG CCC TAC ACC TTC TTC ATT 8940
2961  R   R   I   R   P   E   S   L   Q   G   A   D   H   R   P   Y   T   F   F   I  2980

8941 TCC CCG GGG AGC AGA GAC CCA GCG GGG AGT TAC CAT CTG AAC CTC TCC AGC CAC TTC CGC 9000
2981  S   P   G   S   R   D   P   A   G   S   Y   H   L   N   L   S   S   H   F   R  3000

9001 TGG TCG GCG CTG CAG GTG TCC GTG GGC CTG TAC ACG TCC CTG TGC CAG TAC TTC AGC GAG 9060
3001  W   S   A   L   Q   V   S   V   G   L   Y   T   S   L   C   Q   Y   F   S   E  3020

9061 GAG GAC ATG GTG TGG CGG ACA GAG GGG CTG CTG CCC CTG GAG GAG ACC TCG CCC CGC CAG 9120
3021  E   D   M   V   W   R   T   E   G   L   L   P   L   E   E   T   S   P   R   Q  3040

9121 GCC GTC TGC CTC ACC CGC CAC CTC ACC GCC TTC GGC GCC AGC CTC TTC GTG CCC CCA AGC 9180
3041  A   V   C   L   T   R   H   L   T   A   F   G   A   S   L   F   V   P   P   S  3060

9181 CAT GTC CGC TTT GTG TTT CCT GAG CCG ACA GCG GAT GTA AAC TAC ATC GTC ATG CTG ACA 9240
3061  H   V   R   F   V   F   P   E   P   T   A   D   V   N   Y   I   V   M   L   T  3080

9241 TGT GCT GTG TGC CTG GTG ACC TAC ATG GTC ATG GCC GCC ATC CTG CAC AAG CTG GAC CAG 9300
3081  C   A   V   C   L   V   T   Y   M   V   M   A   A   I   L   H   K   L   D   Q  3100

9301 TTG GAT GCC AGC CGG GGC CGC GCC ATC CCT TTC TGT GGG CAG CGG GGC CGC TTC AAG TAC 9360
3101  L   D   A   S   R   G   R   A   I   P   F   C   G   Q   R   G   R   F   K   Y  3120

9361 GAG ATC CTC GTC AAG ACA GGC TGG GGC CGG GGC TCA GGT ACC ACG GCC CAC GTG GGC ATC 9420
3121  E   I   L   V   K   T   G   W   G   R   G   S   G   T   T   A   H   V   G   I  3140

9421 ATG CTG TAT GGG GTG GAC AGC CGG AGC GGC CAC CGG CAC CTG GAC GGC GAC AGA GCC TTC 9480
3141  M   L   Y   G   V   D   S   R   S   G   H   R   H   L   D   G   D   R   A   F  3160

9481 CAC CGC AAC AGC CTG GAC ATC TTC CGG ATC GCC ACC CCG CAC AGC CTG GGT AGC GTG TGG 9540
3161  H   R   N   S   L   D   I   F   R   I   A   T   P   H   S   L   G   S   V   W  3180

9541 AAG ATC CGA GTG TGG CAC GAC AAC AAA GGG CTC AGC CCT GCC TGG TTC CTG CAG CAC GTC 9600
3181  K   I   R   V   W   H   D   N   K   G   L   S   P   A   W   F   L   Q   H   V  3200
```

FIG.6L

```
9601  ATC GTC AGG GAC CTG CAG ACG GCA CGC AGC GCC TTC TTC CTG GTC AAT GAC TGG CTT TCG  9660
3201   I   V   R   D   L   Q   T   A   R   S   A   F   F   L   V   N   D   W   L   S   3220

9661  GTG GAG ACG GAG GCC AAC GGG GGC CTG GTG GAG AAG GAG GTG CTG GCC GCG AGC GAC GCA  9720
3221   V   E   T   E   A   N   G   G   L   V   E   K   E   V   L   A   A   S   D   A   3240

9721  GCC CTT TTG CGC TTC CGG CGC CTG CTG GTG GCT GAG CTG CAG CGT GGC TTC TTT GAC AAG  9780
3241   A   L   L   R   F   R   R   L   L   V   A   E   L   Q   R   G   F   F   D   K   3260

9781  CAC ATC TGG CTC TCC ATA TGG GAC CGG CCG CCT CGT AGC CGT TTC ACT CGC ATC CAG AGG  9840
3261   H   I   W   L   S   I   W   D   R   P   P   R   S   R   F   T   R   I   Q   R   3280

9841  GCC ACC TGC TGC GTT CTC CTC ATC TGC CTC TTC CTG GGC GCC AAC GCC GTG TGG TAC GGG  9900
3281   A   T   C   C   V   L   L   I   C   L   F   L   G   A   N   A   V   W   Y   G   3300

9901  GCT GTT GGC GAC TCT GCC TAC AGC ACG GGG CAT GTG TCC AGG CTG AGC CCG CTG AGC GTC  9960
3301   A   V   G   D   S   A   Y   S   T   G   H   V   S   R   L   S   P   L   S   V   3320

9961  GAC ACA GTC GCT GTT GGC CTG GTG TCC AGC GTG GTT GTC TAT CCC GTC TAC CTG GCC ATC  10020
3321   D   T   V   A   V   G   L   V   S   S   V   V   V   Y   P   V   Y   L   A   I   3340

10021 CTT TTT CTC TTC CGG ATG TCC CGG AGC AAG GTG GCT GGG AGC CCG AGC CCC ACA CCT GCC  10080
3341   L   F   L   F   R   M   S   R   S   K   V   A   G   S   P   S   P   T   P   A   3360

10081 GGG CAG CAG GTG CTG GAC ATC GAC AGC TGC CTG GAC TCG TCC GTG CTG GAC AGC TCC TTC  10140
3361   G   Q   Q   V   L   D   I   D   S   C   L   D   S   S   V   L   D   S   S   F   3380

10141 CTC ACG TTC TCA GGC CTC CAC GCT GAG CAG GCC TTT GTT GGA CAG ATG AAG AGT GAC TTG  10200
3381   L   T   F   S   G   L   H   A   E   Q   A   F   V   G   Q   M   K   S   D   L   3400

10201 TTT CTG GAT GAT TCT AAG AGT CTG GTG TGC TGG CCC TCC GGC GAG GGA ACG CTC AGT TGG  10260
3401   F   L   D   D   S   K   S   L   V   C   W   P   S   G   E   G   T   L   S   W   3420

10261 CCG GAC CTG CTC AGT GAC CCG TCC ATT GTG GGT AGC AAT CTG CGG CAG CTG GCA CGG GGC  10320
3421   P   D   L   L   S   D   P   S   I   V   G   S   N   L   R   Q   L   A   R   G   3440

10321 CAG GCG GGC CAT GGG CTG GGC CCA GAG GAG GAC GGC TTC TCC CTG GCC AGC CCC TAC TCG  10380
3441   Q   A   G   H   G   L   G   P   E   E   D   G   F   S   L   A   S   P   Y   S   3460

10381 CCT GCC AAA TCC TTC TCA GCA TCA GAT GAA GAC CTG ATC CAG CAG GTC CTT GCC GAG GGG  10440
3461   P   A   K   S   F   S   A   S   D   E   D   L   I   Q   Q   V   L   A   E   G   3480
```

FIG.6M

```
10441 GTC AGC AGC CCA GCC CCT ACC CAA GAC ACC CAC ATG GAA ACG GAC CTG CTC AGC AGC CTG 10500
3481   V   S   S   P   A   P   T   Q   D   T   H   M   E   T   D   L   L   S   S   L  3500

10501 TCC AGC ACT CCT GGG GAG AAG ACA GAG ACG CTG GCG CTG CAG AGG CTG GGG GAG CTG GGG 10560
3501   S   S   T   P   G   E   K   T   E   T   L   A   L   Q   R   L   G   E   L   G  3520

10561 CCA CCC AGC CCA GGC CTG AAC TGG GAA CAG CCC CAG GCA GCG AGG CTG TCC AGG ACA GGA 10620
3521   P   P   S   P   G   L   N   W   E   Q   P   Q   A   A   R   L   S   R   T   G  3540

10621 CTG GTG GAG GGT CTG CGG AAG CGC CTG CTG CCG GCC TGG TGT GCC TCC CTG GCC CAC GGG 10680
3541   L   V   E   G   L   R   K   R   L   L   P   A   W   C   A   S   L   A   H   G  3560

10681 CTC AGC CTG CTC CTG GTG GCT GTG GCT GTG GCT GTC TCA GGG TGG GTG GGT GCG AGC TTC 10740
3561   L   S   L   L   L   V   A   V   A   V   A   V   S   G   W   V   G   A   S   F  3580

10741 CCC CCG GGC GTG AGT GTT GCG TGG CTC CTG TCC AGC AGC GCC AGC TTC CTG GCC TCA TTC 10800
3581   P   P   G   V   S   V   A   W   L   L   S   S   S   A   S   F   L   A   S   F  3600

10801 CTC GGC TGG GAG CCA CTG AAG GTC TTG CTG GAA GCC CTG TAC TTC TCA CTG GTG GCC AAG 10860
3601   L   G   W   E   P   L   K   V   L   L   E   A   L   Y   F   S   L   V   A   K  3620

10861 CGG CTG CAC CCG GAT GAA GAT GAC ACC CTG GTA GAG AGC CCG GCT GTG ACG CCT GTG AGC 10920
3621   R   L   H   P   D   E   D   D   T   L   V   E   S   P   A   V   T   P   V   S  3640

10921 GCA CGT GTG CCC CGC GTA CGG CCA CCC CAC GGC TTT GCA CTC TTC CTG GCC AAG GAA GAA 10980
3641   A   R   V   P   R   V   R   P   P   H   G   F   A   L   F   L   A   K   E   E  3660

10981 GCC CGC AAG GTC AAG AGG CTA CAT GGC ATG CTG CGG AGC CTC CTG GTG TAC ATG CTT TTT 11040
3661   A   R   K   V   K   R   L   H   G   M   L   R   S   L   L   V   Y   M   L   F  3680

11041 CTG CTG GTG ACC CTG CTG GCC AGC TAT GGG GAT GCC TCA TGC CAT GGG CAC GCC TAC CGT 11100
3681   L   L   V   T   L   L   A   S   Y   G   D   A   S   C   H   G   H   A   Y   R  3700

11101 CTG CAA AGC GCC ATC AAG CAG GAG CTG CAC AGC CGG GCC TTC CTG GCC ATC ACG CGG TCT 11160
3701   L   Q   S   A   I   K   Q   E   L   H   S   R   A   F   L   A   I   T   R   S  3720

11161 GAG GAG CTC TGG CCA TGG ATG GCC CAC GTG CTG CTG CCC TAC GTC CAC GGG AAC CAG TCC 11220
3721   E   E   L   W   P   W   M   A   H   V   L   L   P   Y   V   H   G   N   Q   S  3740

11221 AGC CCA GAG CTG GGG CCC CCA CGG CTG CGG CAG GTG CGG CTG CAG GAA GCA CTC TAC CCA 11280
3741   S   P   E   L   G   P   P   R   L   R   Q   V   R   L   Q   E   A   L   Y   P  3760
```

FIG.6N

```
11281 GAC CCT CCC GGC CCC AGG GTC CAC ACG TGC TCG GCC GCA GGA GGC TTC AGC ACC AGC GAT 11340
3761   D   P   P   G   P   R   V   H   T   C   S   A   A   G   G   F   S   T   S   D  3780

11341 TAC GAC GTT GGC TGG GAG AGT CCT CAC AAT GGC TCG GGG ACG TGG GCC TAT TCA GCC CCG 11400
3781   Y   D   V   G   W   E   S   P   H   N   G   S   G   T   W   A   Y   S   A   P  3800

11401 GAT CTG CTG GGG GCA TGG TCC TGG GGC TCC TGT GCC GTG TAT GAC AGC GGG GGC TAC GTG 11460
3801   D   L   L   G   A   W   S   W   G   S   C   A   V   Y   D   S   G   G   Y   V  3820

11461 CAG GAG CTG GGC CTG AGC CTG GAG GAG AGC CGC GAC CGG CTG CGC TTC CTG CAG CTG CAC 11520
3821   Q   E   L   G   L   S   L   E   E   S   R   D   R   L   R   F   L   Q   L   H  3840

11521 AAC TGG CTG GAC AAC AGG AGC CGC GCT GTG TTC CTG GAG CTC ACG CGC TAC AGC CCG GCC 11580
3841   N   W   L   D   N   R   S   R   A   V   F   L   E   L   T   R   Y   S   P   A  3860

11581 GTG GGG CTG CAC GCC GCC GTC ACG CTG CGC CTC GAG TTC CCG GCG GCC GGC CGC GCC CTG 11640
3861   V   G   L   H   A   A   V   T   L   R   L   E   F   P   A   A   G   R   A   L  3880

11641 GCC GCC CTC AGC GTC CGC CCC TTT GCG CTG CGC CGC CTC AGC GCG GGC CTC TCG CTG CCT 11700
3881   A   A   L   S   V   R   P   F   A   L   R   R   L   S   A   G   L   S   L   P  3900

11701 CTG CTC ACC TCG GTG TGC CTG CTG CTG TTC GCC GTG CAC TTC GCC GTG GCC GAG GCC CGT 11760
3901   L   L   T   S   V   C   L   L   L   F   A   V   H   F   A   V   A   E   A   R  3920

11761 ACT TGG CAC AGG GAA GGG CGC TGG CGC GTG CTG CGG CTC GGA GCC TGG GCG CGG TGG CTG 11820
3921   T   W   H   R   E   G   R   W   R   V   L   R   L   G   A   W   A   R   W   L  3940

11821 CTG GTG GCG CTG ACG GCG GCC ACG GCA CTG GTA CGC CTC GCC CAG CTG GGT GCC GCT GAC 11880
3941   L   V   A   L   T   A   A   T   A   L   V   R   L   A   Q   L   G   A   A   D  3960

11881 CGC CAG TGG ACC CGT TTC GTG CGC GGC CGC CCG CGC CGC TTC ACT AGC TTC GAC CAG GTG 11940
3961   R   Q   W   T   R   F   V   R   G   R   P   R   R   F   T   S   F   D   Q   V  3980

11941 GCG CAC GTG AGC TCC GCA GCC CGT GGC CTG GCG GCC TCG CTG CTC TTC CTG CTT TTG GTC 12000
3981   A   H   V   S   S   A   A   R   G   L   A   A   S   L   L   F   L   L   L   V  4000

12001 AAG GCT GCC CAG CAC GTA CGC TTC GTG CGC CAG TGG TCC GTC TTT GGC AAG ACA TTA TGC 12060
4001   K   A   A   Q   H   V   R   F   V   R   Q   W   S   V   F   G   K   T   L   C  4020

12061 CGA GCT CTG CCA GAG CTC CTG GGG GTC ACC TTG GCC TGG GTG GTG CTC GGG GTA GCC TAC 12120
4021   R   A   L   P   E   L   L   G   V   T   L   G   L   V   V   L   G   V   A   Y  4040
```

FIG.60

```
12121  GCC CAG CTG GCC ATC CTG CTC GTG TCT TCC TGT GTG GAC TCC CTC TGG AGC GTG GCC CAG  12180
4041    A   Q   L   A   I   L   L   V   S   S   C   V   D   S   L   W   S   V   A   Q   4060

12181  GCC CTG TTG GTG CTG TGC CCT GGG ACT GGG CTC TCT ACC CTG TGT CCT GCC GAG TCC TGG  12240
4061    A   L   L   V   L   C   P   G   T   G   L   S   T   L   C   P   A   E   S   W   4080

12241  CAC CTG TCA CCC CTG CTG TGT GTG GGG CTC TGG GCA CTG CGG CTG TGG GGC GCC CTA CGG  12300
4081    H   L   S   P   L   L   C   V   G   L   W   A   L   R   L   W   G   A   L   R   4100

12301  CTG GGG GCT GTT ATT CTC CGC TGG CGC TAC CAC GCC TTG CGT GGA GAG CTG TAC CGG CCG  12360
4101    L   G   A   V   I   L   R   W   R   Y   H   A   L   R   G   E   L   Y   R   P   4120

12361  GCC TGG GAG CCC CAG GAC TAC GAG ATG GTG GAG TTG TTC CTG CGC AGG CTG CGC CTC TGG  12420
4121    A   W   E   P   Q   D   Y   E   M   V   E   L   F   L   R   R   L   R   L   W   4140

12421  ATG GGC CTC AGC AAG GTC AAG GAG TTC CGC CAC AAA GTC CGC TTT GAA GGG ATG GAG CCG  12480
4141    M   G   L   S   K   V   K   E   F   R   H   K   V   R   F   E   G   M   E   P   4160

12481  CTG CCC TCT CGC TCC TCC AGG GGC TCC AAG GTA TCC CCG GAT GTG CCC CCA CCC AGC GCT  12540
4161    L   P   S   R   S   S   R   G   S   K   V   S   P   D   V   P   P   P   S   A   4180

12541  GGC TCC GAT GCC TCG CAC CCC TCC ACC TCC TCC AGC CAG CTG GAT GGG CTG AGC GTG AGC  12600
4181    G   S   D   A   S   H   P   S   T   S   S   S   Q   L   D   G   L   S   V   S   4200

12601  CTG GGC CGG CTG GGA ACA AGG TGT GAG CCT GAG CCC TCC CGC CTC CAA GCC GTG TTC GAG  12660
4201    L   G   R   L   G   T   R   C   E   P   E   P   S   R   L   Q   A   V   F   E   4220

12661  GCC CTG CTC ACC CAG TTT GAC CGA CTC AAC CAG GCC ACA GAG GAC GTC TAC CAG CTG GAG  12720
4221    A   L   L   T   Q   F   D   R   L   N   Q   A   T   E   D   V   Y   Q   L   E   4240

12721  CAG CAG CTG CAC AGC CTG CAA GGC CGC AGG AGC AGC CGG GCG CCC GCC GGA TCT TCC CGT  12780
4241    Q   Q   L   H   S   L   Q   G   R   R   S   S   R   A   P   A   G   S   S   R   4260

12781  GGC CCA TCC CCG GGC CTG CGG CCA GCA CTG CCC AGC CGC CTT GCC CGG GCC AGT CGG GGT  12840
4261    G   P   S   P   G   L   R   P   A   L   P   S   R   L   A   R   A   S   R   G   4280

12841  GTG GAC CTG GCC ACT GGC CCC AGC AGG ACA CCC CTT CGG GCC AAG AAC AAG GTC CAC CCC  12900
4281    V   D   L   A   T   G   P   S   R   T   P   L   R   A   K   N   K   V   H   P   4300

12901  AGC AGC ACT TAG
4301    S   S   T   *
```

FIG.6P

```
  1 MPPAAPARLA LALGLGLWLG ALAGGPGRGC GPCEPPCLCG PAPGAACRVN CSGRGLRTLG PALRIPADAT ELDVSHNLLR   80
             SIGNAL PEPTIDE                  LRR CYSTEINE-RICH AMINO TERMINUS
 81 ALDVGLLANL SALAELDISN NKISTLEEGI FANLFNLSEI NLSGNPFECD CGLAWLPQWA EEQQVRVVQP EAATCAGPGS  160
       LRR1              LRR2                 LRR CYSTEINE-RICH  CARBOXY TERMINUS
161 LAGQPLLGIP LLDSGCGEEY VACLPDNSSG TVAAVSFSAA HEGLLQPEAC SAFCFSTGQG LAALSEQGWC LCGAAQPSSA  240
241 SFACLSLCSG PPAPPAPTCR GPTLLQHVFP ASPGATLVGP HGPLASGQLA AFHIAAPLPV TDTRWDFGDG SAEVDAAGPA  320
                                                                                PKD1 R1
321 ASHRYVLPGR YHVTAVLALG AGSALLGTDV QVEAAPAALE LVCPSSVQSD ESLDLSIQNR GGSGLEAAYS IVALGEEPAR  400

401 AVHPLCPSDT EIFPGNGHCY RLVVEKAAWL QAQEQCQAWA GAALAMVDSP AVQRFLVSRV TRSLDVWIGF STVQGVEVGP  480
                                    C-TYPE LECTIN BINDING DOMAIN
481 APQGEAFSLE SCQNWLPGEP HPATAEHCVR LGPTGWCNTD LCSAPHSYVC ELQPGGPVQD AENLLVGAPS GDLQGPLTPL  560

561 AQQDGLSAPH EPVEVMVFPG LRLSREAFLT TAEFGTQELR RPAQLRLQVY RLLSTAGTPE NCSEPESRSP DNRTQLAPAC  640
641 MPGGRWCPGA NICLPLDASC HPQACANGCT SGPGLPGAPY ALWREFLFSV PAGPPAQYSV TLHGQDVLML PGDLVGLQHD  720
                LDL-A
721 AGPGALLHCS PAPGHPGPRA PYLSANASSW LPHLPAQLEG TWGCPACALR LLAQREQLTV LLGLRPNPGL RLPGRYEVRA  800
801 EVGNGVSRHN LSCSFDVVSP VAGLRVIYPA PRDGRLYVPT NGSALVLQVD SGANATATAR WPGGSLSARF ENVCPALVAT  880
881 FVPACPWETN DTLFSVVALP WLSEGEHVVD VVVENSASRA NLSLRVTAEE PICGLRATPS PEARVLQGVL VRYSPVVEAG  960
961 SDMVFRWTIN DKQSLTFQNV VFNVIYQSAA VFKLSLTASN HVSNVTVNYN VTVERMNRMQ GLQVSTVPAV LSPNATLALT 1040

1041 AGVLVDSAVE VAFLWTFGDG EQALHQFQPP YNESFPVPDP SVAQVLVEHN VTHTYAAPGE YLLTVLASNA FENLTQQVPV 1120
         PKD1 R2
1121 SVRASLPSVA VGVSDGVLVA GRPVTFYPHP LPSPGGVLYT WDFGDGSPVL TQSQPAANHT YASRGTYHVR LEVNNTVSGA 1200
                             PKD1 R3
1201 AAQADVRVFE ELRGLSVDMS LAVEQGAPVV VSAAVQTGDN ITWTFDMGDG TVLSGPEATV EHVYLRAQNC TVTVGAGSPA 1280
         PKD1 R4
1281 GHLARSLHVL VFVLEVLRVE PAACIPTQPD ARLTAYVTGN PAHYLFDWTF GDGSSNTTVR GCPTVTHNFT RSGTFPLALV 1360
         PKD1 R5
1361 LSSRVNRAHY FTSICVEPEV GNVTLQPERQ FVQLGDEAWL VACAWPPFPY RYTWDFGTEE AAPTRARGPE VTFIYRDPGS 1440
         PKD1 R6
1441 YLVTVTASNN ISAANDSALV EVQEPVLVTS IKVNGSLGLE LQQPYLFSAV GRGRPASYLW DLGDGGWLEG PEVTHAYNST 1520
         PKD1 R7
1521 GDFTVRVAGW NEVSRSEAWL NVTVKRRVRG LVVNASRTVV PLNGSVSFST SLEAGSDVRY SWVLCDRCTP IPGGPTISYT 1600
         PKD1 R8
1601 FRSVGTFNII VTAENEVGSA QDSIFVYVLQ LIEGLQVVGG GRYFPTNHTV QLQAVVRDGT NVSYSWTAWR DRGPALAGSG 1680
         PKD1 R9
1681 KGFSLTVLEA GTYHVQLRAT NMLGSAWADC TMDFVEPVGW LMVAASPNPA AVNTSVTLSA ELAGGSGVVY TWSLEEGLSW 1760
         PKD1 R10
1761 ETSEPFTTHS FPTPGLHLVT MTAGNPLGSA NATVEVDVQV PVSGLSIRAS EPGGSFVAAG SSVPFWGQLA TGTNVSWCWA 1840
                                                                            PKD1 R11
```

FIG. 7A

```
1841  VPGGSSKRGP HVTMVFPDAG TFSIRLNASN AVSWVSATYN LTAEEPIVGL VLWASSKVVA PGQLVHFQIL LAAGSAVTFR  1920
                                                                        PKD1 R12
1921  LQVGGANPEV LPGPRFSHSF PRVGDHVVSV RGKNHVSWAQ AQVRIVVLEA VSGLQVPNCC EPGIATGTER NFTARVQRCS  2000
                                                                                 PKD1 R13
2001  RVAYAWYFSL QKVQGDSLVI LSGRDVTYTP VAAGLLEIQV RAFNALGSEN RTLVLEVQDA VQYVALQSGP CFTNRSAQFE  2080
2081  AATSPSPRRV AYHWDFGDGS PGQDTDEPRA EHSYLRPGDY RVQVNASNLV SFFVAQATVT VQVLACREPE VDVVLPLQVL  2160
           PKD1 R14
2161  MRRSQRNYLE AHVDLRDCVT YQTEYRWEVY RTASCQRPGR PARVALPGVD VSRPRLVLPR LALPVGHYCF VFVVSFGDTP  2240
2241  LTQSIQANVT VAPERLVPII EGGSYRVWSD TRDLVLDGSE SYDPNLEDGD QTPLSFHWAC VASTQREAGG CALNFGPRCS  2320
2321  STVTIPRERL AAGVEYTFSL TVWKAGRKEE ATNQTVLIRS GRVPIVSLEC VSCKAQAVYE VSRSSYVYLE GRCLNCSSGS  2400
2401  KRGRWAARTF SNKTLVLDET TTSTGSAGMR LVLRRGVLRD GEGYTFTLTV LGRSGEEEGC ASIRLSPNRP PLGGSCRLFP  2480
2481  LGAVHALTTK VHFECTGWHD AEDAGAPLVY ALLLRRCRQG HCEEFCVYKG SLSSYGAVLP PGFRPHFEVG LAVVVQDQLG  2560
2561  AAVVALNRSL AITLPEPNGS ATGLTVWLHG LTASVLPGLL RQADPQHVIE YSLALVTVLN EYERALDVAA EPKHERQHRA  2640
2641  QIRKNITETL VSLRVHTVDD IQQIAAALAQ CMGPSRELVC RSCLKQTLHK LEAMMLILQA ETTAGTVTPT AIGDSILNIT  2720
2721  GDLIHLASSD VRAPQPSELG AESPSRMVAS QAYNLTSALM RILMRSRVLN EEPLTLAGEE IVAQGKRSDP RSLLCYGGAP  2800
2801  GPGCHFSIPE AFSGALANLS DVVQLIFLVD SNPFPFGYIS NYTVSTKVAS MAFQTQAGAQ IPIERLASER AITVKVPNNS  2880
2881  DWAARGHRSS ANSANSVVVQ PQASVGAVVT LDSSNPAAGL HLQLNYTLLD GHYLSEEPEP YLAVYLHSEP RPNEHNCSAS  2960
2961  RRIRPESLQG ADHRPYTFFI SPGSRDPAGS YHLNLSSHFR WSALQVSVGL YTSLCQYFSE EDMVWRTEGL LPLEETSPRQ  3040
3041  AVCLTRHLTA FGASLFVPPS HVRFVFPEPT ADVNYIVMLT CAVCLVTYMV MAAILHKLDQ LDASRGRAIP FCGQRGRFKY  3120
3121  EILVKTGWGR GSGTTAHVGI MLYGVDSRSG HRHLDGDRAF HRNSLDIFRI ATPHSLGSVW KIRVWHDNKG LSPAWFLQHV  3200
3201  IVRDLQTARS AFFLVNDWLS VETEANGGLV EKEVLAASDA ALLRFRRLLV AELQRGFFDK HIWLSIWDRP PRSRFTRIQR  3280
3281  ATCCVLLICL FLCANAVWYG AVGDSAYSTG HVSRLSPLSV DTVAVGLVSS VVVYPVYLAI LFLFRMSRSK VAGSPSPTPA  3360
3361  GQQVLDIDSC LDSSVLDSSF LTFSGLHAEQ AFVGQMKSDL FLDDSKSLVC WPSGEGTLSW PDLLSDPSIV GSNLRQLARG  3440
3441  QAGHGLGPEE DGFSLASPYS PAKSFSASDE DLIQQVLAEG VSSPAPTQDT HMETDLLSSL SSTPGEKTET LALQRLGELG  3520
3521  PPSPGLNWEQ PQAARLSRTG LVEGLRKRLL PAWCASLAHG LSLLLVAVAV AVSGWVGASF PPGVSVAWLL SSSASFLASF  3600
3601  LGWEPLKVLL EALYFSLVAK RLHPDEDDTL VESPAVTPVS ARVPRVRPPH GFALFLAKEE ARKVKRLHGM LRSLLVYMLF  3680
3681  LLVTLLASYG DASCHGHAYR LQSAIKQELH SRAFLAITRS EELWPMMAHV LLPYVHGNQS SPELGPPRLR QVRLQEALYP  3760
3761  DPPGPRVHTC SAAGGFSTSD YDVGWESPHN GSGTWAYSAP DLLGAWSWGS CAVYDSGGYV QELGLSLEES RDRLRFLQLH  3840
3841  NWLDNRSRAV FLELTRYSPA VGLHAAVTLR LEFPAAGRAL AALSVRPFAL RRLSAGLSLP LLTSVCLLLF AVHFAVAEAR  3920
3921  TWHREGRWRV LRLGAWARWL LVALTAATAL VRLAQLGAAD RQWTRFVRGR PRRFTSFDQV AHVSSAARGL AASLLFLLLV  4000
4001  KAAQHVRFVR QWSVFGKTLC RALPELLGVT LGLVVLGVAY AQLAILLVSS CVDSLWSVAQ ALLVLCPGTG LSTLCPAESW  4080
4081  HLSPLLCVGL WALRLWGALR LGAVILRWRY HALRGELYRP AWEPQDYEMV ELFLRRLRLW MGLSKVKEFR HKVRFEGMEP  4160
4161  LPSRSSRGSK VSPDVPPPSA GSDASHPSTS SSQLDGLSVS LGRLGTRCEP EPSRLQAVFE ALLTQFDRLN QATEDVYQLE  4240
4241  QQLHSLQGRR SSRAPAGSSR GPSPGLRPAL PSRLARASRG VDLATGPSRT PLRAKNKVHP SSTZ                   4304
```

FIG.7B

IDENTIFICATION OF POLYCYSTIC KIDNEY DISEASE GENE, DIAGNOSTICS AND TREATMENT

This is division of application Ser. No. 08/413,580 filed Mar. 30, 1995, pending, which is a continuation-in-part of application Ser. No. 08/253,524, filed Jun. 3, 1994, now abandoned.

1. INTRODUCTION

The present invention relates to the identification of the gene, referred to as the PKD1 gene, mutations in which are responsible for the vast majority of cases involving autosomal dominant polycystic kidney disease (ADPKD). The PKD1 gene, including the complete nucleotide sequence of the gene's coding region are presented. Further, the complete PKD1 gene product amino acid sequence and protein structure and antibodies directed against the PKD1 gene product are also presented. Additionally, the present invention relates to therapeutic methods and compositions for the treatment of ADPKD symptoms. Methods are also presented for the identification of compounds that modulate the level of expression of the PKD1 gene or the activity of mutant PKD1 gene product, and the evaluation and use of such compounds in the treatment of ADPKD symptoms. Still further, the present invention relates to prognostic and diagnostic, including prenatal, methods and compositions for the detection of mutant PKD1 alleles and/or abnormal levels of PKD1 gene product or gene product activity.

2. BACKGROUND OF THE INVENTION

Autosomal dominant polycystic kidney disease (ADPKD) is among the most prevalent dominant human disorders, affecting between 1 in 1,000 and 1 in 3,000 individuals worldwide (Dalgaard, O. Z., 1957, Acta. Med. Scand. 158:1–251). The major manifestation of the disorder is the progressive cystic dilation of renal tubules (Gabow, P. A., 1990, Am. J. Kidney Dis. 16:403–413), leading to renal failure in half of affected individuals by age 50.

ADPKD-associated renal cysts may enlarge to contain several liters of fluid and the kidneys usually enlarge progressively causing pain. Other abnormalities such as pain, hematuria, renal and urinary infection, renal tumors, salt and water imbalance and hypertension frequently result from the renal defect. Cystic abnormalities in other organs, including the liver, pancreas, spleen and ovaries are commonly found in ADPKD. Massive liver enlargement occasionally causes portal hypertension and hepatic failure. Cardiac valve abnormalities and an increased frequency of subarachnoid and other intracranial hemorrhage have also been observed in ADPKD. Progressive renal failure causes death in many ADPKD patients and dialysis and transplantation are frequently required to maintain life in these patients. Although end-stage renal failure usually supervenes in middle age (ADPKD is sometimes called adult polycystic kidney disease), children may occasionally have severe renal cystic disease.

Although studies of kidneys from ADPKD patients have demonstrated a number of different biochemical, structural and physiological abnormalities, the disorder's underlying causative biochemical defect remains unknown. Biochemical abnormalities which have been observed have involved proteinsorting, the distribution of cell membrane markers within renal epithelial cells, extracellular matrix, ion transport, epithelial cell turnover, and epithelial cell proliferation. The most carefully documented of these findings are abnormalities in the composition of tubular epithelial cells, and a reversal of the normal polarized distribution of cell membrane proteins, such as the $Na^+/K^+$ ATPase (Carone, F. A. et al., 1994, Lab. Inv. 70:437–448.).

As the name implies, ADPKD is inherited as an autosomal dominant disorder. Three distinct loci have been shown to cause phenotypically indistinct forms of the disease, with greater than 85–90% of disease incidence being due to mutations which map to the short arm of chromosome 16, as discussed below. Despite intensive investigation, the molecular defect responsible for ADPKD is not known.

In 1985 Reeders et al. (Reeders et al., Nature 317:542, 1985) carried out genetic linkage studies of a large number of ADPKD families and demonstrated that a gene on the short arm of chromosome 16 was mutated in most cases of ADPKD. This gene has been designated PKD1 by the Nomenclature Committee of the Human Gene Mapping Workshop and the Genome Data Base of the Welch library, John Hopkins University. Further linkage studies have identified a set of genetic markers that flank the gene-rich region containing the PKD1 gene (Reeders et al., 1988, Genomics 3:150; Somlo et al., 1992, Genomics 13:152; Breuning et al., 1990, J. Med. Genet. 27:603; Germino et al., 1990, Am. J. Hum. Genet. 46:925). These markers have been mapped by a variety of physical mapping techniques including fluorescent in situ hybridization and pulsed-field gel electrophoresis (Gillespie et al., 1990, Nucleic Acids Research 18:7071). It has been shown that the closest distal genetic marker (D16S259; on the telomeric side of the PKD1 locus) lies within 750 kb of the closest proximal genetic marker (D16S25; on the centromeric side of the PKD1 locus). The interval between the genetic markers has been cloned in a series of overlapping cosmid and bacteriophage genomic clones (Germino et al., 1992, Genomics 13:144), which contain the entire PKD1 interval, with the exception of two gaps of less than 10 kb and less than 50 kb. Restriction mapping of these clones has confirmed that the interval between the flanking genetic markers is 750 kb.

While genetic mapping studies such as these have begun to narrow the region within the human genome in which the gene responsible for ADPKD lies, there exist an estimated twenty or more genes within this 750 kb interval. Given the prevalence and severity of ADPKD, however, it is of great importance to elucidate which, if any, of these postulated genes corresponds to PKD1.

3. SUMMARY OF THE INVENTION

The present invention relates to methods and compositions for the diagnosis and treatment of autosomal dominant polycystic kidney disease (ADPKD). Specifically, a novel gene, referred to as the PKD1 gene, is described in Section 5.1. Mutations within the PKD1 gene are responsible for approximately 90% cases of ADPKD. Additionally, the PKD1 gene product, including the nucleotide sequence of the complete coding region is described in Section 5.2. Antibodies directed against the PKD1 gene product are described in Section 5.3.

Further, the present invention relates to therapeutic methods and compositions for the amelioration of ADPKD symptoms. These therapeutic techniques are described in Sections 5.9 and 5.10. Methods are additionally presented for the identification of compounds that modulate the level of expression of the PKD1 gene or the activity of PKD1 mutant gene products, and the evaluation and use of such compounds as therapeutic ADPKD treatments. Such methods are described in Section 5.8.

Still further, the present invention relates to prognostic and diagnostic, including prenatal, methods and compositions whereby the PKD1 gene and/or gene product can be used to identify individuals carrying mutant PKD1 alleles, exhibiting an abnormal level of PKD1 gene product or gene product activity. Additionally, the present invention describes methods which diagnose subjects exhibiting ADPKD symptoms. Such techniques are described in Section 5.12.

Additionally, the present invention relating to the use of PKD1 animal knockout screening assays for the identification of compounds useful for the amelioration of ADPKD symptoms.

The coding region of the PKD1 gene is complex and extensive, having a size of approximately 60 kb and containing a total of 46 exons, the sequence of which, until now, has been difficult to obtain for a number of reasons. First, the majority (approximately the first two thirds) of the PKD1 gene is duplicated several times in a transcribed fashion elsewhere in the genome, thus making it very difficult to distinguish authentic PKD1 sequence from PKD1 like sequence. Further, the PKD1 gene contains extensive repeated regions of high GC content which are not only difficult to sequence accurately, but, additionally, make the alignment of PKD1 nucleotide sequence extremely difficult. Still further, the PKD1 gene encodes a large transcript of approximately 14.5 kb in length, and evidence exists that there are alternatively spliced forms of the gene. Thus, the size of the PKD1 gene, the size and complexity of PKD1 transcript, coupled with the above-described PKD1 features made the successful sequencing of the gene and its cDNA very difficult. As described in Sections 5.1.2 and in the Example presented in Section 10, below, however, the obstacles to sequencing the PKD1 gene have now, for the first time, been overcome.

The PKD1 transcript, which is approximately 14.5 kb in length, encodes a PKD1 gene product with a derived amino acid sequence of 4304 amino acid residues. This PKD1 gene product contains at least five distinct peptide domains which are likely to be involved in protein-protein and/or protein carbohydrate interactions. Further, this PKD1 gene product shares amino acid sequence similarity with a number of extracellular matrix proteins. These features of the PKD1 gene product indicate that ADPKD is caused by a biochemical defect involving extracellular signalling and/or extracellular matrix assembly, and suggests therapeutic strategies whereby ADPKD can be treated and/or whereby ADPKD symptoms can be ameliorated.

The Examples described in Section 6 through 11, below, demonstrate the successful identification and characterization of the PKD1 gene and gene product, including the complete nucleotide sequence of the PKD1 coding region, the complete amino acid sequence, and the elucidation of the protein structure of the PKD1 gene product. Further, a ADPKD-causing mutation is identified and described.

4. DESCRIPTION OF THE FIGURES

FIG. 1. A map of the PKD1 interval showing the cosmids and bacteriophage clones covering the region (Taken from Germino et al, 1992, Genomics 13:144.) The PKD1 region as defined by flanking markers extends from D16S259 (pGGG1) to D16S25, a span of approximately 750 kb. Single-copy probes used in pulsed-field gel mapping of the region are shown above the line (pGGG1, CMM65b, etc.). C, M, P, N and B are sites for restrictions enzymes ClaI, MluI, PvuI, NotI and BssHII, respectively. Sites that cleave in genomic DNA from only some tissues are shown in parenthesis. Bold bars (a–z, aa) represent the extents of the coding regions (see Table 2). Horizontal lines 1–38 represent cosmid and phage clones spanning the PKD1 region, as shown here:

| 1 = cJC1 | 9 = cDEB11 | 17 = cKLH4 | 25 = CNK30 |
|---|---|---|---|
| 2 = cJC2 | 10 = cGGG10 | 18 = cKLH6 | 26 = λLCN1w1 |
| 3 = cDEB1 | 11 = cGGG1 | 19 = cKLH7 | 27 = λLCNw2J2 |
| 4 = CDEB4 | 12 = cGGG2 | 20 = cKLH8 | 28 = λLCNw1w3 |
| 5 - cDEB7 | 13 - cGGG3 | 21 = cKLH9 | 29 = λLCNw5.2 |
| 6 = cDEB8 | 14 - cGGG4a | 22 - cNK32 | 30 = λNK92.6w5.1 |
| 7 = cDEB9 | 15 = cGGG4b | 23 = cNK31 | 31 = λNK92.6w4.1 |
| 8 = cDEB10 | 16 = cGGG6 | 24 = cGGG8 | 32 = cNK92.6w1.3 |
| 33 = cNK92.6 | | | |
| 34 = cNK92.2 | | | |
| 35 = cNK63.7 | | | |
| 36 = cNK14 | | | |
| 37 = cCOS4 | | | |
| 38 = cCOS3 | | | |

Figure 2:
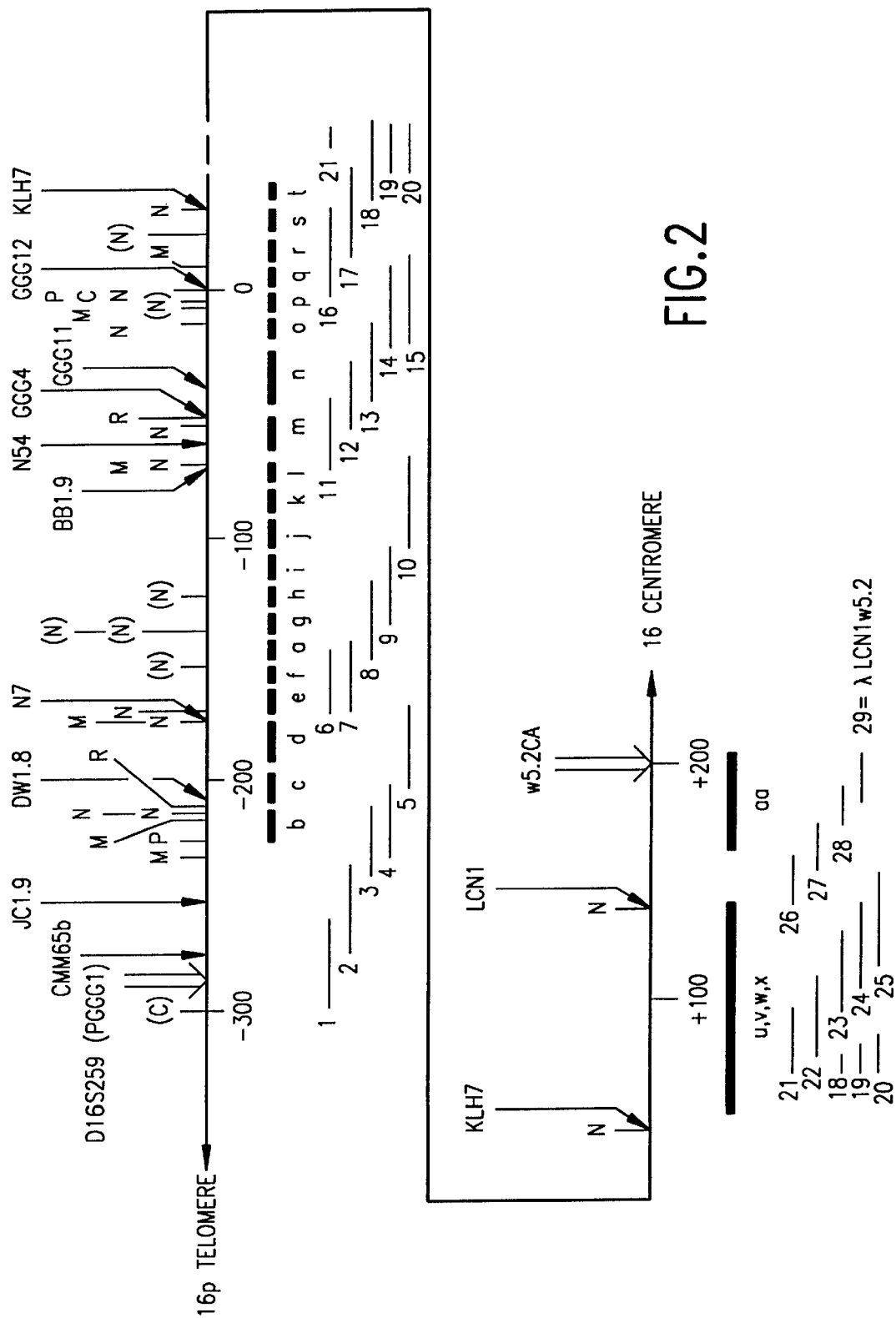

FIG. 2. A map of the PKD1 region as defined by flanking markers. The region extends from D16S259 (pGGG1) to w5.2CA, a microsatellite repeat that lies within λLCNw5.2, a span of approximately 480 kb. The labels are as for FIG. 1.

Figure 3A:
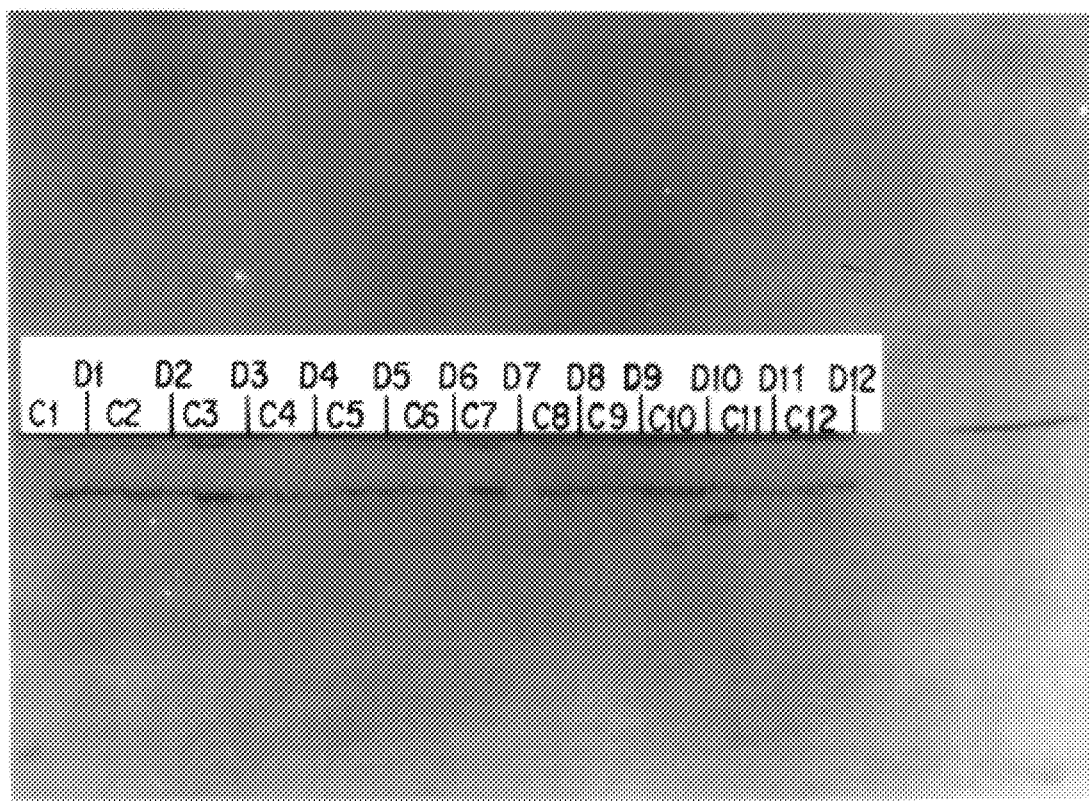
Figure 3B:
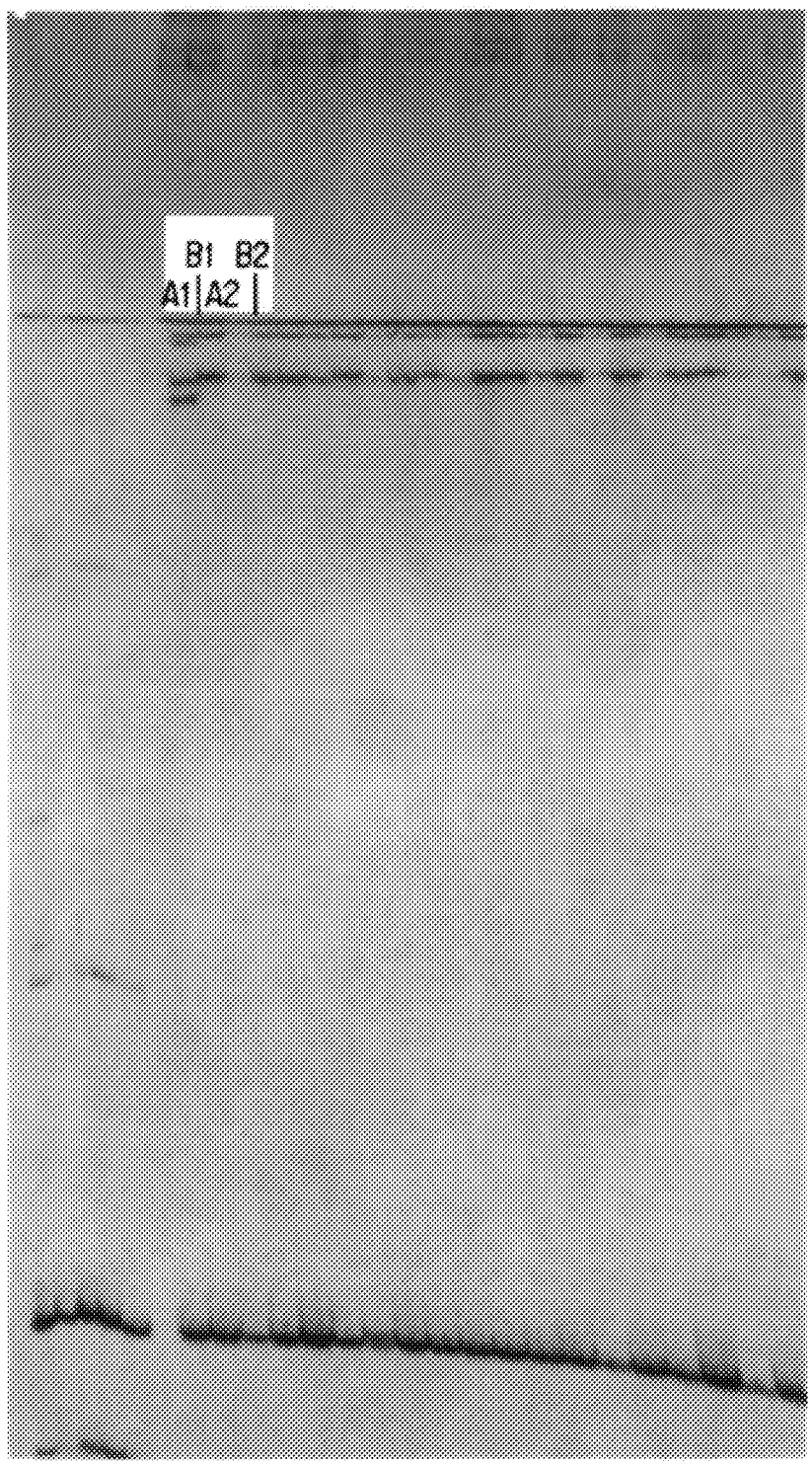

FIGS. 3A and 3B. Genomic DNA from 40 unrelated ADPKD patients was amplified by PCR for SSCP analysis. Primers F23 and R23 (See Table 1, below) were used to amplify an exon of 298 bp. Variant SSCP patterns were seen in two ADPKD patients under the following conditions. Each of the patients was heterozygous for the normal pattern and the variant pattern. The pattern seen in these patients was not seen in normal individuals. Arrow indicates non-denatured DNA.

Figure 4:
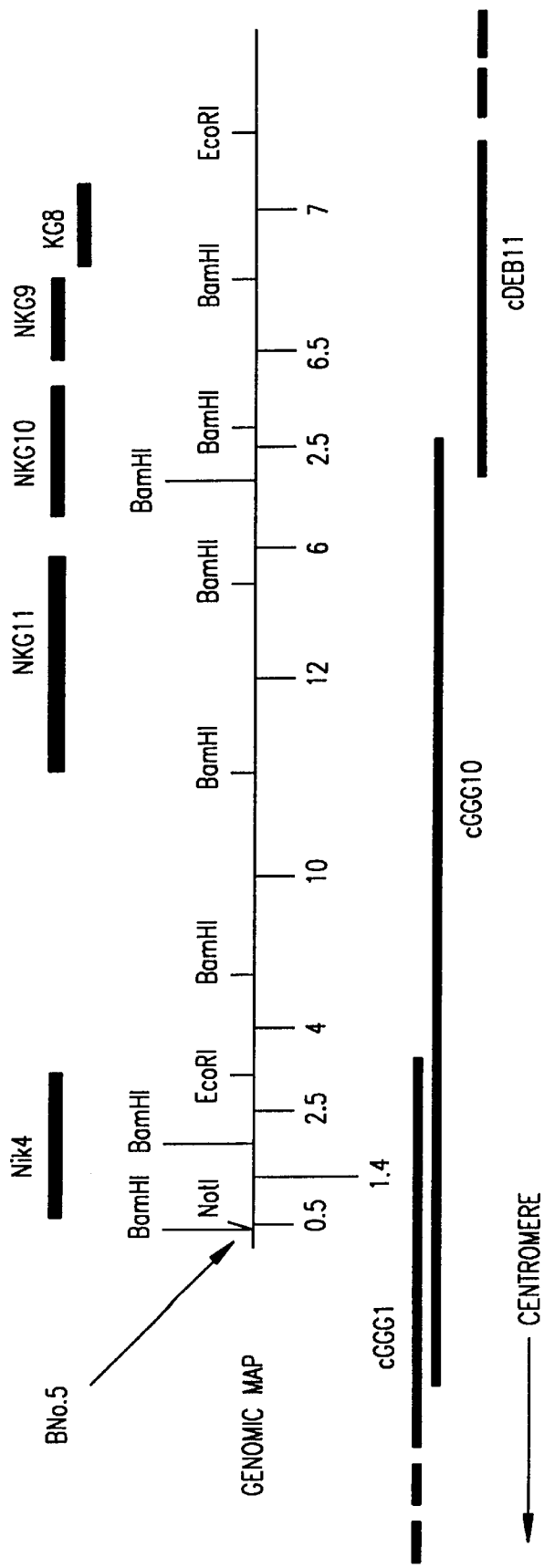

FIG. 4. A map (not to scale), derived from the cosmid contig cGGG1, cGGG10 and cDEB11, of the genomic region containing the PKD1 gene. The horizontal black bars show the positions of the three cosmids. The discontinuities in these bars indicate that the full extent of cGGG1 and cDEB11 are not shown. The map was constructea using restriction enzyme data from several enzymes. BamHI, EcoRI and NotI restriction sites are shown. The numbers below the horizontal line represent distances in kilobases between adjacent restriction sites. The PKD1 cDNA clones are shown above as grey bars. These clones hybridize to the restriction fragments shown immediately below them in the genomic map.

Figure 5A:
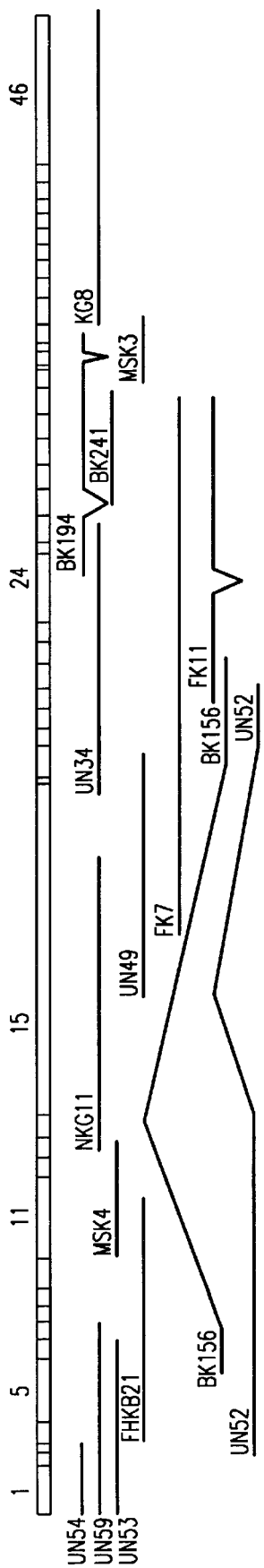

FIG. 5A. Structure of the PKD1 gene transcript. The bar at the top represents the PKD1 exon map. A total of 46 exons were identified. Below the gene transcript map are depictions of the overlapping cDNA clones, with putative alternatively spliced regions as indicated.

FIGS. 5B and 5C. PKD1 exons. This chart lists PKD1 exon sizes and indicates which cDNA clones contain nucleotide sequences corresponding to sequences present within specific exons.

FIG. 6. PKD1nucleotide and amino acid sequences. Depicted herein are, top line, the nucleotide sequence of the entire PKD1 coding region (SEQ ID NO: 1), and, bottom line, the PKD1 derived amino acid sequence (SEQ ID NO: 2), given in the one-letter amino acid code.

FIG. 7. The derived amino acid sequence of PKD1 gene product (SEQ ID NO: 2). The putative peptide domains of the PKD1 gene product are depicted underneath the amino acid sequence.

Figure 8:
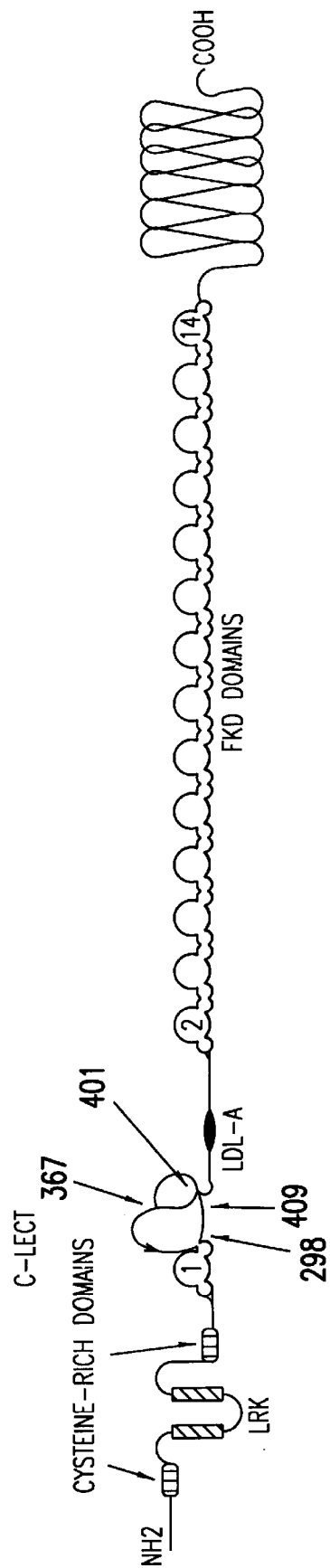

FIG. 8. A schematic representation of the PKD1 gene product, with each of its putative domains illustrated.

Figure 9:
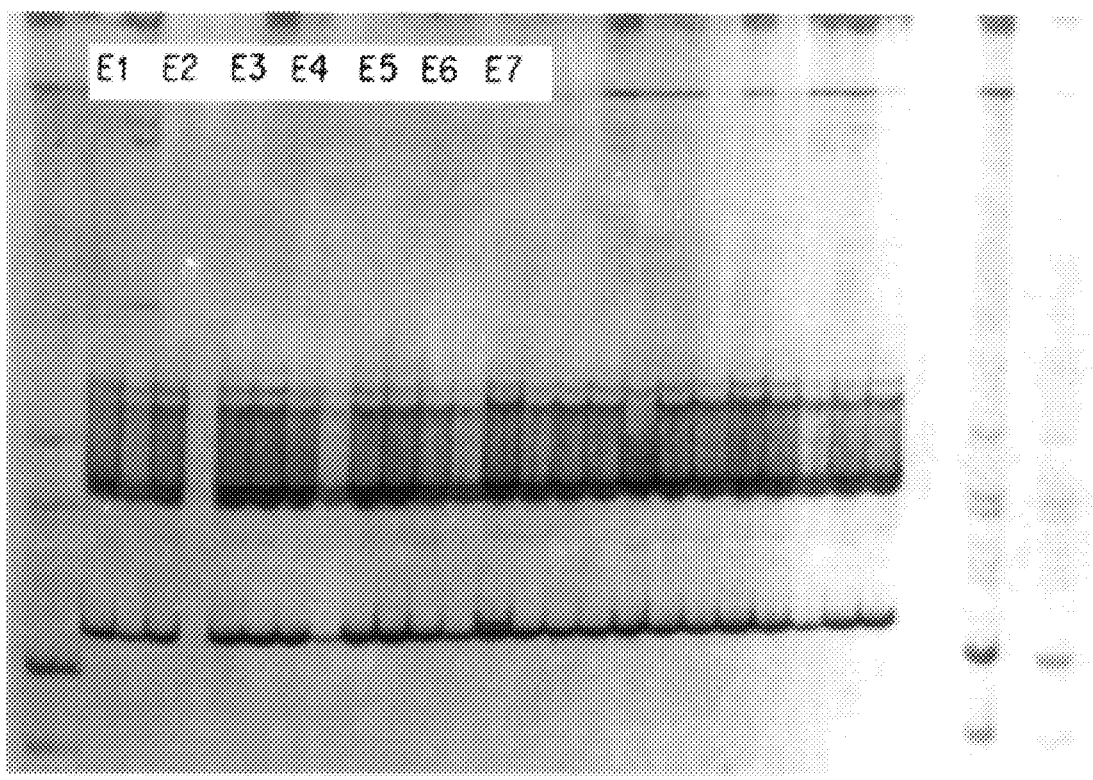

FIG. 9. SSCP analysis. Genomic DNA from a total of 60 unrelated ADPKD patients was amplified by PCR for SSCP analysis. Intronic primers F25 and Mill-1R (see Section 10.1, below) were used for amplification. A variant SSCP pattern was seen in one individual. The amplified DNA from this individual was then reamplified with the intronic primers KG8-F31 and KG8-R35 (see Section 10.1, below). Both strands of the reamplied DNA were sequenced, using F25 and Mill-1R as sequencing primers. As discussed in Section 10.2, below, sequencing revealed a C to T transition which created a stop codon at PKD1 amino acid position 765. The pattern seen in these patients was not seen in normal individuals.

5. DETAILED DESCRIPTION OF THE INVENTION

Methods and compositions for the diagnosis and treatment of (ADPKD) are described herein. Specifically, the gene, referred to herein as the PKD1 gene, in which mutations occur that are responsible for the vast majority of ADPKD cases is described. Further, the PKD1 gene product and antibodies directed against the PKD1 gene product are also presented.

Therapeutic methods and compositions are described for the treatment and amelioration of ADPKD symptoms. Further, methods for the identification of compounds that modulate the level of expression of the PKD1 gene or the activity of mutant PKD1 gene product, and the evaluation and use of such compounds in the treatment of ADPKD symptoms are also provided.

Still further, prognostic and diagnostic methods are described for the detection of mutant PKD1 alleles, of abnormal levels of PKD1 gene product or of gene product activity.

5.1. THE PKD1 GENE

The PKD1 gene, mutations in which are responsible for greater than 9 in 10 cases of ADPKD, is described herein. Specifically, the strategy followed to identify the PKD1 gene is briefly discussed, as is the strategy for obtaining the complete nucleotide sequence of the gene. Further, the PKD1 nucleotide sequence and alternative splicing features are described. Still further, nucleic acid sequences that hybridize to the PKD1 gene and which may be utilized as therapeutic ADPKD treatments and/or as part of diagnostic methods are described . Additionally, methods for the production or isolation of such PKD1 nucleic acid molecules and PKD1-hybridizing molecules are described.

5.1.1. IDENTIFICATION OF THE PKD1 GENE

Prior to the present invention, it had only been known that the physical location of the PKD1 gene within the human genome was somewhere within a 750 kb chromosomal region on the short arm of chromosome 16. As presented herein, the interval in which this gene lies has now been reduced until the specific PKD1 gene has been identified out of this large portion of DNA.

Briefly, the strategy which was followed to identify the PKD1 gene is as described herein. First, as demonstrated in the Example presented in Section 6, below, the 750 kb PKD1 interval was first substantially narrowed to approximately 460 kb, via genetic linkage studies. Next, as shown in the Example presented in Section 7, below, a maximum of 27 transcriptional units (TUs) were identified within this approximately 460 kb PKD1 interval. The total length of these TUs was approximately 300 kb. Thus, the region containing the PKD1 coding region was narrowed down to a region of approximately 300 kb.

Next, as presented in the Example shown in Section 9, below, a Northern analysis was conducted with mRNA isolated from normal and ADPKD patient kidney tissue, in order to attempt to compare the pattern of ADPKD pathology to the expression profile of the TUs within the PKD1 interval. One of the TUs, Nik9, was eliminated by such an analysis, which indicated undetectable expression in the kidney and liver.

In addition, as demonstrated in the Example presented in Section 9, below, a systematic search was undertaken using several independent techniques, including Southern analysis SSCP, DGGE (denaturing gradient gel electrophoresi)s and direct sequencing of coding sequences, to detect mutations in ADPKD patients within the TUs of the PKD1 region. By conducting such a mutation screen, greater than 80% of the combined identified coding sequences in the PKD1 region were excluded, thus further substantially narrowing down the region in which the PKD1 gene could lie. The screen was initially performed on individual genes until virtually all the coding sequences were shown to be devoid of mutations. The focus on possible PKD1 candidates was further honed by the recognition that PKD1 demonstrated one of the highest new mutation rates known for human diseases. Based on this observation, it was hypothesized that either the PKD1 gene contained a highly mutable site or that the gene presented a large number of potential mutation sites, each mutable at a regular frequency. Such a hypothesis is supported by the absence of substantial linkage disequilibrium among selected population groups. Further, this hypothesis predicted that if the PKD1 gene was a small transcript, it should contain a highly mutable element.

Trinucleotide repeat expansion represent one of the major sources for dominant mutations such as the ADPKD-causing mutations which arise in the PKD1 gene. A systematic search for such highly mutable trinucleotide repeats was conducted within the TUs in the remaining region wherein PKD1 could lie, but no such repeats were identified.

The only other explanation for the high mutational prevalence is that the gene is physically large and presents a large target for mutations. Of the TUs, nik823, within the potential PKD1 region that had not been excluded by other means, only two were of a size that could potentially support such a high mutation rate. As demonstrated in the Example presented, below, in Section 9, a search for ADPKD correlative mutations within one of these TUs failed to identify any such mutations, causing it to be excluded as a candidate PKD1 gene. Ultimately, as demonstrated in the Example presented in Section 10, below, one of these polymorphisms has been shown to be a de novo mutation which is predicted to lead to the production of a truncated PKD1 protein in the affected individual, These finding are highly suggestive, if not proof, that the identified gene is the PKD1 gene.

Thus, the examples presented below in Sections 6 through 11 demonstrate, through a variety of techniques, the genetic and molecular characterization of the PKD1 region, and ultimately demonstrate that the PKD1 gene, dominant mutations in which cause ADPKD, has been identified.

5.1.2. SEQUENCING OF THE PKD1 GENE

As discussed, below, in Section 5.1.3, the nucleotide sequence of the entire coding region of the PKD1 gene has now successfully been isolated and sequenced. In order to achieve this goal, however, a number of PKD1-specific impediments had to be overcome. The strategy for obtaining the PKD1 gene sequence is discussed, briefly, in this Section. The Example presented below, in Section 11, discusses this sequencing strategy in more detail.

First, the PKD1 gene is very large, (approximately 60 kb), as is the PKD1 transcript, being approximately 14.5 kb in length. In addition to this size difficulty, approximately two thirds of the 5' end of the gene is duplicated several times in a highly similar, transcribed fashion elsewhere in the human genome (Germino, G. G. et al., 1992, Genomics 13:144–151; European Chromosome 16 Tuberous Sclerosis Consortium, 1993, Cell 75:1305–1315).

The near-identity of the sequence of cDNA derived from PKD1 and from the PKD1-like duplications made the likelihood of piecing together a full-length PKD1 transcript by merely screening cDNA libraries via hybridization very low. Such a screening method would be as likely to identify transcripts originating from both the PKD1-like duplicated regions as from the authentic PKD1 locus. In fact, if each of the duplicated loci were as transcriptionally active as the authentic PKD1 locus, the representation of authentic PKD1 cDNA clones among the total positive clones, would be very low.

Thus, a strategy was developed for obtaining the authentic PKD1 sequence which included, first, a plan for obtaining the highest quality of both genomic sequence spanning the duplicated region as well as obtaining duplicate coverage of cDNA sequence spanning the expected length of the PKD1 transcript; second, to compare the cDNA sequences to the genomic sequence spanning the duplicated region, thus identifying PKD1 exons; and, finally, to assemble the identified exons into a full-length PKD1 coding sequence. The isolation of both PKD1 genomic and cDNA sequence and, further, the aligning of such sequences, however, proved to be very difficult.

PKD1 genomic DNA (which totals approximately 60 kb) proved to be particularly difficult to characterize for a number of reasons. First, portions of PKD1 genomic DNA (specifically, regions within cosmid cGGG10) tended to be preferentially subcloned. For example, screens for trinucleotide repeats in the cGGG10 cosmid identified one CCT-positive subclone in a Sau3A-generated library of cGGG10 sublcones. This region was, however, vastly underrepresented in both the Sau3A library (i.e., approximately 1 clone out of over 10,000) and subsequent sheared cosmid libraries (in which no such clones were isolated). A plasmid sublone containing the region, G13, proved difficult to grow and to sequence. Sequence analysis of the clone revealed a highly monotonous series of purines (A and G). Such sequences are thought to make the clone difficult to stably propagate in bacteria. Thus, in order to ascertain the level of representation of the cosmid, it was necessary to construct a detailed physical map of the cGGG10 cosmid.

Second, genomic sequence within the PKD1 region is very GC-rich (approximately 70%), and forms extensive, stable secondary structures. These PKD1 genomic DNA features made the task of obtaining accurate nucleotide sequence very difficult. Several alternative sequencing conditions, including different polymerases, melting conditions, polymerization conditons and combinations thereof had to be utilized before such sequence was obtained. However, even when reliable nucleotide sequence became available, the extensive amount of repeated sequences within the genomic made the aligning of sequence information very difficult. It became necessary for accurate aligning of sequences, therefore, to use the fine physical map which had been created earlier.

The sequencing of PKD1 cDNA also presented a number of PKD1-specific difficulties. First, the 14 kb size of the transcript made it impossible to isolate a single cDNA clone containg the entire PKD1 transcript. Overlapping partial cDNA clones, therefore, had to be obtained in order to piece together an entire sequence. Partial cDNA clones were obtained by sequencing the ends of one cDNA insert, synthesizing probes using this sequence, and obtaining overlapping cDNA clones by their hybridization to such probes. Second, the PKD1 gene was poorly represented in renal cDNA libraries, and, in fact, its expression appeared to be low in a number of tissues, making the isolation of PKD1 cDNA clones especially difficult.

5.1.3. THE PKD1 GENE

Described, herein is the complete nucleotide sequence of the extensive PKD1 gene coding region. Further, PKD1 alternative splicing features are discussed, below.

The coding region of the PKD1 gene is complex and extensive, containing a total of 46 exons and producing a transcript of approximately 14 kb in length. FIG. 5A depicts the structure of the PKD1 gene transcript. A total of 46 exons were identified within the PKD1 gene. Additionally, sequence analysis from a number of cDNA clones reveals that the gene may have alternatively spliced forms. FIG. 5B shows a table of exons, listing exon sizes and indicating which cDNA clones contain nucleotide sequences corresponding to sequences present within specific exons.

FIG. 6 depicts the PKD1 nucleotide sequence. Specifically, the top line of FIG. 6 shows the nucleotide sequence of the entire PKD1 coding region (SEQ ID NO: 1).

The term "PKD1 gene", as used herein, refers to (a) the nucleotide sequence depicted in FIG. 6 (SEQ ID NO: 1); (b) any DNA sequence that hybridizes to the complement of the nucleotide sequence depicted in FIG. 6 (SEQ ID NO: 1), under highly stringent conditions, e.g., hybridization to filter-bound DNA in 0.5M $NaHPO_4$, 7% sodium dodecyl sulfate (SDS), 1 mM EDTA at 65°, and washing in 0.1× SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and which encodes a gene product functionally equivalent to the PKD1 gene product (SEQ ID NO: 2) depicted in FIG. 6; and/or (c) any DNA sequence that hybridizes to the complement of the nucleotide sequence depicted in FIG. 6 (SEQ ID NO: 1) under less stringent conditions, such as moderately stringent conditions, e.g., washing in 0.2×SSC/0.1% SDS at 42° C. (Ausubel et al., 1989, supra), yet which still encodes a gene product functionally equivalent to the PKD1 gene product depicted in FIG. 6 (SEQ ID NO: 2).

The term "functionally equivalent" as used herein can refer to: 1) a gene product or peptide having the biological function of the PKD1 gene product depicted in FIG. 6 and/or the biological function of a PKD1 peptide domain, as depicted in FIGS. 7 and 8; 2) a gene product containing at least one PKD1 peptide domain as depicted in FIGS. 7 and 8; or 3) a gene product having an 80% overall amino acid residue similarity to the PKD1 gene product depicted in FIG. 6. The term "functionally equivalent gene" as used herein can further refer a nucleotide sequence which encodes a gene product of 1, 2 or 3, as described earlier in this paragraph.

The invention also includes nucleic acid molecules, preferably DNA molecules, that hybridize to, and are therefore the complements of, the DNA sequences (a) through (c), in the preceding paragraph. Such hybridization conditions may be highly stringent or less highly stringent, as described above. In instances wherein the nucleic acid molecules are oligonucleotides ("oligos"), highy stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as PKD1 antisense molecules, useful, for example, in PKD1 gene regulation and/or as antisense primers in amplification reactions of PKD1 nucleic acid sequences. Further, such sequences may be used as part of ribozyme and/or triple helix sequences, also useful for PKD gene regulation. Still further, such molecules may be used as components of diagnostic methods whereby the level of PKD1 transcript may be deduced and/or the presence of an ADPKD-causing allele may be detected. Further, such sequences can be used to screen for and identify PKD1 homologs from, for example, other species.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. For example, such regulatory elements may include CMV immediate early gene regulatory sequences, SV40 early or late promoter sequences on adenovirus, lac system, trp system, tac system or the trc system sequences. The invention includes fragments of any of the DNA sequences disclosed herein.

In addition to the PKD1 gene sequences described above, homologs of the PKD1 gene of the invention, as may, for example be present in other, non-human species, may be identified and isolated by molecular biological techniques well known in the art and, for example, labelled probes of small as 12 bp. Further, mutant PKD1 alleles and additional normal alleles of the human PKD1 gene of the invention, may be identified using such techniques. Still further, there may exist genes at other genetic loci within the human genome that encode proteins which have extensive homology to one or more domains of the PKD1 gene product. Such genes may also be identified via such techniques.

For example, such a previously unknown PKD1-type gene sequence may be isolated by performing a polymerase chain reaction (PCR; the experimental embodiment set forth by Mullis, K. B., 1987, U.S. Pat. No. 4,683,202) using two degenerate oligonucleotide primer pools designed on the basis of amino acid sequences within the PKD1 gene described herein (see, e.g. FIG. 6, SEQ ID NO: 2). The template for the reaction may be cDNA obtained by reverse transcription of mRNA prepared from human or non-human cell lines or tissue known to express a PKD1 allele or PKD1 homologue. The PCR product may be subcloned and sequenced to insure that the amplified sequences represent the sequences of a PKD1 or a PKD-like nucleic acid sequence. The PCR fragment may then be used to isolate a full length PKD1 cDNA clone by radioactively labeling the amplified fragment and screening a bacteriophage cDNA library. Alternatively, the labeled fragment may be used to screen a genomic library. For a review of cloning strategies which may be used, see e.g., Maniatis, 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

5.2. THE PKD1 GENE PRODUCT

The PKD1 gene products of the invention include the PKD1 gene product encoded by the PKD1 nucleotide sequence depicted in FIG. 6 (SEQ ID NO: 2). The PKD1 gene product shown in FIG. 6 is a protein of 4304 amino acid residues, with a predicted mass of approximately 467 kiodaltons. This PKD1 gene product contains as least five distinct peptide domains which are likely to be involved in protein-protein and/or protein-carbohydrate interactions. Further, this PKD1 gene product shares amino acid sequence similarity with a number of extracellular matrix proteins. (See FIGS. 7 and 8, which list the PKD1 gene product domains.) The PKD1 gene product domains are more fully described below, in the Example presented in Section 10.

In addition, PKD1 gene products that represent functionally equivalent gene products are within the scope of the invention. "Functionally equivalent" as used herein is as defined in Section 5.1, above. Such an equivalent PKD1 gene product may contain deletions, additions or substitutions of amino acid residues within the PKD1 sequence encoded by the PKD1 gene sequences described, above, in Section 5.1.3, but which result in a silent change thus producing a functionally equivalent PKD1 protein. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine, glycine, analine, asparagine, glutamine, serine, threonine, phenylalanine and tyrosine. As used herein, a functionally equivalent PKD1 refers to a protein that exhibits substantially the same biological activity as the PKD1 gene product encoded by the PKD1 gene sequences described in Section 5.1.1, above.

PKD1 gene products and peptides substantially similar to the PKD1 gene product encoded by the PKD1 gene sequences described in Section 5.1, above, which cause ADPKD symptoms are also intended to fall within the scope of the invention. Such gene products and peptides may include dominant mutant PKD1 gene products, or PKD1 gene products functionally equivalent to such mutant PKD1 gene products. By "functionally equivalent mutant PKD1 gene product" it is meant PKD1-like proteins that exhibit a biological activity substantially similar to the activity demonstrated by dominant mutant PKD1 gene products.

The PKD1 wild type or mutant protein may be purified from natural sources, as discussed in Section 5.2.1, below, or may, alternatively, be chemically synthesized or recombinantly expressed, as discussed in Section 5.2.2, below.

5.2.1 PKD1 PROTEIN PURIFICATION METHODS

The PKD1 protein may be substantially purified from natural sources (e.g., purified from cells) using protein separation techniques well known in the art. "Substantially purified" signifies purified away from at least about 90% (on a weight basis), and from at least about 99% of other proteins, glycoproteins, and other macromolecules normally found in such natural sources.

Such purification techniques may include, but are not limited to ammonium sulfate precipitation, molecular sieve chromatography, and/or ion exchange chromatography. Alternatively, or additionally, the PKD1 gene product may be purified by immunoaffinity chromatography using an immunoabsorbent column to which an antibody is immobilized which is capable of binding the PKD1 gene product. Such an antibody may be monoclonal or polyclonal in origin. If the PKD1 gene product is specifically glycosylated, the glycosylation pattern may be utilized as part of a purification scheme via, for example, lectin chromatography.

The cellular sources from which the PKD1 gene product may be purified may include, but are not limited to, those cells that are expected, by Northern and/or Western blot analysis, to express the PKD1 gene. Preferably, such cellular sources are renal tubular epithelial cells, bilary duct cells, skeletal muscle cells, whole brain cells, lung alveolar epithelial cell, and placental cells.

One or more forms of the PKD1 gene product may be secreted out of the cell, i.e., may be extracellular. Such extracellular forms of the PKD1 gene product may preferably be purified from whole tissue rather than cells, utilizing any of the techniques described above. Preferable tissue includes, but is not limited to those tissues than contain cell types such as those described above. Alternatively, PKD1 expressing cells such as those described above may be grown in cell culture, under conditions well known to those of skill in the art. The PKD1 gene product may then be purified from the cell media using any of the techniques discussed above.

5.2.2. PKD1 PROTEIN SYNTHESIS AND EXPRESSION METHODS

Methods for the chemical synthesis of polypeptides (e.g, gene products) or fragments thereof, are well-known to those of ordinary skill in the art, e.g., peptides can be synthesized by solid phase techniques, cleaved from the resin and purified by preparative high performance liquid chromatography (see, e.g., Creighton, 1983, Proteins: Structures and Molecular Principles, W. H. Freeman & Co., N.Y., pp. 50–60). The composition of the synthetic peptides may be confirmed by amino acid analysis or sequencing; e.g., using the Edman degradation procedure (see e.g., Creighton, 1983, supra at pp. 34–49). Thus, the PKD1 protein may be chemically synthesized in whole or in part.

The PKD1 protein may additionally be produced by recombinant DNA technology using the PKD1 nucleotide sequences as described, above, in Section 5.1, coupled with techniques well known in the art. Thus, methods for preparing the PKD1 polypeptides and peptides of the invention by expressing nucleic acid encoding PKD1 sequences are described herein. Methods which are well known to those skilled in the art can be used to construct expression vectors containing PKD1 protein coding sequences and appropriate transcriptional/translational control signals. These methods include, for example, in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y., both of which are incorporated by reference herein in their entirety. Alternatively, RNA capable of encoding PKD1 protein sequences may be chemically synthesized using, for example, automated or semi-automated synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the PKD1 coding sequences of the invention. Such host-expression systems represent vehicles by which the coding sequences of interest may be produced and subsequently purified, but also represent cells which may, when transformed or transfected with the appropriate nucleotide coding sequences, exhibit the PKD1 protein of the invention in situ. These include but are not limited to microorganisms such as bacteria (e.g., *E. coli, B. subtilis*) transformed with recombinant bacteriophage DNA, plasmid DNA or cosmid DNA expression vectors containing PKD1 protein coding sequences; yeast (e.g., Saccharomyces, Pichia) transformed with recombinant yeast expression vectors containing the PKD1 protein coding sequences; insect cell systems infected with recombinant virus expression vectors (e.g., baculovirus) containing the PKD1 protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the PKD1 protein coding sequences coding sequence; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g, the adenovirus late promoter; the vaccinia virus 7.5K promoter).

In bacterial systems, a number of expression vectors may be advantageously selected depending upon the use intended for the PKD1 protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited to, the *E. coli* expression vector pUR278 (Ruther et al., 1983, EMBO J. 2:1791), in which the PKD1 protein coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned PKD1 protein can be released from the GST moiety.

In an insect system, *Autographa californica* nuclear olyhedrosis virus (AcNPV) is used as a vector to express foreign genes. The virus grows in *Spodoptera frugiperda* cells. The PKD1 coding sequence may be cloned individually into non-ressential regions (for example the polyhedrin gene) of the virus and placed under control of an AcNPV promoter (for example the polyhedrin promoter). Successful insertion of PKD1 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983, J. Viol. 46:584; Smith, U.S. Pat. No. 4,215,051).

In mammalian host cells, a number of viral-based expression systems may be utilized. In cases where an adenovirus is used as an expression vector, the PKD1 coding sequence or interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing PKD1 protein in infected hosts (e.g., See Logan & Shenk, 1984, Proc. Natl. Acad. Sci. USA 81:3655–3659). Specific initiation signals may also be required for efficient translation of inserted PKD1 coding sequences. These signals include the ATG initiation codon and adjacent sequences. In cases where an entire PKD1 gene, including its own initiation codon and adjacent sequences, is inserted into the appropriate expression vector, no additional translational control signals may be needed. However, in cases where only a portion of the PKD1 coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, etc.

For long-term, high-yield production of recombinant proteins, stable expression is preferred. For example, cell lines which stably express the PKD1 protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the PKD1 protein. Such engineered cell lines may be particularly useful in screening and evaluation of compounds that affect the endogenous activity of the PKD1 protein.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cells 22:817) genes can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 15 78:1527); gpt, which confers resistance to mycophenolic acid Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

Whether produced by molecular cloning methods or by, chemical synthetic methods, the amino acid sequence of the PKD1 protein which may be used in the assays of the invention need not be identical to the amino acid sequence encoded by the PKD1 gene reported herein. The PKD1 proteins or peptides used may comprise altered sequences in which amino acid residues are deleted, added, or substituted, while still resulting in a gene product functionally equivalent to the PKD1 gene product. "Functionally equivalent", as utilized herein, is as defined, above, in Section 5.1, and is additionally defined to refer to peptides capable of interacting with other cellular or extracellular molecules in a manner substantially similar to the way in which the corresponding portion of the endogenous PKD1 gene product would.

For example, functionally equivalent amino acid residues may be substituted for residues within the sequence resulting in a change of amino acid sequence. Such substitutes may be selected from other members of the class (i.e., non-polar, positively charged or negatively charged) to which the amino acid belongs; e.g., the nonpolar (hydrophobic) amino acids include alanine, leucine, isoleucine, valine, proline, phenylalanine, tryptophan, and methionine; the polar neutral amino acids include glycine, serine, threonine, cysteine, tyrosine, asparagine, and glutamine; the positively charged (basic) amino acids include arginine, lysine, and histidine; the negatively charged (acidic) amino acids include aspartic and glutamic acid.

When used as a component in the assay systems described herein, the PKD1 gene product or peptide (e.g., gene product fragment) may be labeled, either directly or indirectly, to facilitate detection of a complex formed between the PKD1 gene product and a test substance. Any of a variety of suitable labeling systems may be used including but not limited to radioisotopes such as $^{125}$I; enzyme labelling systems that generate a detectable colorimetric signal or light when exposed to substrate; and fluorescent labels.

Where recombinant DNA technology is used to produce the PKD1 protein for the assay systems described herein, it may be advantageous to engineer fusion proteins that can facilitate labeling, immobilization and/or detection. For example, the coding sequence of the viral or host cell protein can be fused to that of a heterologous protein that has enzyme activity or serves as an enzyme substrate in order to facilitate labeling and detection. The fusion constructs should be designed so that the heterologous component of the fusion product does not interfere with binding of the host cell and viral protein.

Indirect labeling involves the use of a third protein, such as a labeled antibody, which specifically binds to one of the binding partners, i.e., either the PKD1 protein or its binding partner used in the assay. Such antibodies include but are not limited to polyclonal, monoclonal, chimeric, single chain, Fab fragments and fragments produced by an Fab expression library.

5.3. ANTIBODIES REACTIVE WITH PKD1 GENE PRODUCT

Described herein are methods for the production of antibodies capable of specifically recognizing one or more PKD1 gene product epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Such antibodies may be used, for example, in the detection of PKD1 gene product in a biological sample, or, alternatively, as a method for the inhibition of abnormal PKD1 activity. Thus, such antibodies may be utilized as part of ADPKD treatment methods, and/or may be used as part of diagnostic techniques whereby patients may be tested for abnormal levels of PKD1 gene product, or for the presence of abnormal forms of the PKD1 protein.

For the production of antibodies to PKD1, various host animals may be immunized by injection with PKD1 protein, or a portion thereof. Such host animals may include but are not limited to, rabbits, mice, and rats. Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacteriumparvum.

Polyclonal antibodies are heterogeneous populations of antibody molecules derived from the sera of animals immunized with an antigen, such as PKD1, or an antigenic functional derivative thereof. For the production of polyclonal antibodies, host animals such as those described above, may be immunized by injection with PKD1 protein supplemented with adjuvants as also described above.

Monoclonal antibodies which are substantially homogeneous populations of antibodies to a particular antigen, may be obtained by any technique which provides for the production of antibody molecules by continuous cell lines in culture. These include, but are not limited to, the hybridoma technique of Kohler and Milstein (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class, including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454; U.S. Pat. No. 4,816,567, which is incorported by reference herein in its entirety) by splicing the genes from a mouse antibody molecule of appropriate antigen specificity together with genes from a human antibody molecule of appropriate biological activity can be used. A chimeric antibody is a molecule in which different portions are derived from different animal species, such as those having a murine variable region and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce PKD1-single chain antibodies. Single chain antibodies are formed by linking the heavy and light chain fragment of the Fv region via an amino acid bridge, resulting in a single chain polypeptide.

Further, PKD1-humanized monoclonal antibodies may be produced using standard techniques (see, for example, U.S. Pat. No. 5,225,539, which is incorporated herein by reference in its entirety).

Antibody fragments which recognize specific epitopes may be generated by known techniques. For example, such fragments include but are not limited to the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.4. SCREENING ASSAYS FOR COMPOUNDS THAT INTERACT WITH THE PKD1 GENE PRODUCT

The following assays are designed to identify compounds that bind to the PKD1 gene product; other cellular proteins that interact with the PKD1 gene product; and compounds that interfere with the interaction of the PKD1 product with other cellular proteins.

Compounds identified via assays such as those described herein may be useful, for example, in elaborating the biological function of the PKD1 gene product, and for ameliorating ADPKD symptoms caused by mutations within the PKD1 gene. In instances whereby a mutation with the PKD1 gene causes a lower level of expression, and therefore results in an overall lower level of PKD1 activity in a cell or tissue, compounds that interact with the PKD1 gene product may include ones which accentuate or amplify the activity of the bound PKD1 protein. Thus, such compounds would bring about an effective increase in the level of PKD1 activity, thus ameliorating ADPKD symptoms. In instances whereby mutations with the PKD1 gene cause aberrant PKD1 proteins to be made which have a deleterious effect that leads to ADPKD, compounds that bind PKDI protein may be identified that inhibit the activity of the bound PKD1 protein.

This decrease in the aberrant PKD1 activity can therefore, serve to ameliorate ADPKD symptoms. Assays for testing the effectiveness of compounds, identified by, for example, techniques such as those described in this Section are discussed, below, in Section 5.5.

5.5. IN VITRO SCREENING ASSAYS FOR COMPOUNDS THAT BIND TO THE PKD1 PROTEIN

In vitro systems may be designed to identify compounds capable of binding the PKD1 gene of the invention. Such compounds may include, but are not limited to, peptides made of D-and/or L-configuration amino acids (in, for example, the form of random peptide libraries; see Lam, K. S. et al., 1991, Nature 354:82–84), phosphopeptides (in, for example, the form of random or partially degenerate, directed phosphopeptide libraries; see, for example, Songyang, Z. et al., 1993, Cell 72:767–778), antibodies, and small or large organic or inorganic molecules. Compounds identified may be useful, for example, in modulating the activity of PKD1 proteins, preferably mutant PKD1 proteins, may be useful in elaborating the biological function of the PKD1 protein, may be utilized in screens for identifying compounds that disrupt normal PKD1 interactions, or may in themselves disrupt such interactions.

The principle of the assays used to identify compounds that bind to the PKD1 protein involves preparing a reaction mixture of the PKD1 protein and the test compound under conditions and for a time sufficient to allow the two components to interact and bind, thus forming a complex which can be removed and/or detected in the reaction mixture. These assays can be conducted in a heterogeneous or homogeneous format. Heterogeneous assays involve anchoring PKD1 or the test substance onto a solid phase and detecting PKD1 test substance complexes anchored on the solid phase at the end of the reaction. In homogeneous assays, the entire reaction is carried out in a liquid phase. In either approach, the order of addition of reactants can be varied to obtain different information about the compounds being tested.

In a heterogeneous assay system, the PKD1 protein may be anchored onto a solid surface, and the test substance, which is not anchored, is labeled, either directly or indirectly. In practice, microtiter plates are conveniently utilized. The anchored component may be immobilized by non-covalent or covalent attachments. Non-covalent attachment may be accomplished simply by coating the solid surface with a solution of the protein and drying. Alternatively, an immobilized antibody, preferably a monoclonal antibody, specific for the protein may be used to anchor the protein to the solid surface. The surfaces may be prepared in advance and stored.

In order to conduct the assay, the labeled component is added to the coated surface containing the anchored component. After the reaction is complete, unreacted components are removed (e.g., by washing) under conditions such that any complexes formed will remain immobilized on-the solid surface. The detection of complexes anchored on the solid surface can be accomplished in a number of ways. Where the labeled compound is pre-labeled, the detection of label immobilized on the surface indicates that complexes were formed. Where the labeled component is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody).

Alternatively, a heterogenous reaction can be conducted in a liquid phase, the reaction products separated from unreacted components, and complexes detected; e.g., using an immobilized antibody specific for PKD1 or the test substance to anchor any complexes formed in solution, and a labeled antibody specific for the other binding partner to detect anchored complexes.

In an alternate embodiment of the invention, a homogeneous assay can be used. In this approach, a preformed complex of the PKD1 protein and a known binding partner is prepared in which one of the components is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will result in the generation of a signal above background.

5.6. ASSAYS FOR CELLULAR PROTEINS THAT INTERACT WITH PKD1 PROTEIN

Any method suitable for detecting protein-protein interactions may be employed for identifying novel PKD1-cellular or extracellular protein interactions. For example, some traditional methods which may be employed are co-immunoprecipitation, crosslinking and copurification through gradients or chromatographic columns. Additionally, methods which result in the simultaneous identification of the genes coding for the protein interacting with a target protein may be employed. These methods include, for example, probing expression libraries with labeled target protein, using this protein in a manner similar to antibody probing of $\lambda$gt11 libraries.

One such method which detects protein interactions in vivo, the yeast two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to one test protein "X" and the other consists of the activator protein's activation domain fused to another test protein "Y". Thus, either "X" or "Y" in this system may be wild type or mutant PKD1, while the other may be a test protein or peptide. The plasmids are transformed into a strain of the yeast *Saccharomyces cerevisiae* that contains a reporter gene (e.g., lacZ) whose regulatory region contains the activator's binding sites. Either hybrid protein alone cannot activate transcription of the reporter gene, the DNA-binding domain hybrid because it does not provide activation function and the activation domain hybrid because it cannot localize to the activator's binding sites. Interaction of the two proteins reconstitutes the functional activator protein and results in expression of the reporter gene, which is detected by an assay for the reporter gene product.

The two-hybrid system or related methodology can be used to screen activation domain libraries for proteins that interact with a PKD1 protein. Total genomic or cDNA sequences are fused to the DNA encoding an activation domain. This library and a plasmid encoding a hybrid of the PKD1 protein fused to the DNA-binding domain are cotransformed into a yeast reporter strain, and the resulting transformants are screened for those that express the reporter gene. These colonies are purified and the plasmids responsible for reporter gene expression are isolated. DNA sequencing is then used to identify the proteins encoded by the library plasmids.

For example, and not by way of limitation, the PKD1 gene can be cloned into a vector such that it is translationally fused to the DNA encoding the DNA-binding domain of the GAL4 protein. A cDNA library of the cell line from which proteins that interact with PKD1 are to be detected can be made using methods routinely practiced in the art. According to this particular system, for example, the cDNA fragments can be inserted into a vector such that they are translationally fused to the activation domain of GAL4. This library can be co-transformed along with the PKD1-GAL4 DNA binding domain fusion plasmid into a yeast strain which contains a lacZ gene driven by a promoter which contains GAL4 activation sequences. A cDNA encoded protein, fused to GAL4 activation domain, that interacts with PKD1 will reconstitute an active GAL4 protein and thereby drive expression of the lacZ gene. Colonies which express lacZ can be detected by their blue color in the presence of X-gal. The cDNA can then be extracted from strains derived from these and used to produce and isolate the PKD1 -interacting protein using techniques routinely practiced in the art.

5.7. ASSAYS FOR COMPOUNDS THAT INTERFERE WITH PKD1/CELLULAR PROTEIN INTERACTION

The PKD1 protein of the invention may, in vivo, interact with one or more cellular or extracellular proteins. Such cellular proteins are referred to herein as "binding partners". Compounds that disrupt such interactions may be useful in regulating the activity of the PKD1 protein, especially mutant PKD1 proteins. Such compounds may include, but are not limited to molecules such as antibodies, peptides, and the like described in Section 5.2.1. above.

In instances whereby ADPKD symptoms are caused by a mutation within the PKD1 gene which produces PKD1 gene products having aberrant, gain-of-function activity, compounds identified that disrupt such interactions may, therefore inhibit the aberrant PKD1 activity. Preferably, compounds may be identified which disrupt the interaction of mutant PKD1 gene products with cellular or extracellular proteins, but do not substantially effect the interactions of the normal PKD1 protein. Such compounds may be identified by comparing the effectiveness of a compound to disrupt interactions in an assay containing normal PKD1 protein to that of an assay containing mutant PKD1 protein.

The basic principle of the assay systems used to identify compounds that interfere with the interaction between the PKD1 protein, preferably mutant PKD1 protein, and its cellular or extracellular protein binding partner or partners involves preparing a reaction mixture containing the PKD1 protein and the binding partner under conditions and for a time sufficient to allow the two proteins to interact and bind, thus forming a complex. In order to test a compound for inhibitory activity, the reaction is conducted in the presence and absence of the test compound, i.e., the test compound may be initially included in the reaction mixture, or added at a time subsequent to the addition of PKD1 and its cellular or extracellular binding partner; controls are incubated without the test compound or with a placebo. The formation of any complexes between the PKD1 protein and the cellular or extracellular binding partner is then detected. The formation of a complex in the control reaction, but not in the reaction mixture containing the test compound indicates that the compound interferes with the interaction of the PKD1 protein and the interactive protein. As noted above, complex formation within reaction mixtures containing the test compound and normal PKD1 protein may also be compared to complex formation within reaction mixtures containing the test compound and mutant PKD1 protein. This comparison may be important in those cases wherein it is desirable to identify compounds that disrupt interactions of mutant but not normal PKD1 proteins.

The assay for compounds that interfere with the interaction of the binding partners can be conducted in a heterogeneous or homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the PKD1 protein and interactive cellular or extracellular protein. On the other hand, test compounds that disrupt preformed complexes, e.c. compounds with higher binding constants that displace one of the binding partners from the complex, can be tested by adding the test compound to the reaction mixture after complexes have been formed. The various formats are described briefly below.

In a heterogeneous assay system, one binding partner, e.g., either the PKD1 protein or the interactive cellular or extracellular protein, is anchored onto a solid surface, and its binding partner, which is not anchored, is labeled, either directly or indirectly. In practice, microtiter plates are conveniently utilized. The anchored species may be immobilized by non-covalent or covalent attachments. Non-covalent attachment may be accomplished simply by coating the solid surface with a solution of the protein and drying. Alternatively, an immobilized antibody specific for the protein may be used to anchor the protein to the solid surface. The surfaces may be prepared in advance and stored.

In order to conduct the assay, the binding partner of the immobilized species is added to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the PKD1 protein and the interactive cellular or extracellular protein is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will result in the generation of a signal above background. In this way, test substances which disrupt PKD1 protein-cellular or extracellular protein interaction can be identified.

In a particular embodiment, the PKD1 protein can be prepared for immobilization using recombinant DNA techniques described in Section 5.1.2.2, supra. For example, the PKD1 coding region can be fused to the glutathione-S-transferase (GST) gene using the fusion vector pGEX-5X-1, in such a manner that its binding activity is maintained in the resulting fusion protein. The interactive cellular or extracellular protein can be purified and used to raise a monoclonal antibody, using methods routinely practiced in the art and described above. This antibody can be labeled with the radioactive isotope $^{125}$I, for example, by methods routinely practiced in the art. In a heterogeneous assay, e.g., the GST-PKD1 fusion protein can be anchored to glutathione-agarose beads. The interactive cellular or extracellular protein can then be added in the presence or absence of the test compound in a manner that allows interaction and binding to occur. At the end of the reaction period, unbound material can be washed away, and the labeled monoclonal antibody can be added to the system and allowed to bind to the complexed binding partners. The interaction between the PKD1 protein and the interactive cellular or extracellular protein can be detected by measuring the amount of radioactivity that remains associated with the glutathione-agarose beads. A successful inhibition of the interaction by the test compound will result in a decrease in measured radioactivity.

Alternatively, the GST-PKD1 fusion protein and the interactive cellular or extracellular protein can be mixed together in liquid in the absence of the solid glutathioneagarose beads. The test compound can be added either during or after the binding partners are allowed to interact. This Mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the PKD1 protein and the interactive cellular or extracellular protein, respectively, in place of one or both of the full length proteins. Any number of methods routinely practiced in the art can be used to identify and isolate the protein's binding site. These methods include, but are not limited to, mutagenesis of one of the genes encoding the proteins and screening for disruption of binding in a co-immunoprecipitation assay. Compensating mutations in the PKD1 gene can be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the for the cellular or extracellular protein is obtained, short gene segments can be engineered to express peptide fragments of the protein, which can then be tested for binding activity and purified or synthesized.

For example, and not by way of limitation, PKD1 can be anchored to a solid material as described above in this section by making a GST-PKD1 fusion protein and allowing it to bind to glutathione agarose beads. The interactive cellular protein can be labeled with a radioactive isotope, such as $^{35}$S, and cleaved with a proteolytic enzyme such as trypsin. Cleavage products can then be added to the anchored GST-PKD1 fusion protein and allowed to bind. After washing away unbound peptides, labeled bound material, representing the cellular or extracellular protein binding domain, can be eluted, purified, and analyzed for amino acid sequence by methods described in Section 5.1.2.2, supra. Peptides so identified can be produced synthetically or fused to appropriate facilitative proteins using recombinant DNA technology, as described in Section 5.1.2.2, supra.

5.8. ASSAYS FOR ADKPD-INHIBITORY ACTIVITY

Any of the binding compounds, including but not limited to, compounds such as those identified in the foregoing assay systems may be tested for anti-ADPKD activity. ADPKD, an autosomal dominant disorder, may involve underexpression of a wild-type PKD1 allele, or expression of a PKD1 gene product that exhibits little or no PKD1 activity. In such an instance, even though the PKD1 gene product is present, the overall level of normal PKD1 gene product present is insufficient and leads to ADPKD symptoms. As such, "anti-ADPKD activity", as used herein, may refer to a increase in the level of expression of the normal PKD1 gene product, to levels wherein ADPKD symptoms are ameliorated. Additionally, the term may refer to an increase in the level of normal PKD1 activity in the cell, to levels wherein ADPKD symptoms are ameliorated.

Alternatively, ADPKD may be caused by the production of an aberrant mutant form of the PKD1 protein, which either interferes with the normal allele product or introduces a novel function into the cell, which then leads to the mutant phenotype. For example, a mutant PKD1 protein may compete with the wild type protein for the binding of a substance required to relay a signal inside or outside of a cell. Circumstances such as these are referred to as "gain of function" mutations. It is possible that different mechanisms could be occurring in different patients which can lead to mutant phenotypic variations.

"Anti-ADPKD activity", as used herein, may refer to a decrease in the level and/or activity of such a mutant PKD1 protein so that symptoms of PKD1 are ameliorated.

Cell-based and animal model-based assays for the identification of compounds exhibiting anti-ADPKD activity are described below.

5.8.1. CELL BASED ASSAYS

Cells that contain and express mutant PKD1 gene sequences which encode mutant PKD1 protein, and thus exhibit cellular phenotypes associated with ADPKD, may be utilized to identify compounds that possess anti-ADPKD activity. Such cells may include cell lines consisting of naturally occurring or engineered cells which express mutant or express both normal and mutant PKD1 gene products. Such cells include, but are not limited to renal epithelial cells, including primary and immortalized human renal tubular cells, MDCK cells, LLPCK1 cells, and human renal carcinoma cells.

Cells, such as those described above, which exhibit ADPKD-like cellular phenotypes, may be exposed to a compound suspected of exhibiting anti-ADPKD activity at a sufficient concentration and for a time sufficient to elicit such anti-ADPKD1 activity in the exposed cells. After exposure, the cells are examined to determine whether one or more of the ADPKD-like cellular phenotypes has been altered to resemble a more wild type, non-ADPKD phenotype.

Among the cellular phenotypes which may be followed in the above assays are differences in the apical/basolateral distribution of membrane proteins. For example, normal (i.e., non-ADPKD) renal tubular cells in situ and in culture under defined conditions have a characteristic pattern of apical/basolateral distribution of cell surface markers. ADPKD renal cells, by contrast, exhibit a distribution pattern that reflects a partially reversed apical/basolateral polarity relative to the normal distribution. For example, sodium-potassium ATPase is found on the basolateral membranes of renal epithelial cells but is found on the apical surface of ADPKD epithelial cells, both in cystic epithelia in vivo and in ADPKD cells in culture (Wilson, et al., 1991, Am. J. Physiol. 260:F420–F430). Among the other markers which exhibit an alteration in polarity in normal versus ADPKD affected cells are the EGF receptor, which is normally located basolaterally, but in ADPKD cells is mislocated to the apical surface. Such a apical/basolateral marker distribution phenotype may be followed, for example, by standard immunohistology techniques using antibodies specific to the marker(s) of interest in conjunction with procedures that are well known to those of skill in the art.

Additionally, assays for the function of the PKD1 gene product can, for example, include a measure of extracellular matrix (ECM) components, such as proteoglycans, laminin, fibronectin and the like, in that studies in both ADPKD and in rat models of acquired cystic disease (Carone, F. A. et al., 1989, Kidney International 35:1034–1040) have shown alterations in such components. Thus, any compound which serves to create an extracellular matrix environment which more fully mimics the normal ECM should be considered as a candidate for testing for an ability to ameliorate ADPKD symptoms.

5.8.2 ANIMAL MODEL ASSAYS

The ability of a compound, such as those identified in the foregoing binding assays, to prevent or inhibit disease may be assessed in animal models for ADPKD. Several naturally-occurring mutations for renal cystic disease have been found in animals. While these are not perfect models of ADPKD, they provide test systems for assaying the effects of compounds that interact with PKD1 proteins. Of these models, the Han: SPRD rat model is the only autosomal dominant example. Such a model is well known to those of skill in the art. See, for example, Kaspareit-Rittinghausen et al., 1989, Vet. Path. 26:195. In addition, several recessive models exist (Reeders, S., 1992, Nature Genetics 1:235).

Additionally, animal models exhibiting ADPKD-like symptoms may be engineered by utilizing PKD1 sequences such as those described, above, in Section 5.1, in conjunction with techniques for producing transgenic animals that are well known to those of skill in the art.

Animals of any species, including, but not limited to, mice, rats, rabbits, guinea pigs, pigs, micro-pigs, goats, and non-human primates, e.g., baboons, squirrels, monkeys, and chimpanzees may be used to generate such ADPKD animal models.

In instances wherein the PKD1 mutation leading to ADPKD symptoms causes a drop in the level of PKD1 protein or causes an ineffective PKD1 protein to be made (i.e., the PKD1 mutation is a dominant loss-of-function mutation) various strategies may be utilized to generate animal models exhibiting ADPKD-like symptoms. For example, PKD1 knockout animals, such as mice, may be generated and used to screen for compounds which exhibit an ability to ameliorate ADPKD systems. Animals may be generated whose cells contain one inactivated copy of a PKD1-homologue. In such a strategy, human PKD1 gene sequences may be used to identify a PKD1 homologue within the animal of interest; utilizing techniques described, above, in Section 5.1. Once such a PKD1 homologue has been identified, well-known techniques such as those described, below, in Section 5.8.2.1. may be utilized to disrupt and inactivate the endogenous PKD1 homolog, and further, to produce animals which are heterozygous for such an inactivated PKD1 homolog. Such animals may then be observed for the development of ADPKD-like symptoms.

In instances wherein a PKD1 mutation causes a PKD1 protein having an aberrant PKD1 activity which leads to ADPKD symptoms (i.e., the PKD1 mutation is a dominant gain-of-function mutation) strategies such as those now described may be utilized to generate ADPKD animal models. First, for example, a human PKD1 gene sequence containing such a gain-of-function PKD1 mutation, and encoding such an aberrant PKD1 protein, may be introduced into the genome of the animal of interest by utilizing well known techniques such as those described, below, in Section 5.8.2.1. Such a PKD1 nucleic acid sequence must be controlled by a regulatory nucleic acid sequence which allows the mutant human PKD1 sequence to be expressed in the cells, preferably kidney cells, of the animal of interest. The human PKD1 regulatory promoter/enhancer sequences may be sufficient for such expression. Alternatively, the mutant PKD1 gene sequences may be controlled by regulatory sequences endogenous to the animal of interest, or by any other regulatory sequences which are effective in bringing about the expression of the mutant human PKD1 sequences in the animal cells of interest.

Expression of the mutant human PKD1 gene may be assayed, for example, by standard Northern analysis, and the production of the mutant human PKD1 gene product may be assayed by, for example, detecting its presence by utilizing techniques whereby binding of an antibody directed against the mutant human PKD1 gene product is detected. Those animals found to express the mutant human PKD1 gene product may then be observed for the development of ADPKD-like symptoms.

Alternatively, animal models of ADPKD may be produced by engineering animals containing mutations within one copy of their endogenous PKD1-homologue which correspond to gain-of-function mutations within the human PKD1 gene. Utilizing such a strategy, a PKD1 homologue may be identified and cloned from the animal of interest, using techniques such as those described, above, in Section 5.1. One or more gain-of-function mutations may be engineered into such a PKD1 homolog which correspond to gain-of-function mutations within the human PKD1 gene. By "corresponding", it is meant that the mutant gene product produced by such an engineered PKD1 homologue will exhibit an aberrant PKD1 activity which is substantially similar to that exhibited by the mutant human PKD1 protein.

The engineered PKD1 homologue may then be introduced into the genome of the animal of interest, using techniques such as those described, below, in Section 5.8.2.1. Because the mutation introduced into the engineered PKD1 homologue is expected to be a dominant gain-of-function mutation, integration into the genome need not be via homologous recombination, although such a route is preferred.

Once transgenic animals have been generated, the expression of the mutant PKD1 homolog gene and protein may be assayed utilizing standard techniques, such as Northern and/or Western analyses. Animals expressing mutant PKD1 homolog proteins within the animals of interest, in cells or tissues, preferably kidney, of interest, the transgenic animals may be observed for the development of ADPKD-like symptoms.

Any of the ADPKD animal models described herein may be used to test compounds for an ability to ameliorate ADPKD symptoms.

In addition, as described in detail in Section 5.11 infra, such animal models can be used to determine the $LD_{50}$ and the $ED_{50}$ in animal subjects, and such data can be used to determine the in vivo efficacy of potential ADPKD treatments.

5.8.2.1 PRODUCTION OF PKD1 TRANSGENIC ANIMALS

Any technique known in the art may be used to introduce a PKD1 gene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety).

When it is desired that the PKD1 transgene be integrated into the chromosomal site of the endogenous PKD1, gene targeting is preferred. Briefly, when such a technique is to be utilized, vectors containing some nucleotide sequences homologous to the endogenous PKD1 gene of interest are designed for the purpose of integrating, via homologous recombination with chromosomal sequences, into and disrupting the function of, the nucleotide sequence of the endogenous PKD1 gene.

Once the PKD1 founder animals are produced, they may be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound PKD1 transgenics that express the PKD1 transgene at higher levels because of the effects of additive expression of each PKD1 transgene; crossing of heterozygous transgenic animals to produce animals homozygous for a given integration site in order to both augment expression and eliminate the possible need for screening of animals by DNA analysis; crossing of separate homozygous lines to produce compound heterozygous or homozygous lines; breeding animals to different inbred genetic backgrounds so as to examine effects of modifying alleles on expression of the PKD1 transgene and the development of ADPKD-like symptoms. One such approach is to cross the PKD1 founder animals with a wild type strain to produce an Fl generation that exhibits ADPKD symptoms, such as the development of polycystic kidneys. The F1 generation may then be inbred in order to develop a homozygous line, if it is found that homozygous PKD1 transgenic animals are viable.

The present invention provides for transgenic animals that carry the transgene in all their cells, as well as animals which carry the transgene in some, but not all their cells, i.e., mosaic animals. The transgene may be integrated as a single transgene or in concatamers, e.g., head-to-head tandems or head-to-tail tandems.

5.8.2.2. SELECTION AND CHARACTERIZATION OF THE PKD1 TRANSGENIC ANIMALS

The PKD1 transgenic animals that are produced in accordance with the procedures detailed, above, in Section 5.8.2.1., should be screened and evaluated to select those animals which may be used as suitable animal models for ADPKD.

Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of PKD1-expressing tissue, kidney tissue, for example, may be evaluated immunocytochemically using antibodies specific for the PKD1 transgene gene product.

The PKD1 transgenic animals that express PKD1 mRNA or gene product (detected immunocytochemically, using antibodies directed against PKD1 tag epitopes) at easily detectable levels should then be further evaluated histopathologically to identify those animals which display characteristic ADPKD-like symptoms. Such transgenic animals serve as suitable model systems for ADPKD.

5.8.2.3. USES OF THE PKD1 ANIMAL MODELS

The PKD1 animal models of the invention may be used as model systems for ADPKD disorder andtor to generate cell lines that can be used as cell culture models for this disorder.

The PKD1 transgenic animal model systems for ADPKD may be used as a test substrate to identify-drugs, pharmaceuticals, therapies and interventions which may be effective in treating such a disorder. Potential therapeutic agents may be tested by systemic or local administration. Suitable routes may include oral, rectal, or intestinal administration; parenteral delivery, including intramuscular, subcutaneous, intramedullary injections, as well as intrathecal, direct intraventricular, intravenous, intraperitoneal, intranasal, or intraocular injections, to name a few. The response of the animals to the treatment may be monitored by assessing the reversal of disorders associated with ADPKD. With regard to intervention, any treatments which reverse any aspect of ADPKD-like symptoms should be considered as candidates for human ADPKD therapeutic intervention. However, treatments or regimens which reverse the constellation of pathologies associated with any of these disorders may be preferred. Dosages of test agents may be determined by deriving dose-response curves, as discussed in Section 5.11, below.

In an alternate embodiment, the PKD1 transgenic animals of the invention may be used to derive a cell line which may be used as a test substrate in culture, to identify agents that ameliorate ADPKD-like symptoms. While primary cultures derived from the PKD1 transgenic animals of the invention may be utilized, the generation of continuous cell lines is preferred. For examples of techniques which may be used to derive a-continuous cell line from the transgenic animals, see Small et al., 1985, Mol. Cell Biol. 5:642–648.

5.9. COMPOUNDS THAT INHIBIT EXPRESSION, SYNTHESIS OR ACTIVITY OF MUTANT PKD1 ACTIVITY

As discussed above, dominant mutations in the PKD1 gene that cause ADPKD may act as gain-of-function mutations which produce a form of the PKD1 protein which exhibits an aberrant activity that leads to the formation of ADPKD symptoms. A variety of techniques may be utilized to inhibit the expression, synthesis, or activity of such mutant PKD1 genes and gene products (i.e., proteins).

For example, compounds such as those identified through assays described, above, in Section 5.4, which exhibit inhibitory activity, may be used in accordance with the invention to ameliorate ADPKD symptoms. Such molecules may include, but are not limited, to small and large organic molecules, peptides, and antibodies. Inhibitory antibody techniques are described, below, in Section 5.9.2.

Further, antisense and ribozyme molecules which inhibit expression of the PKD1 gene, preferably the mutant PKD1 gene, may also be used to inhibit the aberrant PKD1 activity. Such techniques are described, below, in Section 5.9.1. Still further, as described, below, in Section 5.9.1, triple helix molecules may be utilized in inhibiting the aberrant PKD1 activity.

5.9.1. INHIBITORY ANTISENSE, RIBOZYME AND TRIPLE HELIX APPROACHES

Among the compounds which may exhibit anti-ADPKD activity are antisense, ribozyme, and triple helix molecules. Such molecules may be designed to reduce or inhibit mutant PKD1 activity. Techniques for the production and use of such molecules are well known to those of skill in the art.

Antisense RNA and DNA molecules act to directly block the translation of mRNA by binding to targeted mRNA and preventing protein translation. With respect to antisense DNA, oligodeoxyribonucleotides derived from the translation initiation site, e.g., between the −10 and +10 regions of the PKD1 nucleotide sequence of interest, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. The composition of ribozyme molecules must include one or more sequences complementary to the target PKD1 mRNA, preferably the mutant PKD1 mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding PKD1, preferably mutant PKD1 proteins.

Specific ribozyme cleavage sites within any potential RNA target are initially identified by scanning the target molecule for ribozyme cleavage sites which include the following sequence: GUA, GUU and GUC. Once identified, short RNA sequences of between 15 and ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays.

Nucleic acid molecules to be used in triplex helix formation should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molrcules may be chosen that are purine-rich, for example, contain a stretch of guanidine residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with one strand of a duplex first and then the other, eliminating the necessity for a sizeable stretch of either purines or pyrimidines to be present on one strand of a duplex.

It is possible that the antisense, ribozyme, and/or triple helix molecules described herein may reduce or inhibit the translation of mRNA produced by both normal and mutant PKD1 alleles. In order to ensure that substantial normal levels of PKD1 activity are maintained in the cell, nucleic acid molecules that encode and express PKD1 polypeptides exhibiting normal PKD1 activity may be introduced into cells which do not contain sequences susceptible to whatever antisense, ribozyme, or triple helix treatments. Such sequences may be introduced via gene therapy methods such as those described, below, in Section 5.5. Alternatively, it may be preferable to coadminister normal PKD1 protein into the cell or tissue in order to maintain the requisite level of cellular or tissue PKD1 activity.

Antisense RNA and DNA molecules, ribozyme molecules and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include, but are not limited to, the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

5.9.2. ANTIBODIES THAT REACT WITH PKD1 GENE PRODUCT

Antibodies that are both specific for mutant PKD1 gene product and interfere with its activity may be used. Such antibodies may be generated using standard techniques described in Section 5.3., supra, against the proteins themselves or against peptides corresponding to the binding domains of the proteins. Such antibodies include but are not limited to polyclonal, monoclonal, Fab fragments, F(ab')$_2$ fragments, single chain antibodies, chimeric antibodies, humanized antibodies etc.

The PKD1 protein appears to be an extracellular protein. Therefore, any of the administration techniques described, below in Section 5.11 which are appropriate for peptide administration may be utilized to effectively administer inhibitory PKD1 antibodies to their site of action.

5.10 METHODS FOR RESTORING PKD1 ACTIVITY

As discussed above, dominant mutations in the PKD1 gene that cause ADPKD may lower the level of expression of the PKD1 gene or; alternatively, may cause inactive or substantially inactive PKD1 proteins to be formed. In either instance, the result is an overall lower level of normal PKD1 activity in the tissues or cells in which PKD1 is normally expressed. This lower level of PKD1 activity, then, leads to ADPKD symptoms. Thus, such PKD1 mutations represent dominant loss-of-function mutations. Described in this Section are methods whereby the level of normal PKD1 activity may be increased to levels wherein ADPKD symptoms are ameliorated.

For example, normal PKD1 protein, at a level sufficient to ameliorate ADPKD symptoms may be administered to a patient exhibiting such symptoms. Any of the techniques discussed, below, in Section 5.11, may be utilized for such administration. One of skill in the art will readily know how to determine the concentration of effective, non-toxic doses of the normal PKD1 protein, utilizing techniques such as those described, below, in Section 5.11.

Additionally, DNA sequences encoding normal PKD1 protein may be directly administered to a patient exhibiting ADPKD symptoms, at a concentration sufficient to produce a level of PKD1 protein such that ADPKD symptoms are ameliorated. Any of the techniques discussed, below, in Section 5.11, which achieve intracellular administration of compounds, such as, for example, liposome administration, may be utilized for the administration of such DNA molecules. The DNA molecules may be produced, for example, by recombinant techniques such as those described, above, in Section 5.1, and its subsections.

Further, patients with these types of mutations may be treated by gene replacement therapy. A copy of the normal PKD1 gene or a part of the gene that directs the production of a normal PKD1 protein with the function of the PKD1 protein may be inserted into cells, renal cells, for example, using viral or non-viral vectors which include, but are not limited to vectors derived from, for example, retroviruses, vaccinia virus, adeno-associated virus, herpes viruses, bovine papilloma virus or additional, non-viral vectors, such as plasmids. In addition, techniques frequently employed by those skilled in the art for introducing DNA into mammalian cells may be utilized. For example, methods including but not limited to electroporation, DEAE-dektran mediated DNA transfer, DNA guns, liposomes, direct injection, and the like may be utilized to transfer recombinant vectors into host cells. Alternatively, the DNA may be transferred into cells through conjugation to proteins that are normally targeted to the inside of a cell. For example, the DNA may be conjugated to viral proteins that normally target viral particles into the targeted host cell. Additionally, techniques such as those described in Sections 5.1 and 5.2 and their subsections, above, may be utilized for the introduction of normal PKD1 gene sequences into human cells.

The PKD1 gene is very large and, further, encodes a very large, approximately 14 kb, transcript. Additionally, the PKD1 gene product is large, having 4304 amino acids, with a molecular weight of about 467 kD. It is possible, therefore, that the introduction of the entire PKD1 coding region may be cumbersome and potentially inefficient as a gene therapy approach. However, because the entire PKD1 gene product may not be necessary to avoid the appearance of ADPKD symptoms, the use of a "minigene" therapy approach (see, e.g., Ragot, T. et al., 1993, Nature 3:647; Dunckley, M. G. et al., 1993, Hum. Mol. Genet. 2:717–723) can serve to ameliorate such DPKD symptoms.

Such a minigene system comprises the use of a portion of the PKD1 coding region which encodes a partial, yet active or substantially active PKD1 gene product. As used herein, "substantially active" signifies that the gene product serves to ameliorate ADPKD symptoms. Thus, the minigene system utilizes only that portion of the normal PKD1 gene which encodes a portion of the PKD1 gene product capable of ameliorating ADPKD symptoms, and may, therefore represent an effective and even more efficient ADPKD gene therapy than full-length gene therapy approaches. Such a minigene can be inserted into cells and utilized via the procedures described, above, for full-length gene replacement. The cells into which the PKD1 minigene are to be introduced are, preferably, those cells, such as renal cells7 which are affected by ADPKD. Alternatively, any suitable cell can be transfected with a PKD1 minigene as long as the minigene is expressed in a sustained, stable fashion and produces a gene product that ameliorates ADPKD symptoms. Regulatory sequences by which such a PKD1 minigene can be successfully expressed will vary depending upon the cell into which the minigene is introduced. The skilled artisan will be aware of appropriate regulatory sequences for the given cell to be used. Techniques for such introduction and sustained expression are routine and are well known to those of skill in the art.

A therapeutic minigene for the amelioration of ADPKD symptoms can comprise a nucleotide sequence which encodes at least one PKD1 gene product peptide domain, as shown in FIGS. 7 and 8. For example, such PKD1 peptide domains (the approximate amino acid residue positions of which are listed in parentheses after each domain name) can include a leucinerich repeat domain (72 to 94, or 97 to 119) and/or a cysteine-rich repeat domain (32 to 65), a C-type (calcium dependent) lectin protein domain (405 to 534), an LDL-A module (641 to 671), one or more PKD domains (282 to 353; 1032 to 1124; 1138 to 1209; 1221 to 1292; 1305 to 1377; 1390 to 1463; 1477 to 1545; 1559 to 1629; 1643 to 1715; 1729 to 1799; 1815 to 1884; 1898 to 1968; 1983 to 2058; 2071 to 2142), or at least one C-terminal domain (2160 to 4304) (i.e., a peptide domain found in the C-terminal half of the PKD1 gene product). Minigenes which encode such PKD1 gene products can be synthesized and/or engineered using the PKD1 gene sequence (SEQ ID NO:1) disclosed herein, and by utilizing the amino acid residue domain designations found in FIGS. 7 and 8.

Among the ways whereby the PKD1 minigene product activity can be assayed involves the use of PKD1 knockout animal models. Such animal models express an insufficient level of the PKD1 gene product. The production of such animal models may be as described above, in Section 5.8.2, and involves methods well known to those of skill in the art. PKD1 minigenes can be introduced into the PKD1 knockout animal models as, for example, described above, in this Section. The activity of the minigene can then be assessed by assaying for the amelioration of ADKPD-like symptoms. Thus, the relative importance of each of the PKD peptide domains, individually and/or in combination, with respect to PKD1 gene activity can be determined.

Cells, preferably, autologous cells, containing normal PKD1 expressing gene sequences may then be introduced or reintroduced into the patient at positions which allow for the amelioration of ADPKD symptoms. Such cell replacement techniques may be preferred, for example, when the PKD1 gene product is a secreted, extracellular gene product.

5.11. PHARMACEUTICAL PREPARATIONS AND METHODS OF ADMINISTRATION

The identified compounds that inhibit PKD1 expression, synthesis and/or activity can be administered to a patient at therapeutically effective doses to treat polycystic kidney disease. A therapeutically effective dose refers to that amount of the compound sufficient to result in amelioration of symptoms of polycystic kidney disease.

5.11.1. EFFECTIVE DOSE

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Additional factors which may be utilized to optimize dosage can include, for example, such factors as the severity of the ADPKD symptoms as well as the age, weight and possible additional disorders which the patient may also exhibit. Those skilled in the art will be able to determine the appropriate dose based on the above factors.

5.11.2. FORMULATIONS AND USE

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.12. DIAGNOSIS OF PKD1 ABNORMALITIES

A variety of methods may be employed, utilizing reagents such as PKD1 nucleotide sequences described in Sections 5.1, and antibodies directed against PKD1 gene product or peptides, as described, above, in Section 5.1.3. Specifically, such reagents may be used for the detection of the presence of PKD1 mutations, i.e., molecules present in diseased tissue but absent from, or present in greatly reduced levels relative to, the corresponding non-diseased tissue.

The methods described herein may be performed, for example, by utilizing pre-packaged diagnostic kits comprising at least one specific PKD1 nucleic acid or anti-PKD1 antibody reagent described herein, which may be conveniently used, e.g., in clinical settings, to diagnose patients exhibiting PKD1 abnormalities.

Any tissue in which the PKD1 gene is expressed may be utilized in the diagnostics described below.

5.12.1 DETECTION OF PKD-1 NUCLEIC ACIDS

RNA from the tissue to be analyzed may be isolated using procedures which are well known to those in the art. Diagnostic procedures may also be performed in situ directly upon tissue sections (fixed and/or frozen) of patient tissue obtained from biopsies or resections, such that no RNA purification is necessary. Nucleic acid reagents such as those described in Section 5.1, and its subsections, may be used as probes and/or primers for such in situ procedures (Nuovo, G. J., 1992, PCR in situ hybridization: protocols and applications, Raven Press, N.Y.).

PKD1 nucleotide sequences, either RNA or DNA, may, for example, be used in hybridization or amplification assays of biological samples to detect abnormalities of PKD1 expression; e.g., Southern or Northern analysis, single stranded conformational polymorphism (SSCP) analysis including in situ hybridization assays, alternatively, polymerase chain reaction analyses. Such analyses may reveal both quantitative abnormalities in the expression pattern of the PKD1 gene, and, if the PKD1 mutation is, for example, an extensive deletion, or the result of a chromosomal rearrangement, may reveal more qualitative aspects of the PKD1 abnormality.

Preferred diagnostic methods for the detection of PKD1 specific nucleic acid molecules may involve for example, contacting and incubating nucleic acids, derived from the target tissue being analyzed, with one or more labeled nucleic acid reagents as are described in Section 5.1, under conditions favorable for the specific annealing of these reagents to their complementary sequences within the target molecule. Preferably, the lengths of these nucleic acid reagents are at least 15 to 30 nucleotides. After incubation, all non-annealed nucleic acids are removed. The presence of nucleic acids from the target tissue which have hybridized, if any such molecules exist, is then detected. Using such a detection scheme, the target tissue nucleic acid may be immobilized, for example, to a solid support such as a membrane, or a plastic surface such as that on a microtiter plate or polystyrene beads. In this case, after incubation, non-annealed, labeled nucleic acid reagents of the type described in Section 5.1 and its subsections are easily removed. Detection of the remaining, annealed, labeled nucleic acid reagents is accomplished using standard techniques well-known to those in the art.

Alternative diagnostic methods for the detection of PKD1 specific nucleic acid molecules may involve their amplification, e.g., by PCR (the experimental embodiment set forth in Mullis, K. B., 1987, U.S. Pat. No. 4,683,202), ligase chain reaction (Barany, F., 1991, Proc. Natl. Acad. Sci. USA 88:189–193), self sustained sequence replication (Guatelli, J. C. et al., 1990, Proc. Natl. Acad. Sci. USA 87:1874–1878), transcriptional amplification system (Kwoh, D.Y et al., 1989, Proc. Natl. Acad. Sci. USA 86:1173–1177), Q-Beta Replicase (Lizardi, P. M. et al., .1988, Bio/Technology 6:1197), or any other RNA amplification method, followed by the detection of the amplified molecules using techniques well known to those of skill in the art. These detection schemes are especially useful for the detection of RNA molecules if such molecules are present in very low numbers.

In one embodiment of such a detection scheme, a cDNA molecule is obtained from the target RNA molecule (e.g., by reverse transcription of the RNA molecule into cDNA). Tissues from which such RNA may be isolated include any tissue in which wild type PKD1 is known to be expressed, including, but not limited, to kidney tissue and lymphocyte tissue. A target sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the PKD1 nucleic acid reagents described in Section 5.1 and its subsections. The preferred lengths of such nucleic acid reagents are at least 15–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

5.12.2. DETECTION OF PKD1 GENE PRODUCT AND PEPTIDES

Antibodies directed against wild type or mutant PKD1 gene product or peptides, which are discussed, above, in Section 5.3, may also be used as ADPKD diagnostics, as described, for example, herein. Such diagnostic method, may be used to detect abnormalities in the level of PKD1 protein expression, or abnormalities in the location of the PKD1 tissue, cellular, or subcellular location of PKD1 protein. For example, in addition, differences in the size, electronegativity, or antigenicity of the mutant PKD1 protein relative to the normal PKD1 protein may also be detected.

Protein from the tissue to be analyzed may easily be isolated using techniques which are well known to those of skill in the art. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, New York), which is incorporated herein by reference in its entirety.

Preferred diagnostic methods for the detection of wild type or mutant PKD1 gene product or peptide molecules may involve, for example, immunoassays wherein PKD1 peptides are detected by their interaction with an anti-PKD1 specific peptide antibody.

For example, antibodies, or fragments of antibodies, such as those described, above, in Section 5.3, useful in the present invention may be used to quantitatively or qualitatively detect the presence of wild type or mutant PKD1 peptides. This can be accomplished, for example, by immunofluorescence techniques employing a fluorescently labeled antibody (see below) coupled with light microscopic, flow cytometric, or fluorimetric detection. Such techniques are especially preferred if PKD1 gene products or peptides are expressed on the cell surface.

The antibodies (or fragments thereof) useful in the present invention may, additionally, be employed histologically, as in immunofluorescence or immunoelectron microscopy, for in situ detection of PKD1 gene product or peptides. In situ detection may be accomplished by removing a histological specimen from a patient, and applying thereto a labeled antibody of the present invention. The histological sample may be taken from a tissue suspected of exhibiting ADPKD. The antibody (or fragment) is preferably applied by overlaying the labeled antibody (or fragment) onto a biological sample. Through the use of such a procedure, it is possible to determine not only the presence of the PKD1 peptides, but also their distribution in the examined tissue. Using the present invention, those of ordinary skill will readily perceive that any of a wide variety of histological methods (such as staining procedures) can be modified in order to achieve such in situ detection.

Immunoassays for wild type or mutant PKD1 gene product or peptides typically comprise incubating a biological sample, such as a biological fluid, a tissue extract, freshly harvested cells, or cells which have been incubated in tissue culture, in the presence of a detectably labeled antibody capable of identifying PKD1 peptides, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled PKD1 specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule, is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild type or mutant PKD1 peptide antibody may be determined according to well known methods. Those skilled in the art will be able to determine operative and optimal assay conditions for each determination by employing routine experimentation.

One of the ways in which the PKD1 peptide-specific antibody can be detectably labeled is by linking the same to an enzyme and use in an enzyme immunoassay (EIA) (Voller, A., "The Enzyme Linked Immunosorbent Assay (ELISA)", Diagnostic Horizons 2:1–7, 1978) (Microbiological Associates Quarterly Publication, Walkersville, Md.); Voller, A. et al., J. Clin. Pathol. 31:507–520 (1978); Butler, J. E., Meth. Enzymol. 73:482–523 (1981); Maggio, E. (ed.), ENZYME IMMUNOASSAY, CRC Press, Boca Raton, Fla., 1980; Ishikawa, E. et al., (eds.) ENZYME IMMUNOASSAY, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alphaglycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments it is possible to detect PKD1 wild type or mutant peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

6. EXAMPLE

DETERMINATION OF THE PKD1 INTERVAL VIA GENETIC POLYMORPHISM ANALYSIS

In the Working Example presented herein, genetic linkage studies are discussed which successfully reduced the potential PKD1 interval from approximately 750 kb to approximately 460 kb, thus substantially narrowing the genomic region in which the gene responsible for ADPKD lies.

6.1 MATERIALS AND METHODS

Sequencing techniques: Sequencing of cDNA clones and genomic clones was carried out using an Applied Biosystems ABI 373 automated sequencing machine according to the manufacturer's recommendations or by manual sequencing according to the method of Ausubel P. M. et al., eds., 1989, Current Protocols in Molecular Biology, Vol. I, Green Publishing Associates, Inc., and John Wiley & Sons, New York, pp. 7.0.1 & ff.

Inserts from the cDNA phage clones were excised with EcoRI and ligated into the appropriate cloning sites in the polylinker of pBlueScript plasmid (Stratagene). Primers for sequencing of the plasmid clones were based on the known sequence of the polylinker. A second set of sequencing primers were based on the DNA sequences obtained from the first sequencing reactions. Sequences obtained using the second set of primers were used to design a third set of primers and so on. Both strands of the double-stranded plasmids were sequenced.

PCR products were sequenced using the dsDNA cycle sequencing system of GIBCO-BRL (Gaithersburg, Md.) according to the manufacturer's instructions. PCR product was purified, prior to sequencing, by passing the DNA through a Centricon column twice according to the manufacturer's instructions (Amicon, Beverly, Mass., USA). 100–200 ng of each purified PCR product was used as template in the sequence reaction.

Genomic sequences were obtained from PCR products as well as from subclones from the cosmids. To ensure the correct locus sequence was obtained over the duplicated locus. Only cGGG10 and cDEB11 sequence was utilized when identifiying intron/exon boundaries.

DNA labelling: Double-stranded DNA probes were made by labelling DNA by the method of Feinberg and Vogelstein, 1983, Anal. Biochem. 132: 6–13. Primers were end-labelled with $\gamma^{32}$p-ATP using the method of Ausubel F. M. et al., eds., 1989, Current Protocols in Molecular Biology, Vol-1, Green Publishing Associates, Inc., and John Wiley & Sons, New York, pp. 4.8.2 & ff.

PCR conditions: Conditions for the PCR reactions were determined empirically for each reaction by analyzing an array of reaction conditions with the following variables: magnesium concentrations of 1 mM, 2 mM, 4 mM; annealing temperature; extension time; primer concentration and primer concentration ratio.

The fixed conditions were:

1. extension at 72° C. using Taq polymerase, 2.5 u/100 μl reaction volume;
2. denaturation at 95° C. for 1 minute; and
3. annealing for 30 seconds.

Primer design: Primers were designed using the computer program "PRIMER".

Genetic linkage studies: Genetic linkage studies were carried out using computerized algorithms (Lathrop GM., et al., 1984, Proc. Natl. Acad. Sci. USA, 81:3443–3446; Lathrop GM and Lalouel J-M., 1984, Am. J. Hum. Genet. 36:460–465; Lathrop G.M., Lalouel J.-M., Julier C., Ott J., 1985, Am. J. Hum. Genet. 37:482–498).

Single-stranded conformational polymorhism analysis (SSCP):

SSCP analysis to detect sequence polymorphisms was carried out according to the method of Orita et al, 1989, Genomics, 5:874–879. Primers were designed to amplify each exon (see FIG. 10 and Table 1, below). The 3' end of each primer was designed to lie ~20–50 bp from the nearest intron/exon boundary so that mutations in the splice donor and acceptor sites could be detected.

TABLE 1

Primer Sequences from the PKD1 gene

| Primer Name | Sequence (5'-3') | Sense/antisense |
|---|---|---|
| KG8-F9 (SEQ ID NO: 3) | CTGCCGGCCTGGTGTCG | sense |
| KG8-F11 (SEQ ID NO: 4) | AGGGTCCACACGGGCTCGG | sense |
| KG8-F23 (SEQ ID NO: 5) | CAGGGTGTCCGTGCGTGACTG | sense |
| KG8-F25 (SEQ ID NO: 6) | GTCCAGCACTCCTGGGGAGA | sense |
| KG8-F26 (SEQ ID NO: 7) | ACGCAAGGACAAGGGAGTAG | sense |
| KG8-F27 (SEQ ID NO: 8) | AGTGCCGCGGCCTCCTGAC | sense |
| KG8-F28 (SEQ ID NO: 9) | GCTGGCCTAGGCGGCTTCCA | sense |
| KG8-MF2 (SEQ ID NO: 10) | CACCCCACGGCTTTGCACT | sense |
| KG8-MF4 (SEQ ID NO: 11) | CCCAGGCAG CGAGGCTGTC | sense |
| KG8-RO2 (SEQ ID NO: 12) | ACACCAGGCCAACAGCGACTG | antisense |
| KG8-R9 (SEQ ID NO: 13) | ACAGCCACCAGGAGCAGGCTG | antisense |
| KG8-R13 (SEQ ID NO: 14) | TGTAGCGCGTGAGCTCCAG | antisense |
| KG8-23 (SEQ ID NO: 15) | CACCCCACCCTACCCCAAG | antisense |
| KG8-24 (SEQ ID NO: 16) | GGAGGCCACAGGTGAGGCT | antisense |
| KG8-R27 (SEQ ID NO: 17) | CGGAGGAGTGAGGTGGGCTCC | antisense |
| KG8-R28 (SEQ ID NO: 18) | AGCCATTGTGAGGACTCTCCC | antisense |
| NKG9-F2 (SEQ ID NO: 19) | AAGACCTGATCCAGCAGGTCC | sense |
| NKG9-F07 (SEQ ID NO: 20) | CAGCACGTCATCGTCAGG | sense |
| NKG9-R03 (SEQ ID NO: 21) | CTCCCAGCCACCTTGCTC | antisense |
| NKG9-R07 (SEQ ID NO: 22) | GCAGCTGTCGATGTCCAG | antisense |
| NKG9-RM2 (SEQ ID NO: 23) | TCTGTCCAACAAAGGCCTG | antisense |

6.2 RESULTS

It was previously shown that the PKD1 gene maps, by genetic linkage, to the interval between the polymorphic genetic markers D16S259 (which lies on the telomeric side of PKD1) and D16S25 (which lies on the centromeric side of PKD1) (see Somlo et al., 1992, Genomics 13:152). The smallest interval between genetic markers, called the PKD1 interval was found to be approximately 750 kb (see Germino et al., 1992, Genomics 13:144). The PKD1 interval was isolated as a series of forty overlapping cosmid and phage clones. The cloned DNA contained the entire PKD1 interval with the exception of two gaps of less than 10kb and less than 50 kb (see FIG. 1; Germino et al., Genomics 13:144, 1992).

In the Example presented herein, in order to reduce the PKD1 interval still further, a systematic search for additional polymorphic markers was undertaken. Single-stranded DNA probes $(CA)_{8-15}$ were hybridized to the set of clones from the PKD1 interval. The phage clone w5.2 (see FIG. 1) ,was found to hybridize to the probe and the sequence flanking the (CA)n (w5.2 repeat) was determined using phage DNA as a template. Primers for the polymerase chain reaction (PCR) were designed and used to detect polymorphism within the w5.2Ca repeat. The position of the w5.2Ca repeat is shown in FIG. 2. This w5.2Ca repeat was used in genetic linkage studies in 15, PKD1 families and found to lie proximal to the PKD1 locus. This experiment reduced the size of the PKD1 interval to approximately 460 kb, as shown in FIG. 2.

7. EXAMPLE

IDENTIFICATION OF POTENTIAL PKD1 TRANSCRIPTS

In the Working Example presented herein, transcription units within the 460 kb PKD1 interval, (FIG. 2) defined in Section 6, above, were identified. The interval was found to have a maximum of 27 transcriptional units (TU), which contained a total of approximately 300 kb.

7.1 MATERIALS AND METHODS cDNA library screening: cDNA libraries were prepared from several sources including EBV transformed lymphocytes, teratocarcinoma tissue, fetal kidney and HeLa cells. In addition a human adult kidney library was purchased from Clontech Inc. (San Diego, Calif.).

Total RNA from each tissue was prepared by the guanidinium chloride method. First strand cDNA synthesis was prepared using random six base oligonucleotides by the method of Zhou et al, Journal Biol. Chem., 267:12475 (1992). EcoRI sites within the cDNA were blocked by DNA methylase. The cDNA was treated with T4 kinase and flush-ended with and EcoRI linkers added with T4 kinsae and DNA ligase. The cDNA was cleaved with EcoRI and ligated into either bacteriophage lambda-gt10 or lambda-ZAP (Stratagene). The phage were packaged with high-efficiency packaging extract (Stratagene). At least one million primary clones were plated. The library was amplified 100-fold and stored at 40° C.

At least 500,000 plaques of each library were screened with each cosmid clone at a density of 25,000 per 75 mm diameter plate. Duplicate filter lifts were made of each plate (Ausubel, supra). The radiolabelled probes were incubated with an excess of unlabelled denatured human DNA and then added to the library filters in a sodium phosphate buffer at 65° C. for 16 hours. The filters were washed in 2×SSC at 65° C. for 1 hour and 0.1×SSC, 0.1×SDS at 65° C. for one hour. Kodak XAR-5 was exposed to the library filters for 4–16 hours. Duplicate positives were picked and replated at a density of approximately 100–500 per plate. Filter lifts of these secondary plates were made and hybridized as for the primary lifts; pure isolated plaques were obtained and inoculated into 50ml cultures and the phage DNA was purified.

Secuencing techniques: Techniques were as described in Section 6.1, above.

7.2 RESULTS

To identify transcribed sequences within the PKD1 interval (FIG. 2), the cosmid and phage clones from the interval were hybridized to cDNA libraries made from a variety of human tissues including fetal and adult kidney, teratocarcinoma, adult liver, lymphoblast, HeLa, and adult brain. More than 100 hybridizing cDNA clones were identified. These clones were subcloned into pBlueScript plasmids and sequenced. The sequence data combined with hybridization data (between cDNA clone and genomic clone) allowed the cDNA clones to be assigned to a maximum of 27 transcription units, as described below.

Namely, hybridization between two cDNA clones was evidence that the clones are part of the same transcription units. Similarly, sequence identities of greater than 25 bp between the cDNA clones were used as evidence that the clones were part of the same transcription unit.

Table 2, below, lists these units (a–z, aa) by the name of the longest clone.

TABLE 2

Putative Transcriptional Unit Sequences Isolated Prom the PKD1 Region
CANDIDATE GENES IN THE PKD1 REGION

| | Clone | Insert Size (kb) | cDNA Libraries | Motif |
|---|---|---|---|---|
| a. | 20.7 | 2.1 | cy, terat | |
| b. | SazD | 2.7 | cy | G-protein 6 ≦ pd. |
| e. | Saz13 | 1.5 | cy, terat | tandem 120 amino-acid repeat; Z01 - family |
| f. | Saz20 | 5.5 | cy, lym, terat | |
| g. | KG8 | 3.4 | lym | |
| h. | NKG9 | 1.8 | lym | |
| i. | NKG10 | 2.8 | lym | |
| j. | NKG11 | 2.4 | lym | |
| k. | Nik4 | 0.9 | kid | |
| l. | Nik7 | 2.3 | lym, terat | rab gene motif |
| m. | KG3 | 3.8 | terat, cy | G-protein β subunit-like |
| n. | Nik9 | 2.2 | cy | ankyrin repeat |
| o. | KG4 | 0.6 | kid | |
| p. | KM17 | 1.6 | terat, cy | G-protein β subunit4ike |
| q. | Nik10 | 1.6 | lym | |
| r. | KG5 | 2.6 | cy | zinc-finger protein |
| s. | KG1 | 1.1 | kid | DNase |
| t. | KG6 | 3.4 | kid, cy, lym | human homolog of mouse RNSP1 gene |
| u. | Nik3 | 3.2 | terat, lym, cy | * |
| v. | Nik2 | 3.4 | terat, lym,cy | * |
| w. | Nik1 | 0.8 | kid | * |
| x. | Nik8 | 1.6 | lym | * |
| y. | KG17 | 2.2 | lym | |
| z. | AJ1 | 1.4 | cy | cyclin-F homolog |
| aa. | MAR1 | 2.0 | kid | MDR-like |

*u, v, w, x are part of an 8kb transcriptional unit (nik 823) which produces a MDR-like channel. MAR1 is another member of the gene family. ATP-dependent transporter cyclin proton-channel of vacuolar proton ATPase cDNA library from which the clone was obtained: cy = cyst; terat = teratocarcinoma; lym = lymphoblast; kid = kidney Thus, these 27 transcription units were considered by virtue of their genomic localization to be candidate genes for PKD1. The total transcribed cDNA in the 27 transcription units equalled about 60 kb.

The sequence of each clone was compared with sequences deposited in the public databases Genbank, EMBL, and SwissProt. Several of the cDNA clones contained sequences predicted to code for known protein motifs. Because so little was known of the molecular basis of ADPKF none of the candidate genes could be ruled out by virtue of sequence motifs.

8. PKD1 INTERVAL NORTHERN ANALYSIS

In the Working Example presented herein, an analysis of the transcriptional expression patterns of the TUs described, above, in Section 7, was conducted.

8.1 MATERIALS AND METHODS

Northern blot analysis: Poly A+ RNA (2 μg) from heart, brain, placenta, lung, liver, skeletal muscle, kidney and pancreas was hybridized with radio-labelled cDNA probes from the TUs within the PKD1 interval, under standard conditions.

8.2 RESULTS

Inserts from the cDNA clones of the TUs described in Section 7, and listed in Table 2, above, were used to probe Northern blots containing total RNA and polyA-enriched RNA from normal human organs and from between 8 and 10 kidneys removed from patients with ADPKD.

The expression profile was compared with the pattern of pathology in ADPKD to determine a priority for further characterization. The Northern analysis demonstrated that 26 of the TUs in the PKD1 interval were expressed in kidney, with the exception of Nik9. Nik9 mRNA was found to be abundant in human brain but expressed at very low level in fetal and adult human kidney. These data, therefore, indicated that Nik9 is not the PKD1 gene. No consistent differences were observed between normal and ADPKD kidneys for any transcript.

9. EXAMPLE

PKD1 INTERVAL MUTATION SCREENS

A systematic search was undertaken to detect mutations in ADPKD patients in the transcribed regions listed in Table 2. The mutation screen used several independent techniques. Southern blot analysis of patient DNA digested with at least three different restriction endonucleases was performed. Several differences between the restriction patterns were detected but none was found only in patients with ADPKD. Single-stranded conformational polymorphism analysis was carried out using cDNA isolated from patient transformed lymphocytes as a template. A large number of allelic differences was found but none were found to alter the deduced product of transcription. Sequence analysis of the KG5 cDNA was carried out in seven ADPKD patients and one normal. The deduced coding region of 2.6 kb was sequenced using cDNA, made by reverse transcription from patient transformed lymphocyte mRNA, as a template. The cDNA was amplified by PCR in a series of overlapping sections and the PCR products were sequenced. No sequence differences were detected between patients and normal individuals. In this way more than 80% of the coding DNA in the transcription units was scanned and no mutations were found in PKD1 patients. These experiments excluded the scanned segments of the transcription units with a likelihood of 95% based on the reasonable assumption that no ADPKD mutation accounts for >70% of all ADPKD cases.

Thus, the following transcription units were excluded: sazB, sazD saz13, KG3, KG5, KGI, saz20, KM17, Nik1, Nik2, Nik3, Nik8, KG17, Nik7, MAR1. These excluded transcripts represent >80% of the combined identified coding sequences in the PKD1 region. It has previously been noted that de novo mutation to ADPKD accounts for at least 1% of cases. Two mechanisms have been shown to account for the vast majority of new mutation rates of this order. First, the coding region may be large. Duchenne muscular dystrophy (DMD) provides an example of this situation: the dystrophin gene which is mutated in DMD has a transcript of approximately 14 kb. About 30% of DMD cases arise by de novo mutation. The second mechanism that may account for a high new mutation rate is the presence of an unstable repetitive element. Unstable trinucleotide repeats in which the repeat sequence contains >50% C and G have been shown to cause the fragile X syndrome, Huntington's disease and myotonic dystrophy. In two of these diseases, high mutation rates or the appearance of progressively more severe disease in successive generations (anticipation) have been documented.

A systematic search for trinucleotide repeats in the PKD1 interval was undertaken. Single-stranded probes (15–25 nucleotides) containing all possible combinations of trinucleotide repeats were synthesized, radiolabelled and hybridized to Southern blots containing the complete set of clones comprising the PKD1 interval. The hybridization and washing conditions were adjusted to allow detection of all perfect repeats of 15 nucleotides or more. Eight separate banks of trinucleotide repeats within the PKD1 interval were found. Primers were designed so that the trinucleotide repeat arrays could be amplified by PCR and size-fractionated on polyacrylamide gels. No differences were found between ADPKD patients and controls.

Additionally, two other screening methods were attempted for the identification of trinucleotide expansions in the PKD1 interval. Southern blots of DNA from normal and affected individuals was probed with inserts containing the repeats. This revealed no polymorphisms. Further, multiply restricted DNA samples (Rsa/Sau3A/Hinf1) samples were probed with trinucleotide repeat oligonucleotides. Though myotonic dystrophy and fragile-X mental retardation patients could be identified via such methods, it was not possible to identify any common pattern in ADPKD patients.

The cDNA clones Nik1, Nik2, Nik3, and Nik8 were found to hybridize to an 8 kb transcript present in kidney. These clones were assumed to be part of the same transcript. PCR product that bridged the three gaps in sequence between the four clones were obtained using primers based on sequences within the four cDNA clones. In this way approximately 8 kb of the transcribed DNA sequence of the gene represented by Nik1, Nik2, Nik3, and Nik8 was obtained. Because the coding region is large the gene was expected to have a high spontaneous mutation rate and therefore to be a good candidate for the PKD1 gene. A detailed exon-by-exon search of the gene, however, revealed no evidence of mutations in ADPKD patients. This left only one TU within the region which was considered large enough to be a reasonable candidate for the PKD1 gene. The characterization of clones and sequences within this TU, part of the putative PKD1 gene, is described, below, in the Working Examples presented in Sections 10 and 11.

10. EXAMPLE

SSCP Analysis of ADPKD Patients

In the Working Example presented herein, an SSCP analysis of genomic DNA amplified from DNA derived from normal and ADPKD patients was conducted which identified ADPKD-specific allelic differences which map to the single gene of the PKD1 interval which was described, above, in the Working Example presented in Section 10.

10.1 MATERIALS AND METHODS

SSCP Analysis: Single-Stranded Conformational Analysis (SSCP) was performed as follows: 50ng of genomic DNA was amplified by PCR under standard conditions in a reaction volume of 20 $\mu$l. Ten microliters of the amplified product was added to 90 $\mu$l of formamide buffer, heated at 97° C. for 4–5 minutes, and cooled on ice. Four microliters of the reaction mixture was loaded on a polyacrylamide gel (10%, 50:1 acrylamide:bisacrylamide) containing 10% glycerol. The gel was run at 4° C. for 12 hours with 10W power in 0.5×TBE buffer. The gel was dried and exposed to a Molecular Dynamic Phosphor-Imager screen for 4 to 16 hours.

Intron/Exon Mapping: Primers produced from cDNA clones were used to PCR amplify genomic DNA sequences. Amplified products were sequenced, using standard methods. Those sequences which differed from the cDNA sequences indicated intron sequences.

PCR Amplification: Procedures for amplification were as described, above, in Section 6.1.

10.2 RESULTS

Because the large size of the putative KG8/NKG9/NKG10/NKG11 transcript makes it a likely site for mutation, the intron/exon structure of part of the gene represented by KG8 and NKG9 was determined so that an exon-by-exon search for mutations could be conducted. The exon/intron structure analysis allowed PCR primers to be designed for the amplification of several exons of the PKD1 gene.

These primers were used to PCR-amplify genomic DNA and to perform SSCP of ADPKD patients and normal individuals. In two ADPKD patients SSCP patterns were observed that showed allelic differences. Both patients were heterozygous for an SSCP variant that was not seen in a large number of normals from the normal population (FIG. 3A–3B). In samples from these two individuals, 4 bands are visible, instead of the 2 single-strand bands seen in samples from normal individuals. The 4 bands are of equal intensity and are presumed to comprise two allelic sense strand and two allelic antisense strands.

Thus, the results discussed in this Example, coupled with the analyses reported, above, in the Examples presented in Sections 6 through 9 provide positive correlative evidence that the gene corresponding to the putative transcription unit of which the clones KG8, NKG9, NKG10 and NKG11 are believed to be a part, is the PKD1 gene.

11. EXAMPLE

MOLECULAR CHARACTERIZATION OF THE PKD1 GENE

In this Example, the complex structure of the PKD1 gene and gene product is described. Included herein is a description of the PKD1 gene structure, the nucleotide sequence of the entire coding region of the PKD1 trancript, as well as the amino acid sequence and domain structure of the PKD1 gene product. This description not only represents the first elucidation of the entire PKD1 coding sequence, but additionally also corrects errors in the portionof the PKD1 coding region which had previously been reported. Also, a ADPKD-causing mutation within the PKD1 gene which results in a frameshift is identified. Further, the strategy utilized to characterize this extensive and difficult nucleic acid region is summarized.

A portion of the nucleotide sequence corresponding, in large part, to the 3' end of the PKD1 gene had recently been reported (European Polysystic Kidney Disease Consortium [hereinafter abbreviated EPKDC], 1994, Cell 77:881–894). Specifically, the terminal 5.6 kb of the PKD1 transcript were studied and an open reading frame of 4.8 kb was reported. The peptide this putative open reading frame encodes, which would correspond to the carboxy terminal portion of the PKD1 protein, did not reveal any homologies to known proteins and, if this derived amino acid sequence was, in fact, part of the PKD1 protein, its sequence did not suggest a function for the PKD1 gene product.

For this lack of revealing information, in addition to the fact that only a small percentage of ADPKD-causing mutations appear to reside within the 3' end of the PKD1 gene, the characterization of the 5' end of the gene and a more complete analysis of the PKD1 gene and gene product were greatly needed.

As acknowledged by the EPKDC (EPKDC, 1994, Cell 77:881–894), however, the elucidation of the complete PKD1 coding sequence presents major problems. Unlike the 3' end of the PKD1 gene, the 5' two-thirds of the gene appear to be duplicated several times at other genomic positions. Further, at least some of these duplications are transcribed. Thus, great difficulties arise when attempting to distinguish sequence derived from the authentic PKD1 locus apart from sequence obtained from the duplicated PKD1-like loci.

11.1. MATERIALS AND METHOIYS

11.1.1. GENOMIC CLONES

The human P1 phage named PKD 1521 was isolated from a human P1 library using primers from the adjacent TSC2 gene.

The first screen utilized primers F33(SEQ ID NO:24) tcttctccaacttcacggctg, R32(SEQ ID NO:25) aaccagccaggttttggtcct, followed by F38(SEQ ID NO:26) caagtccagctcctctccc, R40(SEQ ID NO:24) gctctttaaggcgtccctc and ultimately screened with primers in the KG8 gene (F9/R5) see Table 1 for KG8-F9 primer, while KG8-R5 5'(primer SEQ ID NO:24) is gcgctttgcagacggtag-gog 3'. The cosmid cGGG10 has been previously described (Germino, G. G., Weinstat-Saslow, D., Himmelbauer, H., Gillespie G. A. J., Somlo, S., Wirth, B., Barton, N., Harris, K. L., Frischauf, A. M. and Reeders, S. T. (1992) Genomics, 13:144–151). The cosmid cGGG10 was mapped using various restriction enzymes as described by the manufacturers. A random library of the cosmid was constructed by cloning sheared DNA fragments into the SmaI site of pUC 19. Initial sequence assembly for the cosmid cGGG10 was performed on forward and reverse sequences of approximately 1000 random cloned fragments and a preliminary map was constructed using the restriction map of the cosmid. Directed subclones of cGGG10 were made in the plasmid pBluescript (Stratagene) in order to create sequencing islands specific physical locations. These large subclones from cGGG10 were then restricted with more frequent cutter enzymes and cloned into M13mpl9 and mp18. In addition, if gaps were found in cloned regions, directed sequencing was performed from the flanking regions, to join the anchored contigs. A contig of 34.3 Kb was constructed, with two gaps in what appear to be highly repetitive regions with no identifiable coding sequence. cDEB11 was has been described previously (Germino, G. G., Weinstat-Saslow, D., Himmelbauer, H., Gillespie G. A. J., Somlo, S., Wirth, B., Barton, N., Harris, K. L., Frischauf, A. M. and Reeders, S. T. (19.92) Genomics, 13:144–151). A random library was constructed with sheared cDEB11 DNA and cloned into the SmaI site of pUC19. This cosmid was sequenced to obtain at least 2-fold coverage.

The sequencing was done by cycle sequencing and run on ABI machines following the manufacturer's instructions with modifications as described below. Because of the difficulty of sequencing certain regions, the standard chemistry of sequencing used withthe ABI machines had to be modified. Both dye terminator and dye primer sequence were used when appropriate with sequencing different regions. Different polymerases and different melting and polymerization conditions were also used in order to optimize the quality of the sequence. When sequencing across the CpG island at the 5' end of the PKD1 gene, the best sequencing results were obtained when adding 5% DMSO to the polymerization step and sequencing single-stranded templates.

11.1.2. cDNA LIBRARY SCREENING

The first cDNA used to screen libraries was KG8, which maps to the unique region of the PKD1 locus and was recovered from an adult lymphocyte libary. In order to complete the rest of the PKD1 transcript, fourteen new cDNAs were sequenced to completion, four cDNAs were partially sequenced and an additional 20 cDNAs were mapped against cGGG10. Additional data was obtained from RT-PCR products of the renal cell carcinoma cell line SW839 (ATCC).

Overlapping partial cDNAs described below were isolated from lymphocyte and fetal kidney libraries. In this way, a 14 kb transcript was assembled starting from the 3' until the CpG island was reached. It is assumed that the 5' end of the PKD1 trancript has been located. No other clones further upstream were recovered upon further screening those cDNA libraries that had provided the majority of the cDNAs which were used to assemble the full length PKD1 cDNA.

The cDNAs FK7 and FK11 were recovered from a fetal (gestation age of 14–16 weeks) kidney cDNA library using KG8 cDNA as a probe. This library was constructed with the Superscript Lambda System from (Gibco/BRL), using oligo d(T) primed cDNA. FK7 and FK11 were recovered as SAlI inserts. The cDNAs designated BK156, BK194, UN49 and UN52 were recovered from a lymphocyte cell library ndpuIIea by using FK7 as a probe. UN34 was recovered from the same library by hybridizing with a ScaI-SaII 5' end probe of FK7. UN53, UN54 and UN59 were recovered from the same lymphocyte library (M. Owen laboratory, ICRF; Dunne, PhD thesis, 1994) by double screening clones that were both negative when screening with an FK7 probe and positive when screening with BK156 and UN52. The cDNA NKG11 was recovered from a lymphocyte library screened with cGGG10 and was described previously (Germino, G. G., Weinstat-Saslow, D., Himmelbauer, H., Gillespie G. A. J., Somlo, S., Wirth, B., Barton, N., Harris, K. L., Frischauf, A. M. and Reeders, S. T. (1992) Genomics, 13:144–151). ). The cDNA named Fhkb21 was obtained from a Clonetech fetal kidney library using BK156 as a probe. MSK3 was obtained by probing an adult kidney library (Clonetech) with a probe from 5' end of KG8. MSK4 was obtained by nested RT-PCR from primers spanning from exons 7–8 to exons 13–14, followed by second round of PCR with internal primers in exon 8 and exon 13.

11.1.3. cDNA SEQUENCING

The cDNAs were sequenced to 5-fold coverage by primer walking and/or subloning small fragments into M13 or pBluescript. All cDNA sequences were compared to the cGGG10 cosmid sequence to assess whether they were from the correct locus and to determine intron/exon boundaries. Discrepancies were resequenced to determine whether the differences were genuine. Some of the cDNAs described above were clearly different from the genomic sequence, suggesting that these cDNAs were encoded by another locus.

MSK3, FK7 and FK11 were obtained using a PKD1-specific probe (KG8) were found to be 100% identical to genomic sequence. The cDNA and UN49, which showed 99% identity, is possibly PKD1-specific. BK241, BK194, UN52, UN53, UN54 and UN59, BK156, Fhkb21 and NKG11 were 96–98% homologous to the cGGG10 defined exon sequence, and thus were assumed to have originated fromt the duplicated loci. In general, differences between genomic cDNA were nucleotide differences scattered through out the cDNA sequence. One exception is BK194, which has an extra CAG at position 1863 of the previously published partial sequence and arose from alternative splicing of exon 33. Another exception is BK241 that has an insertion of the following sequence in a tandem repeat of TTATCAATACTCTGGCTGACCATCGTCA(SEQ ID NO:29) at position 1840 of the previously published sequence (European PKD1 Consortium). This sequence was not included in the authentic, full-length PKD1 cDNA because it arose from the duplicated loci which would produce a frame shift in the ccoding region of the PKD1 transcript. Except for BK241, cDNAs in the UN and BK series that overlap with each other are more identical to themselves than to the genomic sequence.

All sequence assembly was performed using the Staden package XBAP (Dear, S. and Staden R. (1991). Nucleic Acid Res. 19:3907–3911.)

11.1.4. PROTEIN HOMOLOGY SEARCHES

The PKD1 derived amino acid sequence was subjected to various sequence analysis methods (Koonin, E. V., Bork, P. and Sanders, C. (1994) Yeast chromosome III: new gene functions. EMBO 13:493–503). For identifying homologues, initial (SWISSPROT, PIR, GENPEPT, TREMBL, EMBL, GENBANK, NRDB) database searches were performed using the blast series of programs (Altschul, S. F. and Lipman, D. J., 1990, Proc. Natl. Acad. Sci. USA 87:5509–5513) by applying filter for compositionally biased regions. (Altschul, S. F. et al., 1994, Nat. Genet. 6:119–129). By default, the BLOSUM62 amino acid exchange matrix was used (Henikoff, S. and Henikoff J. G. (1993). Proteins 17:97–61). In order to reveal additional candidate preoteins that might be homologous to PKD1, the BLOSUM45 and PAM240 matrices were also applied. Putative homolgies with a blast p-value below 0.1 were studied in detail. Multiple alignments of the candidate doma ins were carried out using CLUSTALW (Thompson, J. D., Higgins, D. G. and Gibson, T. (1994). Nucleic Acid Res. 22:4673–4680) and pattern (Rohde, K. and Bork, P. (1993). Comput. Appl. Biosci. 9:183–189), motifs and profiles (Grisbskov, M., McLachlan, A. D. and Eisenberg, D. (1987) Proc. Natl. Acad. Sci. USA 84:4355–4358 ) were d erived. With all these constructs interactive database searches were performed. Results of these database searches were used for improving the multiple alignments that were then used for the next round of database searches. The final multiple alignment containing all retrieved members of a module family was then used as input for the secondary structure predictions (Rost, B. and Sander, C. (1994). Proteins 19:55–872).

11.1.5. SSCP ANALYSIS

Single-Stranded Conformational Analysis (SSCP) was performed as follows: 50 ng of total genomic DNA was amplified by PCR. In addition to the genomic DNA, each PCR reaction contained 1 picomole of each primer (see below), 0.1 ol$^{32}$P dATP (Amersham), 0.2 µl in AmpliTaq (Pharmacia), in PCR buffer with a final Mg$^{2+}$ of 1.5 mM in a final volume of 20 µl. The amplification was performed for 25 cycles, each consisting of 94° C. for 30 seconds, 60° C. for 30 seconds, and 72° C. for 60 seconds.

Intronic primers F25 and Mill-1R were utilized for the initial SSCP evaluation. The fragment amplified with these primers overlaps with the 5' end of KG8. Subsequently, the primers F31 and R35 were ussed to amplify the fragment used to sequence the PKD1 mutation.

Primers: F25 (SEQ ID NO:30) (5' TCGGGGCAGC-CTCTTCCTG 3');

Mill-1R (SEQ ID NO:31) (5' TACAGG-GAGGGGCTAGGG 3');

F31 (SEQ ID NO:32) (5' TGCAACTGCCTCCTGGAGG 3')

R35 (SEQ ID NO:33) (5' GGTCTGTCTCTGCTTCCC 3')

One microliter of each sample was diluted into loading dye (95% formamide, 20 mM NaOH, 1 mM EDTA, xylene cyanol, bromophenol blue) denatured at 98° C. for 5 minutes, cooled on ice and loaded onto a 10% (50:1 acrylamide:bisacrylamide) polyacrylamide gel containing 10% glycerol. The gel was run at 4° C., 50 watts, for 3 hours. Exposure was overnight on phosphoimager plates.

Amplified DNA from the one individual with a variant pattern was then reamplified using KG8-F31 and KG8-R35 primers and the above-described PCR conditions. Both reamplified strands were then sequenced using standard procedures for cycle sequencing of PCR products. $^{32}$P-dCTP incorporation was used.

11.2 RESULTS

A series of overlapping cosmid clones spanning the predicted PKD1 region has been described (Germino, G. G., Weinstat-Saslow, D., Himmelbauer, H., Gillespie G. A. J., Somlo, S., Wirth, B., Barton, N., Harris, K. L., Frischauf, A. M. and Reeders, S. T. (1992). Genomics, 13:144–151). The integrity of the cosmid contig was confirmed by long-range restriction mapping and genetic linkage analysis of polymorphic sequences derived from the cosmids. Three cosmids (cGGG1, cGGG10 and cDEB11, from centromere to telomere) form a contig that includes the 3' end of the adjacent gene, TSC2, (cDEB11) and spans over 80 kilobases centromeric. At the proximal end of cGGg10, there is a CpG island represented by the Not I site, N54T (FIG. 1A).

In order to identify transcripts from the region, the cosmid clones were hybridized to a set of five cDNA libraries. KG8, a cDNA corresponding to the distal 3.2 kb of the PKD1 sequence (which is located on cosmid cDEB11), was mapped using a panel of somatic cell hybrids, and found to hybridize to a single locus on chromosome 16p13. Sequence analysis confirmed that KG8 contains the polyadenylated 3' end of a gene and has an open reading frame (ORF) of 2100 bp and a 1068 bp 3' untranslated region. KG8 was also found to contain a polymorphic (CA) microsatellite repeat (Snarey). Analysis of this repeat in a large number of PKD1 kindreds revealed no recombination (Solmo) supra.

To obtain clones extending 5' of KG8, the cosmids cGGG10 and cDEB11 were hybridized to different cDNA libraries. When some of the positive clones obtained from these screens were analyzed using somatic cell hybrid panels, they were found to hybridize strongly to several loci on chromosome 16 in addition to the PKD1 region. The restriction maps of the hybridizing loci were so similar that it was concluded that a series of recent duplications of part of the PKD1 gene had occurred (excluding the PKD1 region from which the KG8 cDNA is derived) which had given rise to several PKD1-like genomic segments. This sequence duplication had been reported by the European PKD1 Consortium (EPKDC, 1994, Cell 77:881–894). Preliminary sequence analysis of the cDNA clones revealed that the PKD1 and PKD1-like loci give rise to two or more transcripts sharing 95–98% sequence identity. Because of the high degree of similarity between PKD1 and PKD1-like transcripts, therefore, it was not possible to determine the correct full-length PKD1 cDNA sequence by simply assembling overlapping partial cDNA clones.

To begin to determine the sequence-of the authentic PKD1 transcript, therefore, it was concluded that genomic PKD1 sequence should be compared to that of the PKD1 specific and PKD1-like cDNAs homologous to the genomic sequence. To that end, the entire cGGG10 cosmid and PKD1 exon-containing parts of the cDEB11 cosmid were sequenced, as described below.

11.2.1 SEQUENCE OF THE GENOMIC REGION OF THE PKD1 LOCUS

The duplicated portion of the PKD1 gene is largely contained within the cosmid cGGG10. Prior to sequencing cGGG10, the integrity of the clone was established in several ways. First, the restriction map of cGGG10 was compared with map of the genomic DNA from the PKD1 region. Second, restriction maps of the overlapping portions of cGGG1 and cDEB11 were compared with cGGG10. Third, sequences derived from cGGG10 and overlapping portions of cDEB11 showed 100% similarity. Finally, a P1 phage, PKD1521, was obtained by screening a genomic P1 library with primers from the TSC2 gene, which maps near the PKD1 gene. No sequence differences were obtained between PKD 1521 and cGGG10.

It was necessary to pursue several approaches to obtain the sequence of cGGG10 (see Section 11.1, above). Briefly, due to the difficulty of sequence certain regions, modifications to standard automated sequencing chemistries had to be made. Both dye terminator and dye primer sequence was used, when appropriate, with several different regions. Further, different polymerases and different meltng and polymerization conditions were necessary to optimize the quality of the nucleotide sequence. When sequencing across the CpG island at the 5' end of the PKD1 gene, in addition to modifying the polymerization step, single-stranded templates were used.

A final ten fold redundancy was achieved for the cGGG10 cosmid in order to be able to accurately compare the genomic sequence with that of the PKD1 specific and PKD1-like cDNAs homologous to this cosmid. The cGGG10 sequences were assembled into three contigs of 8 kb, 23 kb and 4.4 kb, separated by 1 kb and 2.2 kb gaps. A two-fold redundancy was obtained for the cDEB11 cosmid, whose sequence was compared to PKD1 locus specific cDNAs in order to obtain intron/exon boundaries of the unique 3' end of the PKD1 gene.

11.2.2. PKD1 and PKD1-LIKE cDNAs

In order to identify putative coding regions and intron/exon boundaries, genomic and cDNA sequences were compared. cDNA clones had been identified in two ways. First, fragments of cosmids cGGG10 and cDEB were hybridized to five cDNA libraries. Second, each cDNA clone was hybridized to fetal kidney and lymphocyte cDNA libraries to obtain overlapping clones with which to extend the sequence (FIG. 1B).

When the sequences of overlapping cDNAs were assembled, a PKD1 trancript length of 14.2 kb was obtained. The predominant transcript detected by Northern analysis using the unique sequence KG8 probe is approximately 14 kb, suggesting that the cDNA clones represent the full-length of the PKD1 trancript.

Restriction and sequence analyses indicate that a CpG island overlaps the 5' end of the sequence. CpG islands hae been found to mark the 5' ends of many genes (Antequera). Further, the most 5' cDNA clones (UN53, UN54 and UN59) each have identical 5' ends, providing additional evidence that no upstream PKD1 exons were missed (see Section 11.1, above).

The multiple cDNAs used to assemble the PKD1 trancript along with the genomic sequence are shown in FIGS. 1A and 1B. By comaring the sequences of overlapping cDNAs and analyzing the degree of homology between the different cDNAs and genomic sequence, it was possible to distinguish cDNAs encoded by the authentic PKD1 locus frm those encoded y the homologous loci (see Section 11.1, above). The full length PKD1 trancript constructed from these exons produces a large continuous open reading frame of 12,902 bp.

Significant sequence heterogeneity was observed in these cDNAs, suggesting that some level of alternative splicing of the primary PKD1 transcript occurs. For this reason, it was sought to isolate a minimum of two cDNAs containing each exon, in order to increase the probability that all exons contributing to the PKD1 transcript were detected. Formally, however, it remains possible that there exist PKD1 transcripts which ccontain exons that are not present in the cDNA clones samples here.

Exon 17 was found in two cDNA clones (UN34 and BK156) and in the cosmid sequence, but the exon was not incorporated into the final PKD1 transcript. This is due to a number of reasons. First, the cDNA clones in which this exon is found differed from the cosmid and are likely to represent PKD1-like genes, rather than the authentic PKD1 gene (see Section 11.1, above). Second, this exon is not found in FK1, a cDNA which was cloned using a PKD1-specific probe (KG8). Finally, when included in the full-length cDNA, this exon introduces a stop codon (743 nucleotides downstream of exon 17) that would produce a truncated protein of 2651 amino acid residues. Further studies are needed to assess whether this exon may be used in different splice combinations in locus specific trancripts. An ADPKD patient with a heterozygous mutation which introduces a stop codon at position 10,594 of the PKD1 open reading frame was identified. Other mutations that truncate the PKD1 protein have also been reported by the European PKD1 Consortium. Therefore, it is unlikely that transcripts which include exon 17 are predomiant forms in the kidney.

11.2.3. SEQUENCE ANALYSIS OF THE PREDICTED PKD1 PROTEIN

The assembly of 46 PKD1 exons yields a predicted transcript is 14.2 kb in length with 228 bp nucleotides of putative 5' untranslated and 790 nucleotides of 3' untranslated sequence. The authentic PKD1 transcript differs from the reported 3' PKD1 sequence (EPKDC, 1994, Cell 77:881–894) due to the presence of two extra cytosines at position 12873 of the PKD1 open reading frame (corresponding to PBP position 4563). This frameshift yielded an erroneous carboxy PKD1 derived amino acid sequence which contained almost 80 additional amino acid residues. The presence of the two extra cytokines as confirmed with the cosmid sequence derived from cDEB11.

The PKD1 protein derived from the assembled PKD1 transcript is 4304 amino acids in length, with a predicted molecular weight of 462 kilodaltons. The nucleotide sequence encompassing the Met-1 codon is CTAACGATGC (SEQ ID NO:34), which represents an uncommon translation start site (Kozak, M. (1984). Nucleic Acids Res. 12:857–872). This methionine was determined to be the putative PKD1 translation start site because it is preceded by an in-frame stop codon 63 bases upstream. Furthermore, the PKD1 coding region begins with a 23 amino acid region which exhibits many of the properties of a signal peptide and corresponding cleavage site (von Hejne, G. (1986). Nucleic Acids Res. 14:4683–4690. Welling, L. W. Grantham, J. J. (1972). J. Clin. Invest. 51:1063–1075).

In addition to the signal sequence, the identification of five domains that have been identified in other proteins and a newly discovered domain strongly suggests the extracellular location of at least the N-terminal half of the protein. Immediately downstream of the signal sequence there are two leucine-rich repeats (LRRS) (FIG. 7). These LRRs are flanked on both sides by a cysteine rich regions which have homology to the flanking regions of a subset of other LRRS. LRRs occur in numerous proteins and have been shown to be involved in diverse forms of protein-protein interactions. The number of LRR within the respective proteins varies between 2 and 29 (Kobe B. and Deisenhofer J. (1994). Treds. Biochem. Sci. 19:415–421). Adhesive platelet glycoproteins form the largest group in the LRR superfamily (Kobe B. and Deisenhofer J. (1994). Treds. Biochem. Sci. 19:415–421). The structure of the array of 15 LRRs in porcine ribonuclease inhibitor (RI) has recently been crystallized (Kobe B. and Deisenhofer J. (1995). Nature 374:183–186); the LRRs of the RI protein form a horseshoe-like structure that surrounds RNase A (Kobe B. and Deisenhofer J. (1995). Nature 374:183–186). It has been suggested that proteins containing only a few LRRS, like the PKD1 protein, interact with other proteins via the LRRs in order to form the horseshoe-like superstructure for protein-binding (Kobe B. and Deisenhofer J. (1994).

Although LRRS occur in various locations in different proteins, the additional flanking cysteine-rich disulfide bridge-containing domains, define a subgroup of extracellular proteins (Kobe B. and Deisenhofer J. (1994). Only a few proteins have been sequenced so far that contain both, the distinct N-terminal and C-terminal flanking cysteine-rich domains (FIGS. 7 and 8). Among this group are toll, slit, trk, trkB and trkC, which are all involved in cellular signal transduction. For example, the Drosophila toll protein is suspected to be involved in either adhesion or signaling required to mediate developmental events such as dorsal-ventral patterning (Hashimoto, C., Hudson, K. L., and Anderson, K. V. (1988). Cell 52:269–279). The Drosophila slit protein is thought to possible mediate interactions between growing axons and the surrounding matrix (Rothberg, J. M., Jacobs, J. R., Goodman, C. S., and Artavanis Takonas, S. (1990). Genes and Dev. 4:2169–2187). In vertebrates, these domains are found in the trk family of tyrosine kinase receptors; these proteins may relay cell or matrix adhesive events to the cytoplasm via a small carboxy terminal kinase domain (Schneider, R., Schweider, M. (1991). Oncogene 6:1807–11). it is interesting to note that all of the proteins with these cysteine-rich domains are involved in extracellular function, many of which relate to cell adhesion. For example, the platelet glycoproteins I and V help mediate the adhesion of platelets to sites of vascular injury. The 5T4 oncofetal trophoblast glycoprotein appears to be highly expressed in metastatic tumors.

The PKD1 protein also contains a single domain with homologies to C-type (calcium-dependent) lectin proteins (FIGS. 7 and 8). These domains are believed to be involved in the extracellular binding of carbohydrate residues for diverse purposes, including internalization of glycosylatedenzyme (asialoglycoprotein receptors), participation in extracellular matrix (versican) and cell adhesion (selectins). The classification of C-type lectins has been based on exon organization and the nature and arrangement of domains within the protein (Bezouska). For example, class I (extracellular proteoglycans) and class II (type II transmembrane receptors) all have three exons encoding for the carbohydrate recognition domain (CRD); where as in classes III (collectins) and IV (LEC-CAMS) the domains are encoded by a single exon. The CRD in PKD1 C-type lectin domain does not fit into the above classification because it has a novel combination of protein domains and because it is encoded by two exons (exons 5 and 6, FIG. 6). Previous analysis has failed to establish a correlation between the type of carbohydrate bound to each C-type lectin and the primary structure of its CRD (Weis).

Exon 10 encodes a LDL-A module (from amino acids 642–672, FIG. 7), a cysteine-rich domain of about 40 amino acids in length. This module was originally identified in the LDL-receptor but it is also present extracellular portions of many other proteins, often in tandem arrays (FIG. 7). Because of their hydrophobic nature, these domains have been implicated as ligand-binding regions in LDL receptor-related pr. Other proteins, like the PKD1 protein, that contain a single or nontandem LDL-A, include the complement proteins (DiScipio, R. G., Gehring, M. R., Podack, E. R., Kan, C. C. Hugli, T. E., and Fey., G. H. (1984) Proc. Natl. Acad. Sci. USA 81:7298–7302), calf enterokinase (Kitamoto, Y., Yan, X. W., McCourt, D. W. and Sadler, J. E. (1994). Proc. Natl. Acad. Sci. USA 91:7588–7592) and a sarcoma virus adhesion protein.

In addition to extracellular protein modules that have been recognized previously, the PKD1 protein a novel domain of approximately 70 amino acids in length, present in 14 copies (FIGS. 7 and 8). The first one is encoded by exon 5 between the LRRs and the C-type lectin module. The other PKD domains are consecutively placed starting at amino acid 1100 and ending at amino acid 2331 and contained in exons 13, 14, and 15. Profile and motif searches (see Section 11.1, above) identified several other extracellular proteins that also contain one or more copies of this novel domain, which we call the PKD domain. Whereas all known extracellular modules seem to be restricted to higher organisms, and the few exceptions seem to be evolutionary accidents, we found the PKD domain in extracellular parts of proteins from animals, eubacteria and archeabacteria. The animal proteins containing an individual PKD domain are heavily glycosylated, melanoma-associated cell surface proteins, such as melanocyte-specific human pmel17 (Kwon BS. (1993) J. Invest. Derm. (Supplement) 100:134–140), the MMP 115 protein (Mochii, M., Agata, K. and Eguchi, G. (1991). Pigment Cell Res. 4:41–47), and the nmb protein (Weterman, M. A. J., Ajubi, N., van Dinter, I. Degen, W., van Muijen, G., Ruiter D. J. and Bloemers, H. P. J. (1995). Int. J. Cancer 60:73–81). The physiological functions of these glycoproteins remains to be elucidated. Four enbacterial extracelluar enzymers, three distinct collagenases and lysine-specific achromobacter protease I (API) also contain a single copy of the domain adjacent to their catalytic domains. Curiously, the highest degree of similarity between the collagenases is in the PKD domain. This may suggest that the domain in eukaryotic cells is involved in binding to collagenous domains. Four copies of the PKD domain are also present in the surface layer protein (SlpB) from methanothermus. The SlpB protein is (as is the PMEL17 family) heavily glycosylated and is predicted to be a glycoprotein component of the surface layer.

The PKD domain is predicted to be a globular domain that contains an antiparallel β-sheet. Although the PKD domains do not contain conserved cysteines, we believe they are extracellular domains because: 1) all identified homologues are extracellular or the PKD domain is in the extracellular part; 2) the first domain (amino add 281–353) is located between other known extracellular modules; and 3) there are no predicted transmembrane regions between the other identified (extracellular) modules and the 13 remaining FKD domains. Whereas the PKD domains in SlpB are very similar, pointing to rather recent duplication; the 14 domains in PKD1 are rather divergent. Even the most conserved (WDFGDG) motif (SEQ ID NO:35) (FIG. 7) is considerably modified in some of the PKD domains. Therefore, it is unlikely that unequal recombination between genomic sequences for motifs is a common source of mutations in this disease.

Although, it was not possible to identify specific domains in the C-terminal half of the protein, a long region was found which contained similarity to a putative *C. elegans* Chromosome III protein (accession number Z48544; Wilson). A hydrophobic stretch of 60 amino acids from 3986 to 4045 might represent a possible transmembrane domain, but without any clear resemblance to other such domains.

11.2.4. IDENTIFICATION OF AN ADPKD-CAUSING MUTATION

SSCP analysis was performed on samples obtained from 60 patients, as described, above, in Section 10.1. One variant ADPKD individual was identified via SSCP. Upon reamplification of amplified DNA from this individual (see Section 10.1, above), it was revealed that the patient contained a C to T transition at base pair 10,594 (exon 32) of the full-length PKD1 transcript. This mutation created a stop codon (TAG) at PKD1 amino acid position 3532 which previously coded for a glutamine (CAG), thus truncating the final 772 amino acid residues which are normally present at the carboxy end of the PKD1 protein and yielding a final mutant protein of 3531 amino acids. The mutation was also predicted to create a novel Sty-1 site (CCCTAG); genomic DNA spanning this exon was amplified as before from the patient, his parents, and over 60 other unrelated individuals (120 alleles). After Sty-1 digestion, only the patient ZC (#118) was heterozygous for an enzyme site. The absence of the sequence change in over 120 alleles establishes this is not a polymorphic variation. The absence of the site in either parent establishes this as a new mutation, which corelates with the appearance of disease. Finally, the predicted impact on the protein (truncation) by itself is highly suggestive that it would impair or alter its function. This evidence, even in the absence of examination of the remainer of the gene or transcript in this patient, would be considered generally to be sufficient proof that this mutation is the cause of the disease.

12. DEPOSIT OF MICROORGANISMS AND NUCLEIC ACID

The following microorganisms and plasmid nucleic acid were deposited under the provisions of the Budapest Treaty on the International Recognition of the Deposit of Microorganisms for the Purposes of Patent Procedure, and comply with the criteria set forth in 37 C.F.R. §§1.801–1.809 regarding availability and permanency of deposits. The microorganisms and plasmid nucleic acid were deposited with the American Type Culture Collection (12301 Parklawn Drive, Rockville, Md., 20852) on May 27, 1994 and assigned the indicated accession numbers:

| Microorganism | ATCC Accession No. |
|---|---|
| cGGG10 | 69634 |
| cDEB11 | 69635 |
| Plasmid | ATCC Accession No. |
| KG8 | 69636-- |

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

---

What is claimed is:

1. An antibody that immunospecifically binds to a PKD1 polypeptide, wherein the PKD1 polypeptide comprises the amino acid sequence encoded by the PKD1 nucleotide sequence of clone cDEB11 (ATCC Accession No. 69635), cGGG10 (ATCC Accession No. 69634), KG8 (ATCC Accession No. 69636), or an allelic variant thereof.

2. A method of detecting the presence of a PKD1 polypeptide in a sample comprising:
   (a) contacting a sample suspected of containing a PKD1 polypeptide with an antibody that binds to a PKD1 polypeptide under conditions which allow for the formation of reaction complexes comprising the antibody and the PKD1 polypeptide; and
   (b) detecting the formation of reaction complexes comprising the antibody and PKD1 polypeptide in the sample, in which detection of the formation of reaction complexes indicates the presence of the PKD1 polypeptide in the sample,
wherein the PKD1 polypeptide comprises the amino acid sequence encoded by the PKD1 nucleotide sequence of clone cDEB11 (ATCC Accession No. 69635), cGGG10 (ATCC Accession No. 69634), KG8 (ATCC Accession No. 69636), or an allelic variant thereof.

3. The method of claim 2 in which the antibody is bound to a solid phase support.

4. The method of claim 2 in which the PKD1 polypeptide is bound to a solid phase support.

5. A method of measuring the level of PKD1 polypeptide in a biological sample comprising:
   (a) detecting the formation of reaction complexes in a biological sample according to the method of claim 2; and
   (b) measuring the amount of reaction complexes formed, which amount of reaction complexes corresponds to the level of PKD1 polypeptide in the biological sample.

6. The method of claim 3 or 4 which additionally comprises contacting the sample with a labeled PKD1 polypeptide in step (a), and removing unbound substances prior to step (b), in which a decrease in the amount of reaction complexes comprising the antibody and the labelled PKD1 polypeptide indicates the presence of the PKD1 polypeptide in the sample.

7. A method of detecting or diagnosing the presence of a disease associated with elevated or decreased level of PKD1 polypeptide in a mammalian subject comprising:
   (a) measuring the level of PKD1 polypeptide in a biological sample from the mammalian subject according to claim 5; and
   (b) comparing the level detected in step (a) to a level of PKD1 polypeptide present in normal subjects or in the subject at an earlier time, in which an increase or a decrease in the level of the PKD1 polypeptide as compared to normal levels indicates a disease condition.

8. A method for monitoring a therapeutic treatment of a disease associated with elevated or decreased levels of PKD1 polypeptide according to the method of claim 5 in a mammalian subject, comprising measuring the levels of the PKD1 polypeptide in a series of biological samples obtained at different time points from a mammalian subject undergoing a therapeutic treatment for a disease associated with elevated or decreased levels of PKD1 polypeptide.

9. The method according to claim 7 or 8 wherein the disease associated with decreased levels of PKD1 polypeptide is selected from the group consisting of polycystic kidney disease, and acquired cystic disease.

10. A test kit for measuring the presence of or amount of PKD1 polypeptide in a sample, comprising:
   (a) an antibody that immunospecifically binds to a PKD1 polypeptide;
   (b) means for detecting binding of the antibody to PKD1 polypeptide in a sample; and
   (c) directions for use of the kit,
wherein the PKD1 polypeptide comprises the amino acid sequence encoded by the PKD1 nucleotide sequence of clone cDEB11 (ATCC Accession No. 69635), cGGG10 (ATCC Accession No. 69634), KG8 (ATCC Accession No. 69636), or an allelic variant thereof.

11. A method for detecting a nucleic acid encoding a PKD1 polypeptide in a sample, said method comprising:
   (a) contacting a sample suspected of containing the nucleic acid encoding the PKD1 polypeptide with a PKD1 gene sequence probe under stringent hybridization conditions that allow formation of a hybrid complex comprising the nucleic acid encoding the PKD1 polypeptide and the PKD1 gene sequence probe, wherein the stringent hybridization conditions comprise hybridization to filter bound DNA in 0.5M $NaHPO_4$, 7% SDS, 1 mM EDTA at 65° C., and washing in 0.1×SSC/0.1% SDS at 68° C.;
   (b) detecting the presence of the hybrid complex, in which detection of the hybrid complex indicates the presence of a nucleic acid encoding a PKD1 polypeptide in the sample,
wherein the PKD1 polypeptide comprises the amino acid sequence encoded by the PKD1 gene produced by clone cDEB11 (ATCC Accession No. 69635), cGGG10 (ATCC Accession No. 69634), KG8 (ATCC Accession No. 69636), or an allelic variant thereof.

12. The method of claim 11 in which the sample is bound to a solid phase support.

13. The method of claim 11 in which the sample nucleic acid encoding PKD1 is an RNA molecule.

14. The method of claim 11 in which the sample nucleic acid encoding PKD1 is an DNA molecule.

15. The method of claim 11, wherein the PKD1 gene sequence probe comprises a nucleotide sequence containing at least 15 contiguous nucleotides of
the PKD1 nucleotide sequence of clone cDEB11 (ATCC Accession No. 69635), cGGG10 (ATCC Accession No. 69634), or KG8 (ATCC Accession No. 69636).

16. The method of claim 11, wherein the sample nucleic acid sequence detected is rearranged in or absent from a wild type, non-(autosomal dominant polycystic kidney disease) individual, so that detection of the sample nucleic acid encoding PKD1 identifies a mutant PKD1 gene sequence.

17. The nucleic acid of claim 16, wherein the nucleic acid detected contains a stop codon at PKD1 amino acid residue 3532 as depicted in FIG. 6 (SEQ ID NO:2).

18. A method for detecting a nucleic acid encoding a PKD1 polypeptide in a sample, said method comprising:
(a) contacting a sample suspected of containing the nucleic acid encoding the PKD1 polypeptide with at least one PKD1 gene sequence primer under stringent hybridization conditions that allow annealing of the primer to sample nucleic acid, wherein the stringent hybridization conditions comprise hybridization to filter bound DNA in 0.5M $NaHPO_4$, 7% SDS, 1 mM EDTA at 65° C., and washing in 0.1×SSC/0.1% SDS at 68° C.;
(b) amplifying sample nucleic acid using the PKD1 gene sequence primer; and
(c) detecting the presence of the amplified sample nucleic acid, in which detection of the amplified sample nucleic acid indicates the presence of the nucleic acid encoding a PKD1 polypeptide in the sample,
wherein the PKD1 polypeptide comprises the amino acid sequence encoded by the PKD1 nucleotide sequence of clone cDEB11 (ATCC Accession No. 69635), cGGG10 (ATCC Accession No. 69634), KG8 (ATCC Accession No. 69636), or an allelic variant thereof.

19. The method of claim 18 wherein the sample nucleic acid is RNA and the method further comprises reverse transcribing the sample nucleic acid into cDNA, prior to step (a).

20. The method of claim 18 or 19, wherein detecting the amplified sample nucleic acid is accomplished by single stranded conformational analysis.

21. The method of claim 20, wherein the sample nucleic acid sequence detected is absent from a wild type, non-(autosomal dominant polycystic kidney disease) individual, so that detection of the sample nucleic acid encoding PKD1 identifies a mutant PKD1 gene sequence.

22. The method of claim 18 or 19, wherein the sample nucleic acid sequence detected is rearranged in or absent from a wild type, non-(autosomal dominant polycystic kidney disease) individual, so that detection of the sample nucleic acid encoding PKD1 identifies a mutant PKD1 gene sequence.

23. The method of claim 18, wherein the PKD1 gene sequence probe comprises a nucleotide sequence containing at least 15 contiguous nucleotides of:
the PKD1 nucleotide sequence contained in clone cDEB11 (ATCC Accession No. 69635), cGGG10 (ATCC Accession No. 69634), or KG8 (ATCC Accession No. 69636).

24. The nucleic acid of claim 18, wherein the nucleic acid detected contains a stop codon at PKD1 amino acid residue 3532 as depicted in FIG. 6 (SEQ ID NO:2).

25. A method of measuring the level of nucleic acid encoding PKD1 in a sample, comprising:
(a) amplifying sample nucleic acid encoding PKD1 according to the method of claim 18; and
(b) measuring the amount of amplified sample nucleic acid, so that the amount of nucleic acid encoding PKD1 in the sample is measured.

26. The method of claim 25 wherein the sample nucleic acid is RNA and the method further comprises reverse transcribing the sample nucleic acid into cDNA, prior to step (a).

27. A method of measuring the level of nucleic acid encoding PKD1 in a biological sample comprising:
(a) detecting the formation of hybrid complexes in a biological sample according to the method of claim 11; and
(b) measuring the amount of reaction hybrid complexes formed, which amount of reaction complexes corresponds to the level of nucleic acid encoding PKD1 in the biological sample.

28. The method of claim 27 wherein the sample nucleic acid encoding PKD1 is RNA.

29. A method of detecting or diagnosing the presence of a disease associated with elevated or decreased level of PKD1 gene expression in a mammalian subject comprising:
(a) measuring the level of nucleic acid encoding PKD1 in a biological sample from the mammalian subject according to claim 28 or 26, which level indicates the level of PKD1 gene expression in the mammalian subject; and
(b) comparing the level detected in step (a) to a level of nucleic acid encoding PKD1 present in normal subjects or in the subject at an earlier time, in which an increase or a decrease in the level of the PKD1 gene expression as compared to normal levels indicates a disease condition.

30. The method according to claim 29 wherein the disease associated with decreased levels of PKD1 gene expression is selected from the group consisting of polycystic kidney disease and acquired cystic disease.

* * * * *

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 12912 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..12912

( x i ) SEQUENCE DESCRIPTION: SEQ ID NO:1:

```
ATG CCG CCC GCC GCG CCC GCC CGC CTG GCG CTG GCC CTG GGC CTG GGC        48
Met Pro Pro Ala Ala Pro Ala Arg Leu Ala Leu Ala Leu Gly Leu Gly
 1               5                  10                  15

CTG TGG CTC GGG GCG CTG GCG GGG GGG CCC GGG CGC GGC TGC GGG CCC        96
Leu Trp Leu Gly Ala Leu Ala Gly Gly Pro Gly Arg Gly Cys Gly Pro
             20                  25                  30

TGC GAG CCC CCC TGC CTC TGC GGG CCA GCG CCC GGC GCC GCC TGC CGC       144
Cys Glu Pro Pro Cys Leu Cys Gly Pro Ala Pro Gly Ala Ala Cys Arg
         35                  40                  45

GTC AAC TGC TCG GGC CGC GGG CTG CGG ACG CTC GGT CCC GCG CTG CGC       192
Val Asn Cys Ser Gly Arg Gly Leu Arg Thr Leu Gly Pro Ala Leu Arg
     50                  55                  60

ATC CCC GCG GAC GCC ACA GAG CTA GAC GTC TCC CAC AAC CTG CTC CGG       240
Ile Pro Ala Asp Ala Thr Glu Leu Asp Val Ser His Asn Leu Leu Arg
 65                  70                  75                  80

GCG CTG GAC GTT GGG CTC CTG GCG AAC CTC TCG GCG CTG GCA GAG CTG       288
Ala Leu Asp Val Gly Leu Leu Ala Asn Leu Ser Ala Leu Ala Glu Leu
                 85                  90                  95

GAT ATA AGC AAC AAC AAG ATT TCT ACG TTA GAA GAA GGA ATA TTT GCT       336
Asp Ile Ser Asn Asn Lys Ile Ser Thr Leu Glu Glu Gly Ile Phe Ala
            100                 105                 110

AAT TTA TTT AAT TTA AGT GAA ATA AAC CTG AGT GGG AAC CCG TTT GAG       384
Asn Leu Phe Asn Leu Ser Glu Ile Asn Leu Ser Gly Asn Pro Phe Glu
        115                 120                 125

TGT GAC TGT GGC CTG GCG TGG CTG CCG CAA TGG GCG GAG GAG CAG CAG       432
Cys Asp Cys Gly Leu Ala Trp Leu Pro Gln Trp Ala Glu Glu Gln Gln
    130                 135                 140

GTG CGG GTG GTG CAG CCC GAG GCA GCC ACG TGT GCT GGG CCT GGC TCC       480
Val Arg Val Val Gln Pro Glu Ala Ala Thr Cys Ala Gly Pro Gly Ser
145                 150                 155                 160

CTG GCT GGC CAG CCT CTG CTT GGC ATC CCC TTG CTG GAC AGT GGC TGT       528
Leu Ala Gly Gln Pro Leu Leu Gly Ile Pro Leu Leu Asp Ser Gly Cys
                165                 170                 175

GGT GAG GAG TAT GTC GCC TGC CTC CCT GAC AAC AGC TCA GGC ACC GTG       576
Gly Glu Glu Tyr Val Ala Cys Leu Pro Asp Asn Ser Ser Gly Thr Val
            180                 185                 190

GCA GCA GTG TCC TTT TCA GCT GCC CAC GAA GGC CTG CTT CAG CCA GAG       624
Ala Ala Val Ser Phe Ser Ala Ala His Glu Gly Leu Leu Gln Pro Glu
        195                 200                 205

GCC TGC AGC GCC TTC TGC TTC TCC ACC GGC CAG GGC CTC GCA GCC CTC       672
Ala Cys Ser Ala Phe Cys Phe Ser Thr Gly Gln Gly Leu Ala Ala Leu
    210                 215                 220
```

| | | | | | | | | | | | | | | | | |
|---|---|---|---|---|---|---|---|---|---|---|---|---|---|---|---|---|
| TCG | GAG | CAG | GGC | TGG | TGC | CTG | TGT | GGG | GCG | GCC | CAG | CCC | TCC | AGT | GCC | 720 |
| Ser | Glu | Gln | Gly | Trp | Cys | Leu | Cys | Gly | Ala | Ala | Gln | Pro | Ser | Ser | Ala | |
| 225 | | | | 230 | | | | | 235 | | | | | | 240 | |
| TCC | TTT | GCC | TGC | CTG | TCC | CTC | TGC | TCC | GGG | CCC | CCG | GCA | CCT | CCT | GCC | 768 |
| Ser | Phe | Ala | Cys | Leu | Ser | Leu | Cys | Ser | Gly | Pro | Pro | Ala | Pro | Pro | Ala | |
| | | | | 245 | | | | | 250 | | | | | | 255 | |
| CCC | ACC | TGT | AGG | GGC | CCC | ACC | CTC | CTC | CAG | CAC | GTC | TTC | CCT | GCC | TCC | 816 |
| Pro | Thr | Cys | Arg | Gly | Pro | Thr | Leu | Leu | Gln | His | Val | Phe | Pro | Ala | Ser | |
| | | | 260 | | | | | 265 | | | | | 270 | | | |
| CCA | GGG | GCC | ACC | CTG | GTG | GGG | CCC | CAC | GGA | CCT | CTG | GCC | TCT | GGC | CAG | 864 |
| Pro | Gly | Ala | Thr | Leu | Val | Gly | Pro | His | Gly | Pro | Leu | Ala | Ser | Gly | Gln | |
| | | 275 | | | | | 280 | | | | | 285 | | | | |
| CTA | GCA | GCC | TTC | CAC | ATC | GCT | GCC | CCG | CTC | CCT | GTC | ACT | GAC | ACA | CGC | 912 |
| Leu | Ala | Ala | Phe | His | Ile | Ala | Ala | Pro | Leu | Pro | Val | Thr | Asp | Thr | Arg | |
| | 290 | | | | | 295 | | | | | 300 | | | | | |
| TGG | GAC | TTC | GGA | GAC | GGC | TCC | GCC | GAG | GTG | GAT | GCC | GCT | GGG | CCG | GCT | 960 |
| Trp | Asp | Phe | Gly | Asp | Gly | Ser | Ala | Glu | Val | Asp | Ala | Ala | Gly | Pro | Ala | |
| 305 | | | | 310 | | | | | 315 | | | | | | 320 | |
| GCC | TCG | CAT | CGC | TAT | GTG | CTG | CCT | GGG | CGC | TAT | CAC | GTG | ACG | GCC | GTG | 1008 |
| Ala | Ser | His | Arg | Tyr | Val | Leu | Pro | Gly | Arg | Tyr | His | Val | Thr | Ala | Val | |
| | | | | 325 | | | | | 330 | | | | | | 335 | |
| CTG | GCC | CTG | GGG | GCC | GGC | TCA | GCC | CTG | CTG | GGG | ACA | GAC | GTG | CAG | GTG | 1056 |
| Leu | Ala | Leu | Gly | Ala | Gly | Ser | Ala | Leu | Leu | Gly | Thr | Asp | Val | Gln | Val | |
| | | | 340 | | | | | 345 | | | | | 350 | | | |
| GAA | GCG | GCA | CCT | GCC | GCC | CTG | GAG | CTC | GTG | TGC | CCG | TCC | TCG | GTG | CAG | 1104 |
| Glu | Ala | Ala | Pro | Ala | Ala | Leu | Glu | Leu | Val | Cys | Pro | Ser | Ser | Val | Gln | |
| | | 355 | | | | | 360 | | | | | 365 | | | | |
| AGT | GAC | GAG | AGC | CTC | GAC | CTC | AGC | ATC | CAG | AAC | CGC | GGT | GGT | TCA | GGC | 1152 |
| Ser | Asp | Glu | Ser | Leu | Asp | Leu | Ser | Ile | Gln | Asn | Arg | Gly | Gly | Ser | Gly | |
| | 370 | | | | | 375 | | | | | 380 | | | | | |
| CTG | GAG | GCC | GCC | TAC | AGC | ATC | GTG | GCC | CTG | GGC | GAG | GAG | CCG | GCC | CGA | 1200 |
| Leu | Glu | Ala | Ala | Tyr | Ser | Ile | Val | Ala | Leu | Gly | Glu | Glu | Pro | Ala | Arg | |
| 385 | | | | 390 | | | | | 395 | | | | | | 400 | |
| GCG | GTG | CAC | CCG | CTC | TGC | CCC | TCG | GAC | ACG | GAG | ATC | TTC | CCT | GGC | AAC | 1248 |
| Ala | Val | His | Pro | Leu | Cys | Pro | Ser | Asp | Thr | Glu | Ile | Phe | Pro | Gly | Asn | |
| | | | | 405 | | | | | 410 | | | | | | 415 | |
| GGG | CAC | TGC | TAC | CGC | CTG | GTG | GTG | GAG | AAG | GCG | GCC | TGG | CTG | CAG | GCG | 1296 |
| Gly | His | Cys | Tyr | Arg | Leu | Val | Val | Glu | Lys | Ala | Ala | Trp | Leu | Gln | Ala | |
| | | | 420 | | | | | 425 | | | | | 430 | | | |
| CAG | GAG | CAG | TGT | CAG | GCC | TGG | GCC | GGG | GCC | GCC | CTG | GCA | ATG | GTG | GAC | 1344 |
| Gln | Glu | Gln | Cys | Gln | Ala | Trp | Ala | Gly | Ala | Ala | Leu | Ala | Met | Val | Asp | |
| | | 435 | | | | | 440 | | | | | 445 | | | | |
| AGT | CCC | GCC | GTG | CAG | CGC | TTC | CTG | GTC | TCC | CGG | GTC | ACC | AGG | AGC | CTA | 1392 |
| Ser | Pro | Ala | Val | Gln | Arg | Phe | Leu | Val | Ser | Arg | Val | Thr | Arg | Ser | Leu | |
| | 450 | | | | | 455 | | | | | 460 | | | | | |
| GAC | GTG | TGG | ATC | GGC | TTC | TCG | ACT | GTG | CAG | GGG | GTG | GAG | GTG | GGC | CCA | 1440 |
| Asp | Val | Trp | Ile | Gly | Phe | Ser | Thr | Val | Gln | Gly | Val | Glu | Val | Gly | Pro | |
| 465 | | | | 470 | | | | | 475 | | | | | | 480 | |
| GCG | CCG | CAG | GGC | GAG | GCC | TTC | AGC | CTG | GAG | AGC | TGC | CAG | AAC | TGG | CTG | 1488 |
| Ala | Pro | Gln | Gly | Glu | Ala | Phe | Ser | Leu | Glu | Ser | Cys | Gln | Asn | Trp | Leu | |
| | | | | 485 | | | | | 490 | | | | | | 495 | |
| CCC | GGG | GAG | CCA | CAC | CCA | GCC | ACA | GCC | GAG | CAC | TGC | GTC | CGG | CTC | GGG | 1536 |
| Pro | Gly | Glu | Pro | His | Pro | Ala | Thr | Ala | Glu | His | Cys | Val | Arg | Leu | Gly | |
| | | | 500 | | | | | 505 | | | | | 510 | | | |
| CCC | ACC | GGG | TGG | TGT | AAC | ACC | GAC | CTG | TGC | TCA | GCG | CCG | CAC | AGC | TAC | 1584 |
| Pro | Thr | Gly | Trp | Cys | Asn | Thr | Asp | Leu | Cys | Ser | Ala | Pro | His | Ser | Tyr | |
| | | 515 | | | | | 520 | | | | | 525 | | | | |
| GTC | TGC | GAG | CTG | CAG | CCC | GGA | GGC | CCA | GTG | CAG | GAT | GCC | GAG | AAC | CTC | 1632 |
| Val | Cys | Glu | Leu | Gln | Pro | Gly | Gly | Pro | Val | Gln | Asp | Ala | Glu | Asn | Leu | |
| | 530 | | | | | 535 | | | | | 540 | | | | | |

| | | | | | | | | | | | | | | | | |
|---|---|---|---|---|---|---|---|---|---|---|---|---|---|---|---|---|
| CTC | GTG | GGA | GCG | CCC | AGT | GGG | GAC | CTG | CAG | GGA | CCC | CTG | ACG | CCT | CTG | 1680 |
| Leu | Val | Gly | Ala | Pro | Ser | Gly | Asp | Leu | Gln | Gly | Pro | Leu | Thr | Pro | Leu | |
| 545 | | | | 550 | | | | | 555 | | | | | | 560 | |
| GCA | CAG | CAG | GAC | GGC | CTC | TCA | GCC | CCG | CAC | GAG | CCC | GTG | GAG | GTC | ATG | 1728 |
| Ala | Gln | Gln | Asp | Gly | Leu | Ser | Ala | Pro | His | Glu | Pro | Val | Glu | Val | Met | |
| | | | 565 | | | | | 570 | | | | | 575 | | | |
| GTA | TTC | CCG | GGC | CTG | CGT | CTG | AGC | CGT | GAA | GCC | TTC | CTC | ACC | ACG | GCC | 1776 |
| Val | Phe | Pro | Gly | Leu | Arg | Leu | Ser | Arg | Glu | Ala | Phe | Leu | Thr | Thr | Ala | |
| | | 580 | | | | | 585 | | | | | 590 | | | | |
| GAA | TTT | GGG | ACC | CAG | GAG | CTC | CGG | CGG | CCC | GCC | CAG | CTG | CGG | CTG | CAG | 1824 |
| Glu | Phe | Gly | Thr | Gln | Glu | Leu | Arg | Arg | Pro | Ala | Gln | Leu | Arg | Leu | Gln | |
| | | 595 | | | | | 600 | | | | | 605 | | | | |
| GTG | TAC | CGG | CTC | CTC | AGC | ACA | GCA | GGG | ACC | CCG | GAG | AAC | GGC | AGC | GAG | 1872 |
| Val | Tyr | Arg | Leu | Leu | Ser | Thr | Ala | Gly | Thr | Pro | Glu | Asn | Gly | Ser | Glu | |
| | 610 | | | | | 615 | | | | | 620 | | | | | |
| CCT | GAG | AGC | AGG | TCC | CCG | GAC | AAC | AGG | ACC | CAG | CTG | GCC | CCC | GCG | TGC | 1920 |
| Pro | Glu | Ser | Arg | Ser | Pro | Asp | Asn | Arg | Thr | Gln | Leu | Ala | Pro | Ala | Cys | |
| 625 | | | | 630 | | | | | 635 | | | | | | 640 | |
| ATG | CCA | GGG | GGA | CGC | TGG | TGC | CCT | GGA | GCC | AAC | ATC | TGC | TTG | CCG | CTG | 1968 |
| Met | Pro | Gly | Gly | Arg | Trp | Cys | Pro | Gly | Ala | Asn | Ile | Cys | Leu | Pro | Leu | |
| | | | 645 | | | | | 650 | | | | | 655 | | | |
| GAC | GCC | TCC | TGC | CAC | CCC | CAG | GCC | TGC | GCC | AAT | GGC | TGC | ACG | TCA | GGG | 2016 |
| Asp | Ala | Ser | Cys | His | Pro | Gln | Ala | Cys | Ala | Asn | Gly | Cys | Thr | Ser | Gly | |
| | | | 660 | | | | 665 | | | | | 670 | | | | |
| CCA | GGG | CTA | CCC | GGG | GCC | CCC | TAT | GCG | CTA | TGG | AGA | GAG | TTC | CTC | TTC | 2064 |
| Pro | Gly | Leu | Pro | Gly | Ala | Pro | Tyr | Ala | Leu | Trp | Arg | Glu | Phe | Leu | Phe | |
| | | 675 | | | | | 680 | | | | | 685 | | | | |
| TCC | GTT | CCC | GCG | GGG | CCC | CCG | GCG | CAG | TAC | TCG | GTC | ACC | CTC | CAC | GGC | 2112 |
| Ser | Val | Pro | Ala | Gly | Pro | Pro | Ala | Gln | Tyr | Ser | Val | Thr | Leu | His | Gly | |
| | 690 | | | | | 695 | | | | | 700 | | | | | |
| CAG | GAT | GTC | CTC | ATG | CTC | CCT | GGT | GAC | CTC | GTT | GGC | TTG | CAG | CAC | GAC | 2160 |
| Gln | Asp | Val | Leu | Met | Leu | Pro | Gly | Asp | Leu | Val | Gly | Leu | Gln | His | Asp | |
| 705 | | | | | 710 | | | | | 715 | | | | | 720 | |
| GCT | GGC | CCT | GGC | GCC | CTC | CTG | CAC | TGC | TCG | CCG | GCT | CCC | GGC | CAC | CCT | 2208 |
| Ala | Gly | Pro | Gly | Ala | Leu | Leu | His | Cys | Ser | Pro | Ala | Pro | Gly | His | Pro | |
| | | | | 725 | | | | 730 | | | | | 735 | | | |
| GGT | CCC | CGG | GCC | CCG | TAC | CTC | TCC | GCC | AAC | GCC | TCG | TCA | TGG | CTG | CCC | 2256 |
| Gly | Pro | Arg | Ala | Pro | Tyr | Leu | Ser | Ala | Asn | Ala | Ser | Ser | Trp | Leu | Pro | |
| | | | 740 | | | | | 745 | | | | | 750 | | | |
| CAC | TTG | CCA | GCC | CAG | CTG | GAG | GGC | ACT | TGG | GGC | TGC | CCT | GCC | TGT | GCC | 2304 |
| His | Leu | Pro | Ala | Gln | Leu | Glu | Gly | Thr | Trp | Gly | Cys | Pro | Ala | Cys | Ala | |
| | | 755 | | | | | 760 | | | | | 765 | | | | |
| CTG | CGG | CTG | CTT | GCA | CAA | CGG | GAA | CAG | CTC | ACC | GTG | CTG | CTG | GGC | TTG | 2352 |
| Leu | Arg | Leu | Leu | Ala | Gln | Arg | Glu | Gln | Leu | Thr | Val | Leu | Leu | Gly | Leu | |
| | 770 | | | | | 775 | | | | | 780 | | | | | |
| AGG | CCC | AAC | CCT | GGA | CTG | CGG | CTG | CCT | GGG | CGC | TAT | GAG | GTC | CGG | GCA | 2400 |
| Arg | Pro | Asn | Pro | Gly | Leu | Arg | Leu | Pro | Gly | Arg | Tyr | Glu | Val | Arg | Ala | |
| 785 | | | | 790 | | | | | 795 | | | | | | 800 | |
| GAG | GTG | GGC | AAT | GGC | GTG | TCC | AGG | CAC | AAC | CTC | TCC | TGC | AGC | TTT | GAC | 2448 |
| Glu | Val | Gly | Asn | Gly | Val | Ser | Arg | His | Asn | Leu | Ser | Cys | Ser | Phe | Asp | |
| | | | | 805 | | | | 810 | | | | | 815 | | | |
| GTG | GTC | TCC | CCA | GTG | GCT | GGG | CTG | CGG | GTC | ATC | TAC | CCT | GCC | CCC | CGC | 2496 |
| Val | Val | Ser | Pro | Val | Ala | Gly | Leu | Arg | Val | Ile | Tyr | Pro | Ala | Pro | Arg | |
| | | | 820 | | | | | 825 | | | | | 830 | | | |
| GAC | GGC | CGC | CTC | TAC | GTG | CCC | ACC | AAC | GGC | TCA | GCC | TTG | GTG | CTC | CAG | 2544 |
| Asp | Gly | Arg | Leu | Tyr | Val | Pro | Thr | Asn | Gly | Ser | Ala | Leu | Val | Leu | Gln | |
| | | 835 | | | | | 840 | | | | | 845 | | | | |
| GTG | GAC | TCT | GGT | GCC | AAC | GCC | ACG | GCC | ACG | GCT | CGC | TGG | CCT | GGG | GGC | 2592 |
| Val | Asp | Ser | Gly | Ala | Asn | Ala | Thr | Ala | Thr | Ala | Arg | Trp | Pro | Gly | Gly | |
| | 850 | | | | | 855 | | | | | 860 | | | | | |

| | | | | | | | | | | | | | | | | |
|---|---|---|---|---|---|---|---|---|---|---|---|---|---|---|---|---|
| AGT | CTC | AGC | GCC | CGC | TTT | GAG | AAT | GTC | TGC | CCT | GCC | CTG | GTG | GCC | ACC | 2640 |
| Ser | Leu | Ser | Ala | Arg | Phe | Glu | Asn | Val | Cys | Pro | Ala | Leu | Val | Ala | Thr | |
| 865 | | | | | 870 | | | | 875 | | | | | | 880 | |
| TTC | GTG | CCC | GCC | TGC | CCC | TGG | GAG | ACC | AAC | GAT | ACC | CTG | TTC | TCA | GTG | 2688 |
| Phe | Val | Pro | Ala | Cys | Pro | Trp | Glu | Thr | Asn | Asp | Thr | Leu | Phe | Ser | Val | |
| | | | | 885 | | | | 890 | | | | | | 895 | | |
| GTA | GCA | CTG | CCG | TGG | CTC | AGT | GAG | GGG | GAG | CAC | GTG | GTG | GAC | GTG | GTG | 2736 |
| Val | Ala | Leu | Pro | Trp | Leu | Ser | Glu | Gly | Glu | His | Val | Val | Asp | Val | Val | |
| | | | 900 | | | | | 905 | | | | | 910 | | | |
| GTG | GAA | AAC | AGC | GCC | AGC | CGG | GCC | AAC | CTC | AGC | CTG | CGG | GTG | ACG | GCG | 2784 |
| Val | Glu | Asn | Ser | Ala | Ser | Arg | Ala | Asn | Leu | Ser | Leu | Arg | Val | Thr | Ala | |
| | | 915 | | | | | 920 | | | | | 925 | | | | |
| GAG | GAG | CCC | ATC | TGT | GGC | CTC | CGC | GCC | ACG | CCC | AGC | CCC | GAG | GCC | CGT | 2832 |
| Glu | Glu | Pro | Ile | Cys | Gly | Leu | Arg | Ala | Thr | Pro | Ser | Pro | Glu | Ala | Arg | |
| 930 | | | | | 935 | | | | | 940 | | | | | | |
| GTA | CTG | CAG | GGA | GTC | CTA | GTG | AGG | TAC | AGC | CCC | GTG | GTG | GAG | GCC | GGC | 2880 |
| Val | Leu | Gln | Gly | Val | Leu | Val | Arg | Tyr | Ser | Pro | Val | Val | Glu | Ala | Gly | |
| 945 | | | | | 950 | | | | | 955 | | | | | 960 | |
| TCG | GAC | ATG | GTC | TTC | CGG | TGG | ACC | ATC | AAC | GAC | AAG | CAG | TCC | CTG | ACC | 2928 |
| Ser | Asp | Met | Val | Phe | Arg | Trp | Thr | Ile | Asn | Asp | Lys | Gln | Ser | Leu | Thr | |
| | | | | 965 | | | | 970 | | | | | | 975 | | |
| TTC | CAG | AAC | GTG | GTC | TTC | AAT | GTC | ATT | TAT | CAG | AGC | GCG | GCG | GTC | TTC | 2976 |
| Phe | Gln | Asn | Val | Val | Phe | Asn | Val | Ile | Tyr | Gln | Ser | Ala | Ala | Val | Phe | |
| | | | 980 | | | | | 985 | | | | | | 990 | | |
| AAG | CTC | TCA | CTG | ACG | GCC | TCC | AAC | CAC | GTG | AGC | AAC | GTC | ACC | GTG | AAC | 3024 |
| Lys | Leu | Ser | Leu | Thr | Ala | Ser | Asn | His | Val | Ser | Asn | Val | Thr | Val | Asn | |
| | | 995 | | | | | 1000 | | | | | 1005 | | | | |
| TAC | AAC | GTA | ACC | GTG | GAG | CGG | ATG | AAC | AGG | ATG | CAG | GGT | CTG | CAG | GTC | 3072 |
| Tyr | Asn | Val | Thr | Val | Glu | Arg | Met | Asn | Arg | Met | Gln | Gly | Leu | Gln | Val | |
| | | | 1010 | | | | 1015 | | | | 1020 | | | | | |
| TCC | ACA | GTG | CCG | GCC | GTG | CTG | TCC | CCC | AAT | GCC | ACG | CTA | GCA | CTG | ACG | 3120 |
| Ser | Thr | Val | Pro | Ala | Val | Leu | Ser | Pro | Asn | Ala | Thr | Leu | Ala | Leu | Thr | |
| 1025 | | | | 1030 | | | | | 1035 | | | | | | 1040 | |
| GCG | GGC | GTG | CTG | GTG | GAC | TCG | GCC | GTG | GAG | GTG | GCC | TTC | CTG | TGG | ACC | 3168 |
| Ala | Gly | Val | Leu | Val | Asp | Ser | Ala | Val | Glu | Val | Ala | Phe | Leu | Trp | Thr | |
| | | | | 1045 | | | | | 1050 | | | | | | 1055 | |
| TTT | GGG | GAT | GGG | GAG | CAG | GCC | CTC | CAC | CAG | TTC | CAG | CCT | CCG | TAC | AAC | 3216 |
| Phe | Gly | Asp | Gly | Glu | Gln | Ala | Leu | His | Gln | Phe | Gln | Pro | Pro | Tyr | Asn | |
| | | | | 1060 | | | | | 1065 | | | | | | 1070 | |
| GAG | TCC | TTC | CCA | GTT | CCA | GAC | CCC | TCG | GTG | GCC | CAG | GTG | CTG | GTG | GAG | 3264 |
| Glu | Ser | Phe | Pro | Val | Pro | Asp | Pro | Ser | Val | Ala | Gln | Val | Leu | Val | Glu | |
| | | 1075 | | | | | 1080 | | | | | 1085 | | | | |
| CAC | AAT | GTC | ACG | CAC | ACC | TAC | GCT | GCC | CCA | GGT | GAG | TAC | CTC | CTG | ACC | 3312 |
| His | Asn | Val | Thr | His | Thr | Tyr | Ala | Ala | Pro | Gly | Glu | Tyr | Leu | Leu | Thr | |
| | | | 1090 | | | | 1095 | | | | | 1100 | | | | |
| GTG | CTG | GCA | TCT | AAT | GCC | TTC | GAG | AAC | CTG | ACG | CAG | CAG | GTG | CCT | GTG | 3360 |
| Val | Leu | Ala | Ser | Asn | Ala | Phe | Glu | Asn | Leu | Thr | Gln | Gln | Val | Pro | Val | |
| 1105 | | | | | 1110 | | | | | 1115 | | | | | 1120 | |
| AGC | GTG | CGC | GCC | TCC | CTG | CCC | TCC | GTG | GCT | GTG | GGT | GTG | AGT | GAC | GGC | 3408 |
| Ser | Val | Arg | Ala | Ser | Leu | Pro | Ser | Val | Ala | Val | Gly | Val | Ser | Asp | Gly | |
| | | | | 1125 | | | | | 1130 | | | | | 1135 | | |
| GTC | CTG | GTG | GCC | GGC | CGG | CCC | GTC | ACC | TTC | TAC | CCG | CAC | CCG | CTG | CCC | 3456 |
| Val | Leu | Val | Ala | Gly | Arg | Pro | Val | Thr | Phe | Tyr | Pro | His | Pro | Leu | Pro | |
| | | | | 1140 | | | | | 1145 | | | | | 1150 | | |
| TCG | CCT | GGG | GGT | GTT | CTT | TAC | ACG | TGG | GAC | TTC | GGG | GAC | GGC | TCC | CCT | 3504 |
| Ser | Pro | Gly | Gly | Val | Leu | Tyr | Thr | Trp | Asp | Phe | Gly | Asp | Gly | Ser | Pro | |
| | | | 1155 | | | | | 1160 | | | | | 1165 | | | |
| GTC | CTG | ACC | CAG | AGC | CAG | CCG | GCT | GCC | AAC | CAC | ACC | TAT | GCC | TCG | AGG | 3552 |
| Val | Leu | Thr | Gln | Ser | Gln | Pro | Ala | Ala | Asn | His | Thr | Tyr | Ala | Ser | Arg | |
| | 1170 | | | | | 1175 | | | | | 1180 | | | | | |

```
GGC  ACC  TAC  CAC  GTG  CGC  CTG  GAG  GTC  AAC  AAC  ACG  GTG  AGC  GGT  GCG     3600
Gly  Thr  Tyr  His  Val  Arg  Leu  Glu  Val  Asn  Asn  Thr  Val  Ser  Gly  Ala
1185           1190                     1195                     1200

GCG  GCC  CAG  GCG  GAT  GTG  CGC  GTC  TTT  GAG  GAG  CTC  CGC  GGA  CTC  AGC     3648
Ala  Ala  Gln  Ala  Asp  Val  Arg  Val  Phe  Glu  Glu  Leu  Arg  Gly  Leu  Ser
          1205                     1210                     1215

GTG  GAC  ATG  AGC  CTG  GCC  GTG  GAG  CAG  GGC  GCC  CCC  GTG  GTG  GTC  AGC     3696
Val  Asp  Met  Ser  Leu  Ala  Val  Glu  Gln  Gly  Ala  Pro  Val  Val  Val  Ser
               1220                     1225                     1230

GCC  GCG  GTG  CAG  ACG  GGC  GAC  AAC  ATC  ACG  TGG  ACC  TTC  GAC  ATG  GGG     3744
Ala  Ala  Val  Gln  Thr  Gly  Asp  Asn  Ile  Thr  Trp  Thr  Phe  Asp  Met  Gly
                    1235                     1240                     1245

GAC  GGC  ACC  GTG  CTG  TCG  GGC  CCG  GAG  GCA  ACA  GTG  GAG  CAT  GTG  TAC     3792
Asp  Gly  Thr  Val  Leu  Ser  Gly  Pro  Glu  Ala  Thr  Val  Glu  His  Val  Tyr
1250                     1255                     1260

CTG  CGG  GCA  CAG  AAC  TGC  ACA  GTG  ACC  GTG  GGT  GCG  GGC  AGC  CCC  GCC     3840
Leu  Arg  Ala  Gln  Asn  Cys  Thr  Val  Thr  Val  Gly  Ala  Gly  Ser  Pro  Ala
1265                     1270                     1275                     1280

GGC  CAC  CTG  GCC  CGG  AGC  CTG  CAC  GTG  CTG  GTC  TTC  GTC  CTG  GAG  GTG     3888
Gly  His  Leu  Ala  Arg  Ser  Leu  His  Val  Leu  Val  Phe  Val  Leu  Glu  Val
               1285                     1290                     1295

CTG  CGC  GTT  GAA  CCC  GCC  GCC  TGC  ATC  CCC  ACG  CAG  CCT  GAC  GCG  CGG     3936
Leu  Arg  Val  Glu  Pro  Ala  Ala  Cys  Ile  Pro  Thr  Gln  Pro  Asp  Ala  Arg
                    1300                     1305                     1310

CTC  ACG  GCC  TAC  GTC  ACC  GGG  AAC  CCG  GCC  CAC  TAC  CTC  TTC  GAC  TGG     3984
Leu  Thr  Ala  Tyr  Val  Thr  Gly  Asn  Pro  Ala  His  Tyr  Leu  Phe  Asp  Trp
1315                     1320                     1325

ACC  TTC  GGG  GAT  GGC  TCC  TCC  AAC  ACG  ACC  GTG  CGG  GGG  TGC  CCG  ACG     4032
Thr  Phe  Gly  Asp  Gly  Ser  Ser  Asn  Thr  Thr  Val  Arg  Gly  Cys  Pro  Thr
1330                     1335                     1340

GTG  ACA  CAC  AAC  TTC  ACG  CGG  AGC  GGC  ACG  TTC  CCC  CTG  GCG  CTG  GTG     4080
Val  Thr  His  Asn  Phe  Thr  Arg  Ser  Gly  Thr  Phe  Pro  Leu  Ala  Leu  Val
1345                     1350                     1355                     1360

CTG  TCC  AGC  CGC  GTG  AAC  AGG  GCG  CAT  TAC  TTC  ACC  AGC  ATC  TGC  GTG     4128
Leu  Ser  Ser  Arg  Val  Asn  Arg  Ala  His  Tyr  Phe  Thr  Ser  Ile  Cys  Val
               1365                     1370                     1375

GAG  CCA  GAG  GTG  GGC  AAC  GTC  ACC  CTG  CAG  CCA  GAG  AGG  CAG  TTT  GTG     4176
Glu  Pro  Glu  Val  Gly  Asn  Val  Thr  Leu  Gln  Pro  Glu  Arg  Gln  Phe  Val
                    1380                     1385                     1390

CAG  CTC  GGG  GAC  GAG  GCC  TGG  CTG  GTG  GCA  TGT  GCC  TGG  CCC  CCG  TTC     4224
Gln  Leu  Gly  Asp  Glu  Ala  Trp  Leu  Val  Ala  Cys  Ala  Trp  Pro  Pro  Phe
1395                     1400                     1405

CCC  TAC  CGC  TAC  ACC  TGG  GAC  TTT  GGC  ACC  GAG  GAA  GCC  GCC  CCC  ACC     4272
Pro  Tyr  Arg  Tyr  Thr  Trp  Asp  Phe  Gly  Thr  Glu  Glu  Ala  Ala  Pro  Thr
1410                     1415                     1420

CGT  GCC  AGG  GGC  CCT  GAG  GTG  ACG  TTC  ATC  TAC  CGA  GAC  CCA  GGC  TCC     4320
Arg  Ala  Arg  Gly  Pro  Glu  Val  Thr  Phe  Ile  Tyr  Arg  Asp  Pro  Gly  Ser
1425                     1430                     1435                     1440

TAT  CTT  GTG  ACA  GTC  ACC  GCG  TCC  AAC  AAC  ATC  TCT  GCT  GCC  AAT  GAC     4368
Tyr  Leu  Val  Thr  Val  Thr  Ala  Ser  Asn  Asn  Ile  Ser  Ala  Ala  Asn  Asp
               1445                     1450                     1455

TCA  GCC  CTG  GTG  GAG  GTG  CAG  GAG  CCC  GTG  CTG  GTC  ACC  AGC  ATC  AAG     4416
Ser  Ala  Leu  Val  Glu  Val  Gln  Glu  Pro  Val  Leu  Val  Thr  Ser  Ile  Lys
                    1460                     1465                     1470

GTC  AAT  GGC  TCC  CTT  GGG  CTG  GAG  CTG  CAG  CAG  CCG  TAC  CTG  TTC  TCT     4464
Val  Asn  Gly  Ser  Leu  Gly  Leu  Glu  Leu  Gln  Gln  Pro  Tyr  Leu  Phe  Ser
          1475                     1480                     1485

GCT  GTG  GGC  CGT  GGG  CGC  CCC  GCC  AGC  TAC  CTG  TGG  GAT  CTG  GGG  GAC     4512
Ala  Val  Gly  Arg  Gly  Arg  Pro  Ala  Ser  Tyr  Leu  Trp  Asp  Leu  Gly  Asp
               1490                     1495                     1500
```

-continued

| | | | | | | | | | | | | | | | | |
|---|---|---|---|---|---|---|---|---|---|---|---|---|---|---|---|---|
| GGT | GGG | TGG | CTC | GAG | GGT | CCG | GAG | GTC | ACC | CAC | GCT | TAC | AAC | AGC | ACA | 4560 |
| Gly | Gly | Trp | Leu | Glu | Gly | Pro | Glu | Val | Thr | His | Ala | Tyr | Asn | Ser | Thr | |
| 1505 | | | | 1510 | | | | | 1515 | | | | | | 1520 | |
| GGT | GAC | TTC | ACC | GTT | AGG | GTG | GCC | GGC | TGG | AAT | GAG | GTG | AGC | CGC | AGC | 4608 |
| Gly | Asp | Phe | Thr | Val | Arg | Val | Ala | Gly | Trp | Asn | Glu | Val | Ser | Arg | Ser | |
| | | | 1525 | | | | | 1530 | | | | | 1535 | | | |
| GAG | GCC | TGG | CTC | AAT | GTG | ACG | GTG | AAG | CGG | CGC | GTG | CGG | GGC | CTC | GTC | 4656 |
| Glu | Ala | Trp | Leu | Asn | Val | Thr | Val | Lys | Arg | Arg | Val | Arg | Gly | Leu | Val | |
| | 1540 | | | | | 1545 | | | | | 1550 | | | | | |
| GTC | AAT | GCA | AGC | CGC | ACG | GTG | GTG | CCC | CTG | AAT | GGG | AGC | GTG | AGC | TTC | 4704 |
| Val | Asn | Ala | Ser | Arg | Thr | Val | Val | Pro | Leu | Asn | Gly | Ser | Val | Ser | Phe | |
| | | 1555 | | | | | 1560 | | | | | 1565 | | | | |
| AGC | ACG | TCG | CTG | GAG | GCC | GGC | AGT | GAT | GTG | CGC | TAT | TCC | TGG | GTG | CTC | 4752 |
| Ser | Thr | Ser | Leu | Glu | Ala | Gly | Ser | Asp | Val | Arg | Tyr | Ser | Trp | Val | Leu | |
| | 1570 | | | | | 1575 | | | | | 1580 | | | | | |
| TGT | GAC | CGC | TGC | ACG | CCC | ATC | CCT | GGG | GGT | CCT | ACC | ATC | TCT | TAC | ACC | 4800 |
| Cys | Asp | Arg | Cys | Thr | Pro | Ile | Pro | Gly | Gly | Pro | Thr | Ile | Ser | Tyr | Thr | |
| 1585 | | | | 1590 | | | | | 1595 | | | | | | 1600 | |
| TTC | CGC | TCC | GTG | GGC | ACC | TTC | AAT | ATC | ATC | GTC | ACG | GCT | GAG | AAC | GAG | 4848 |
| Phe | Arg | Ser | Val | Gly | Thr | Phe | Asn | Ile | Ile | Val | Thr | Ala | Glu | Asn | Glu | |
| | | | | 1605 | | | | | 1610 | | | | | 1615 | | |
| GTG | GGC | TCC | GCC | CAG | GAC | AGC | ATC | TTC | GTC | TAT | GTC | CTG | CAG | CTC | ATA | 4896 |
| Val | Gly | Ser | Ala | Gln | Asp | Ser | Ile | Phe | Val | Tyr | Val | Leu | Gln | Leu | Ile | |
| | | | 1620 | | | | | 1625 | | | | | 1630 | | | |
| GAG | GGG | CTG | CAG | GTG | GTG | GGC | GGT | GGC | CGC | TAC | TTC | CCC | ACC | AAC | CAC | 4944 |
| Glu | Gly | Leu | Gln | Val | Val | Gly | Gly | Gly | Arg | Tyr | Phe | Pro | Thr | Asn | His | |
| | 1635 | | | | | 1640 | | | | | 1645 | | | | | |
| ACG | GTA | CAG | CTG | CAG | GCC | GTG | GTT | AGG | GAT | GGC | ACC | AAC | GTC | TCC | TAC | 4992 |
| Thr | Val | Gln | Leu | Gln | Ala | Val | Val | Arg | Asp | Gly | Thr | Asn | Val | Ser | Tyr | |
| | 1650 | | | | | 1655 | | | | | 1660 | | | | | |
| AGC | TGG | ACT | GCC | TGG | AGG | GAC | AGG | GGC | CCG | GCC | CTG | GCC | GGC | AGC | GGC | 5040 |
| Ser | Trp | Thr | Ala | Trp | Arg | Asp | Arg | Gly | Pro | Ala | Leu | Ala | Gly | Ser | Gly | |
| 1665 | | | | 1670 | | | | | 1675 | | | | | | 1680 | |
| AAA | GGC | TTC | TCG | CTC | ACC | GTG | CTC | GAG | GCC | GGC | ACC | TAC | CAT | GTG | CAG | 5088 |
| Lys | Gly | Phe | Ser | Leu | Thr | Val | Leu | Glu | Ala | Gly | Thr | Tyr | His | Val | Gln | |
| | | | | 1685 | | | | | 1690 | | | | | 1695 | | |
| CTG | CGG | GCC | ACC | AAC | ATG | CTG | GGC | AGC | GCC | TGG | GCC | GAC | TGC | ACC | ATG | 5136 |
| Leu | Arg | Ala | Thr | Asn | Met | Leu | Gly | Ser | Ala | Trp | Ala | Asp | Cys | Thr | Met | |
| | | | 1700 | | | | | 1705 | | | | | 1710 | | | |
| GAC | TTC | GTG | GAG | CCT | GTG | GGG | TGG | CTG | ATG | GTG | GCC | GCC | TCC | CCG | AAC | 5184 |
| Asp | Phe | Val | Glu | Pro | Val | Gly | Trp | Leu | Met | Val | Ala | Ala | Ser | Pro | Asn | |
| | | | 1715 | | | | | 1720 | | | | | 1725 | | | |
| CCA | GCT | GCC | GTC | AAC | ACA | AGC | GTC | ACC | CTC | AGT | GCC | GAG | CTG | GCT | GGT | 5232 |
| Pro | Ala | Ala | Val | Asn | Thr | Ser | Val | Thr | Leu | Ser | Ala | Glu | Leu | Ala | Gly | |
| | | 1730 | | | | | 1735 | | | | | 1740 | | | | |
| GGC | AGT | GGT | GTC | GTA | TAC | ACT | TGG | TCC | TTG | GAG | GAG | GGG | CTG | AGC | TGG | 5280 |
| Gly | Ser | Gly | Val | Val | Tyr | Thr | Trp | Ser | Leu | Glu | Glu | Gly | Leu | Ser | Trp | |
| 1745 | | | | 1750 | | | | | 1755 | | | | | | 1760 | |
| GAG | ACC | TCC | GAG | CCA | TTT | ACC | ACC | CAT | AGC | TTC | CCC | ACA | CCC | GGC | CTG | 5328 |
| Glu | Thr | Ser | Glu | Pro | Phe | Thr | Thr | His | Ser | Phe | Pro | Thr | Pro | Gly | Leu | |
| | | | | 1765 | | | | | 1770 | | | | | 1775 | | |
| CAC | TTG | GTC | ACC | ATG | ACG | GCA | GGG | AAC | CCG | CTG | GGC | TCA | GCC | AAC | GCC | 5376 |
| His | Leu | Val | Thr | Met | Thr | Ala | Gly | Asn | Pro | Leu | Gly | Ser | Ala | Asn | Ala | |
| | | | | 1780 | | | | | 1785 | | | | | 1790 | | |
| ACC | GTG | GAA | GTG | GAT | GTG | CAG | GTG | CCT | GTG | AGT | GGC | CTC | AGC | ATC | AGG | 5424 |
| Thr | Val | Glu | Val | Asp | Val | Gln | Val | Pro | Val | Ser | Gly | Leu | Ser | Ile | Arg | |
| | | | 1795 | | | | | 1800 | | | | | 1805 | | | |
| GCC | AGC | GAG | CCC | GGA | GGC | AGC | TTC | GTG | GCG | GCC | GGG | TCC | TCT | GTG | CCC | 5472 |
| Ala | Ser | Glu | Pro | Gly | Gly | Ser | Phe | Val | Ala | Ala | Gly | Ser | Ser | Val | Pro | |
| | 1810 | | | | | 1815 | | | | | 1820 | | | | | |

```
TTT  TGG  GGG  CAG  CTG  GCC  ACG  GGC  ACC  AAT  GTG  AGC  TGG  TGC  TGG  GCT          5520
Phe  Trp  Gly  Gln  Leu  Ala  Thr  Gly  Thr  Asn  Val  Ser  Trp  Cys  Trp  Ala
1825                1830                     1835                     1840

GTG  CCC  GGC  GGC  AGC  AGC  AAG  CGT  GGC  CCT  CAT  GTC  ACC  ATG  GTC  TTC          5568
Val  Pro  Gly  Gly  Ser  Ser  Lys  Arg  Gly  Pro  His  Val  Thr  Met  Val  Phe
                    1845                     1850                     1855

CCG  GAT  GCT  GGC  ACC  TTC  TCC  ATC  CGG  CTC  AAT  GCC  TCC  AAC  GCA  GTC          5616
Pro  Asp  Ala  Gly  Thr  Phe  Ser  Ile  Arg  Leu  Asn  Ala  Ser  Asn  Ala  Val
               1860                     1865                     1870

AGC  TGG  GTC  TCA  GCC  ACG  TAC  AAC  CTC  ACG  GCG  GAG  GAG  CCC  ATC  GTG          5664
Ser  Trp  Val  Ser  Ala  Thr  Tyr  Asn  Leu  Thr  Ala  Glu  Glu  Pro  Ile  Val
               1875                     1880                     1885

GGC  CTG  GTG  CTG  TGG  GCC  AGC  AGC  AAG  GTG  GTG  GCG  CCC  GGG  CAG  CTG          5712
Gly  Leu  Val  Leu  Trp  Ala  Ser  Ser  Lys  Val  Val  Ala  Pro  Gly  Gln  Leu
1890                1895                     1900

GTC  CAT  TTT  CAG  ATC  CTG  CTG  GCT  GCC  GGC  TCA  GCT  GTC  ACC  TTC  CGC          5760
Val  His  Phe  Gln  Ile  Leu  Leu  Ala  Ala  Gly  Ser  Ala  Val  Thr  Phe  Arg
1905                1910                     1915                     1920

CTA  CAG  GTC  GGC  GGG  GCC  AAC  CCC  GAG  GTG  CTC  CCC  GGG  CCC  CGT  TTC          5808
Leu  Gln  Val  Gly  Gly  Ala  Asn  Pro  Glu  Val  Leu  Pro  Gly  Pro  Arg  Phe
                    1925                     1930                     1935

TCC  CAC  AGC  TTC  CCC  CGC  GTC  GGA  GAC  CAC  GTG  GTG  AGC  GTG  CGG  GGC          5856
Ser  His  Ser  Phe  Pro  Arg  Val  Gly  Asp  His  Val  Val  Ser  Val  Arg  Gly
               1940                     1945                     1950

AAA  AAC  CAC  GTG  AGC  TGG  GCC  CAG  GCG  CAG  GTG  CGC  ATC  GTG  GTG  CTG          5904
Lys  Asn  His  Val  Ser  Trp  Ala  Gln  Ala  Gln  Val  Arg  Ile  Val  Val  Leu
               1955                     1960                     1965

GAG  GCC  GTG  AGT  GGG  CTG  CAG  GTG  CCC  AAC  TGC  TGC  GAG  CCT  GGC  ATC          5952
Glu  Ala  Val  Ser  Gly  Leu  Gln  Val  Pro  Asn  Cys  Cys  Glu  Pro  Gly  Ile
1970                1975                     1980

GCC  ACG  GGC  ACT  GAG  AGG  AAC  TTC  ACA  GCC  CGC  GTG  CAG  CGC  GGC  TCT          6000
Ala  Thr  Gly  Thr  Glu  Arg  Asn  Phe  Thr  Ala  Arg  Val  Gln  Arg  Gly  Ser
1985                1990                     1995                     2000

CGG  GTC  GCC  TAC  GCC  TGG  TAC  TTC  TCG  CTG  CAG  AAG  GTC  CAG  GGC  GAC          6048
Arg  Val  Ala  Tyr  Ala  Trp  Tyr  Phe  Ser  Leu  Gln  Lys  Val  Gln  Gly  Asp
                    2005                     2010                     2015

TCG  CTG  GTC  ATC  CTG  TCG  GGC  CGC  GAC  GTC  ACC  TAC  ACG  CCC  GTG  GCC          6096
Ser  Leu  Val  Ile  Leu  Ser  Gly  Arg  Asp  Val  Thr  Tyr  Thr  Pro  Val  Ala
               2020                     2025                     2030

GCG  GGG  CTG  TTG  GAG  ATC  CAG  GTG  CGC  GCC  TTC  AAC  GCC  CTG  GGC  AGT          6144
Ala  Gly  Leu  Leu  Glu  Ile  Gln  Val  Arg  Ala  Phe  Asn  Ala  Leu  Gly  Ser
               2035                     2040                     2045

GAG  AAC  CGC  ACG  CTG  GTG  CTG  GAG  GTT  CAG  GAC  GCC  GTC  CAG  TAT  GTG          6192
Glu  Asn  Arg  Thr  Leu  Val  Leu  Glu  Val  Gln  Asp  Ala  Val  Gln  Tyr  Val
               2050                     2055                     2060

GCC  CTG  CAG  AGC  GGC  CCC  TGC  TTC  ACC  AAC  CGC  TCG  GCG  CAG  TTT  GAG          6240
Ala  Leu  Gln  Ser  Gly  Pro  Cys  Phe  Thr  Asn  Arg  Ser  Ala  Gln  Phe  Glu
2065                2070                     2075                     2080

GCC  GCC  ACC  AGC  CCC  AGC  CCC  CGG  CGT  GTG  GCC  TAC  CAC  TGG  GAC  TTT          6288
Ala  Ala  Thr  Ser  Pro  Ser  Pro  Arg  Arg  Val  Ala  Tyr  His  Trp  Asp  Phe
                    2085                     2090                     2095

GGG  GAT  GGG  TCG  CCA  GGG  CAG  GAC  ACA  GAT  GAG  CCC  AGG  GCC  GAG  CAC          6336
Gly  Asp  Gly  Ser  Pro  Gly  Gln  Asp  Thr  Asp  Glu  Pro  Arg  Ala  Glu  His
               2100                     2105                     2110

TCC  TAC  CTG  AGG  CCT  GGG  GAC  TAC  CGC  GTG  CAG  GTG  AAC  GCC  TCC  AAC          6384
Ser  Tyr  Leu  Arg  Pro  Gly  Asp  Tyr  Arg  Val  Gln  Val  Asn  Ala  Ser  Asn
               2115                     2120                     2125

CTG  GTG  AGC  TTC  TTC  GTG  GCG  CAG  GCC  ACG  GTG  ACC  GTC  CAG  GTG  CTG          6432
Leu  Val  Ser  Phe  Phe  Val  Ala  Gln  Ala  Thr  Val  Thr  Val  Gln  Val  Leu
               2130                     2135                     2140
```

```
GCC  TGC  CGG  GAG  CCG  GAG  GTG  GAC  GTG  GTC  CTG  CCC  CTG  CAG  GTG  CTG     6480
Ala  Cys  Arg  Glu  Pro  Glu  Val  Asp  Val  Val  Leu  Pro  Leu  Gln  Val  Leu
2145                    2150                    2155                    2160

ATG  CGG  CGA  TCA  CAG  CGC  AAC  TAC  TTG  GAG  GCC  CAC  GTT  GAC  CTG  CGC     6528
Met  Arg  Arg  Ser  Gln  Arg  Asn  Tyr  Leu  Glu  Ala  His  Val  Asp  Leu  Arg
         2165                    2170                    2175

GAC  TGC  GTC  ACC  TAC  CAG  ACT  GAG  TAC  CGC  TGG  GAG  GTG  TAT  CGC  ACC     6576
Asp  Cys  Val  Thr  Tyr  Gln  Thr  Glu  Tyr  Arg  Trp  Glu  Val  Tyr  Arg  Thr
               2180                    2185                    2190

GCC  AGC  TGC  CAG  CGG  CCG  GGG  CGC  CCA  GCG  CGT  GTG  GCC  CTG  CCC  GGC     6624
Ala  Ser  Cys  Gln  Arg  Pro  Gly  Arg  Pro  Ala  Arg  Val  Ala  Leu  Pro  Gly
              2195                    2200                    2205

GTG  GAC  GTG  AGC  CGG  CCT  CGG  CTG  GTG  CTG  CCG  CGG  CTG  GCG  CTG  CCT     6672
Val  Asp  Val  Ser  Arg  Pro  Arg  Leu  Val  Leu  Pro  Arg  Leu  Ala  Leu  Pro
2210                    2215                    2220

GTG  GGG  CAC  TAC  TGC  TTT  GTG  TTT  GTC  GTG  TCA  TTT  GGG  GAC  ACG  CCA     6720
Val  Gly  His  Tyr  Cys  Phe  Val  Phe  Val  Val  Ser  Phe  Gly  Asp  Thr  Pro
2225                    2230                    2235                    2240

CTG  ACA  CAG  AGC  ATC  CAG  GCC  AAT  GTG  ACG  GTG  GCC  CCC  GAG  CGC  CTG     6768
Leu  Thr  Gln  Ser  Ile  Gln  Ala  Asn  Val  Thr  Val  Ala  Pro  Glu  Arg  Leu
          2245                    2250                    2255

GTG  CCC  ATC  ATT  GAG  GGT  GGC  TCA  TAC  CGC  GTG  TGG  TCA  GAC  ACA  CGG     6816
Val  Pro  Ile  Ile  Glu  Gly  Gly  Ser  Tyr  Arg  Val  Trp  Ser  Asp  Thr  Arg
               2260                    2265                    2270

GAC  CTG  GTG  CTG  GAT  GGG  AGC  GAG  TCC  TAC  GAC  CCC  AAC  CTG  GAG  GAC     6864
Asp  Leu  Val  Leu  Asp  Gly  Ser  Glu  Ser  Tyr  Asp  Pro  Asn  Leu  Glu  Asp
          2275                    2280                    2285

GGC  GAC  CAG  ACG  CCG  CTC  AGT  TTC  CAC  TGG  GCC  TGT  GTG  GCT  TCG  ACA     6912
Gly  Asp  Gln  Thr  Pro  Leu  Ser  Phe  His  Trp  Ala  Cys  Val  Ala  Ser  Thr
2290                    2295                    2300

CAG  AGG  GAG  GCT  GGC  GGG  TGT  GCG  CTG  AAC  TTT  GGG  CCC  CGC  GGG  AGC     6960
Gln  Arg  Glu  Ala  Gly  Gly  Cys  Ala  Leu  Asn  Phe  Gly  Pro  Arg  Gly  Ser
2305                    2310                    2315                    2320

AGC  ACG  GTC  ACC  ATT  CCA  CGG  GAG  CGG  CTG  GCG  GCT  GGC  GTG  GAG  TAC     7008
Ser  Thr  Val  Thr  Ile  Pro  Arg  Glu  Arg  Leu  Ala  Ala  Gly  Val  Glu  Tyr
               2325                    2330                    2335

ACC  TTC  AGC  CTG  ACC  GTG  TGG  AAG  GCC  GGC  CGC  AAG  GAG  GAG  GCC  ACC     7056
Thr  Phe  Ser  Leu  Thr  Val  Trp  Lys  Ala  Gly  Arg  Lys  Glu  Glu  Ala  Thr
          2340                    2345                    2350

AAC  CAG  ACG  GTG  CTG  ATC  CGG  AGT  GGC  CGG  GTG  CCC  ATT  GTG  TCC  TTG     7104
Asn  Gln  Thr  Val  Leu  Ile  Arg  Ser  Gly  Arg  Val  Pro  Ile  Val  Ser  Leu
          2355                    2360                    2365

GAG  TGT  GTG  TCC  TGC  AAG  GCA  CAG  GCC  GTG  TAC  GAA  GTG  AGC  CGC  AGC     7152
Glu  Cys  Val  Ser  Cys  Lys  Ala  Gln  Ala  Val  Tyr  Glu  Val  Ser  Arg  Ser
2370                    2375                    2380

TCC  TAC  GTG  TAC  TTG  GAG  GGC  CGC  TGC  CTC  AAT  TGC  AGC  AGC  GGC  TCC     7200
Ser  Tyr  Val  Tyr  Leu  Glu  Gly  Arg  Cys  Leu  Asn  Cys  Ser  Ser  Gly  Ser
2385                    2390                    2395                    2400

AAG  CGA  GGG  CGG  TGG  GCT  GCA  CGT  ACG  TTC  AGC  AAC  AAG  ACG  CTG  GTG     7248
Lys  Arg  Gly  Arg  Trp  Ala  Ala  Arg  Thr  Phe  Ser  Asn  Lys  Thr  Leu  Val
               2405                    2410                    2415

CTG  GAT  GAG  ACC  ACC  ACA  TCC  ACG  GGC  AGT  GCA  GGC  ATG  CGA  CTG  GTG     7296
Leu  Asp  Glu  Thr  Thr  Thr  Ser  Thr  Gly  Ser  Ala  Gly  Met  Arg  Leu  Val
          2420                    2425                    2430

CTG  CGG  CGG  GGC  GTG  CTG  CGG  GAC  GGC  GAG  GGA  TAC  ACC  TTC  ACG  CTC     7344
Leu  Arg  Arg  Gly  Val  Leu  Arg  Asp  Gly  Glu  Gly  Tyr  Thr  Phe  Thr  Leu
                2435                    2440                    2445

ACG  GTG  CTG  GGC  CGC  TCT  GGC  GAG  GAG  GAG  GGC  TGC  GCC  TCC  ATC  CGC     7392
Thr  Val  Leu  Gly  Arg  Ser  Gly  Glu  Glu  Glu  Gly  Cys  Ala  Ser  Ile  Arg
2450                    2455                    2460
```

```
CTG TCC CCC AAC CGC CCG CCG CTG GGG GGC TCT TGC CGC CTC TTC CCA    7440
Leu Ser Pro Asn Arg Pro Pro Leu Gly Gly Ser Cys Arg Leu Phe Pro
2465             2470                2475                2480

CTG GGC GCT GTG CAC GCC CTC ACC ACC AAG GTG CAC TTC GAA TGC ACG    7488
Leu Gly Ala Val His Ala Leu Thr Thr Lys Val His Phe Glu Cys Thr
            2485                2490                2495

GGC TGG CAT GAC GCG GAG GAT GCT GGC GCC CCG CTG GTG TAC GCC CTG    7536
Gly Trp His Asp Ala Glu Asp Ala Gly Ala Pro Leu Val Tyr Ala Leu
        2500                2505                2510

CTG CTG CGG CGC TGT CGC CAG GGC CAC TGC GAG GAG TTC TGT GTC TAC    7584
Leu Leu Arg Arg Cys Arg Gln Gly His Cys Glu Glu Phe Cys Val Tyr
2515                2520                2525

AAG GGC AGC CTC TCC AGC TAC GGA GCC GTG CTG CCC CCG GGT TTC AGG    7632
Lys Gly Ser Leu Ser Ser Tyr Gly Ala Val Leu Pro Pro Gly Phe Arg
2530                2535                2540

CCA CAC TTC GAG GTG GGC CTG GCC GTG GTG GTG CAG GAC CAG CTG GGA    7680
Pro His Phe Glu Val Gly Leu Ala Val Val Val Gln Asp Gln Leu Gly
2545                2550                2555                2560

GCC GCT GTG GTC GCC CTC AAC AGG TCT TTG GCC ATC ACC CTC CCA GAG    7728
Ala Ala Val Val Ala Leu Asn Arg Ser Leu Ala Ile Thr Leu Pro Glu
            2565                2570                2575

CCC AAC GGC AGC GCA ACG GGG CTC ACA GTC TGG CTG CAC GGG CTC ACC    7776
Pro Asn Gly Ser Ala Thr Gly Leu Thr Val Trp Leu His Gly Leu Thr
        2580                2585                2590

GCT AGT GTG CTC CCA GGG CTG CTG CGG CAG GCC GAT CCC CAG CAC GTC    7824
Ala Ser Val Leu Pro Gly Leu Leu Arg Gln Ala Asp Pro Gln His Val
    2595                2600                2605

ATC GAG TAC TCG TTG GCC CTG GTC ACC GTG CTG AAC GAG TAC GAG CGG    7872
Ile Glu Tyr Ser Leu Ala Leu Val Thr Val Leu Asn Glu Tyr Glu Arg
2610                2615                2620

GCC CTG GAC GTG GCG GCA GAG CCC AAG CAC GAG CGG CAG CAC CGA GCC    7920
Ala Leu Asp Val Ala Ala Glu Pro Lys His Glu Arg Gln His Arg Ala
2625                2630                2635                2640

CAG ATA CGC AAG AAC ATC ACG GAG ACT CTG GTG TCC CTG AGG GTC CAC    7968
Gln Ile Arg Lys Asn Ile Thr Glu Thr Leu Val Ser Leu Arg Val His
            2645                2650                2655

ACT GTG GAT GAC ATC CAG CAG ATC GCT GCT GCG CTG GCC CAG TGC ATG    8016
Thr Val Asp Asp Ile Gln Gln Ile Ala Ala Ala Leu Ala Gln Cys Met
        2660                2665                2670

GGG CCC AGC AGG GAG CTC GTA TGC CGC TCG TGC CTG AAG CAG ACG CTG    8064
Gly Pro Ser Arg Glu Leu Val Cys Arg Ser Cys Leu Lys Gln Thr Leu
    2675                2680                2685

CAC AAG CTG GAG GCC ATG ATG CTC ATC CTG CAG GCA GAG ACC ACC GCG    8112
His Lys Leu Glu Ala Met Met Leu Ile Leu Gln Ala Glu Thr Thr Ala
2690                2695                2700

GGC ACC GTG ACG CCC ACC GCC ATC GGA GAC AGC ATC CTC AAC ATC ACA    8160
Gly Thr Val Thr Pro Thr Ala Ile Gly Asp Ser Ile Leu Asn Ile Thr
2705                2710                2715                2720

GGA GAC CTC ATC CAC CTG GCC AGC TCG GAC GTG CGG GCA CCA CAG CCC    8208
Gly Asp Leu Ile His Leu Ala Ser Ser Asp Val Arg Ala Pro Gln Pro
            2725                2730                2735

TCA GAG CTG GGA GCC GAG TCA CCA TCT CGG ATG GTG GCG TCC CAG GCC    8256
Ser Glu Leu Gly Ala Glu Ser Pro Ser Arg Met Val Ala Ser Gln Ala
        2740                2745                2750

TAC AAC CTG ACC TCT GCC CTC ATG CGC ATC CTC ATG CGC TCC CGC GTG    8304
Tyr Asn Leu Thr Ser Ala Leu Met Arg Ile Leu Met Arg Ser Arg Val
    2755                2760                2765

CTC AAC GAG GAG CCC CTG ACG CTG GCG GGC GAG GAG ATC GTG GCC CAG    8352
Leu Asn Glu Glu Pro Leu Thr Leu Ala Gly Glu Glu Ile Val Ala Gln
2770                2775                2780
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| GGC | AAG | CGC | TCG | GAC | CCG | CGG | AGC | CTG | CTG | TGC | TAT | GGC | GGC | GCC | CCA | 8400 |
| Gly | Lys | Arg | Ser | Asp | Pro | Arg | Ser | Leu | Leu | Cys | Tyr | Gly | Gly | Ala | Pro |      |
| 2785 |   |   |   | 2790 |   |   |   | 2795 |   |   |   |   |   |   | 2800 |   |

| GGG | CCT | GGC | TGC | CAC | TTC | TCC | ATC | CCC | GAG | GCT | TTC | AGC | GGG | GCC | CTG | 8448 |
| --- | --- | --- | --- | --- | --- | --- | --- | --- | --- | --- | --- | --- | --- | --- | --- | ---- |
| Gly | Pro | Gly | Cys | His | Phe | Ser | Ile | Pro | Glu | Ala | Phe | Ser | Gly | Ala | Leu |      |
|     |     |     |     | 2805 |   |   |   |   | 2810 |   |   |   |   |   | 2815 |   |

| GCC | AAC | CTC | AGT | GAC | GTG | GTG | CAG | CTC | ATC | TTT | CTG | GTG | GAC | TCC | AAT | 8496 |
| --- | --- | --- | --- | --- | --- | --- | --- | --- | --- | --- | --- | --- | --- | --- | --- | ---- |
| Ala | Asn | Leu | Ser | Asp | Val | Val | Gln | Leu | Ile | Phe | Leu | Val | Asp | Ser | Asn |      |
|     |     |     | 2820 |   |   |   |   | 2825 |   |   |   |   | 2830 |   |   |   |

| CCC | TTT | CCC | TTT | GGC | TAT | ATC | AGC | AAC | TAC | ACC | GTC | TCC | ACC | AAG | GTG | 8544 |
| --- | --- | --- | --- | --- | --- | --- | --- | --- | --- | --- | --- | --- | --- | --- | --- | ---- |
| Pro | Phe | Pro | Phe | Gly | Tyr | Ile | Ser | Asn | Tyr | Thr | Val | Ser | Thr | Lys | Val |      |
|     |     | 2835 |   |   |   |   | 2840 |   |   |   |   | 2845 |   |   |   |   |

| GCC | TCG | ATG | GCA | TTC | CAG | ACA | CAG | GCC | GGC | GCC | CAG | ATC | CCC | ATC | GAG | 8592 |
| --- | --- | --- | --- | --- | --- | --- | --- | --- | --- | --- | --- | --- | --- | --- | --- | ---- |
| Ala | Ser | Met | Ala | Phe | Gln | Thr | Gln | Ala | Gly | Ala | Gln | Ile | Pro | Ile | Glu |      |
|     | 2850 |   |   |   |   | 2855 |   |   |   |   | 2860 |   |   |   |   |   |

| CGG | CTG | GCC | TCA | GAG | CGC | GCC | ATC | ACC | GTG | AAG | GTG | CCC | AAC | AAC | TCG | 8640 |
| --- | --- | --- | --- | --- | --- | --- | --- | --- | --- | --- | --- | --- | --- | --- | --- | ---- |
| Arg | Leu | Ala | Ser | Glu | Arg | Ala | Ile | Thr | Val | Lys | Val | Pro | Asn | Asn | Ser |      |
| 2865 |   |   |   |   | 2870 |   |   |   |   | 2875 |   |   |   |   | 2880 |   |

| GAC | TGG | GCT | GCC | CGG | GGC | CAC | CGC | AGC | TCC | GCC | AAC | TCC | GCC | AAC | TCC | 8688 |
| --- | --- | --- | --- | --- | --- | --- | --- | --- | --- | --- | --- | --- | --- | --- | --- | ---- |
| Asp | Trp | Ala | Ala | Arg | Gly | His | Arg | Ser | Ser | Ala | Asn | Ser | Ala | Asn | Ser |      |
|     |     |     |     | 2885 |   |   |   |   | 2890 |   |   |   |   | 2895 |   |   |

| GTT | GTG | GTC | CAG | CCC | CAG | GCC | TCC | GTC | GGT | GCT | GTG | GTC | ACC | CTG | GAC | 8736 |
| --- | --- | --- | --- | --- | --- | --- | --- | --- | --- | --- | --- | --- | --- | --- | --- | ---- |
| Val | Val | Val | Gln | Pro | Gln | Ala | Ser | Val | Gly | Ala | Val | Val | Thr | Leu | Asp |      |
|     |     |     |     | 2900 |   |   |   |   | 2905 |   |   |   |   | 2910 |   |   |

| AGC | AGC | AAC | CCT | GCG | GCC | GGG | CTG | CAT | CTG | CAG | CTC | AAC | TAT | ACG | CTG | 8784 |
| --- | --- | --- | --- | --- | --- | --- | --- | --- | --- | --- | --- | --- | --- | --- | --- | ---- |
| Ser | Ser | Asn | Pro | Ala | Ala | Gly | Leu | His | Leu | Gln | Leu | Asn | Tyr | Thr | Leu |      |
|     |     |     | 2915 |   |   |   |   | 2920 |   |   |   |   | 2925 |   |   |   |

| CTG | GAC | GGC | CAC | TAC | CTG | TCT | GAG | GAA | CCT | GAG | CCC | TAC | CTG | GCA | GTC | 8832 |
| --- | --- | --- | --- | --- | --- | --- | --- | --- | --- | --- | --- | --- | --- | --- | --- | ---- |
| Leu | Asp | Gly | His | Tyr | Leu | Ser | Glu | Glu | Pro | Glu | Pro | Tyr | Leu | Ala | Val |      |
|     |     | 2930 |   |   |   |   | 2935 |   |   |   |   | 2940 |   |   |   |   |

| TAC | CTA | CAC | TCG | GAG | CCC | CGG | CCC | AAT | GAG | CAC | AAC | TGC | TCG | GCT | AGC | 8880 |
| --- | --- | --- | --- | --- | --- | --- | --- | --- | --- | --- | --- | --- | --- | --- | --- | ---- |
| Tyr | Leu | His | Ser | Glu | Pro | Arg | Pro | Asn | Glu | His | Asn | Cys | Ser | Ala | Ser |      |
| 2945 |   |   |   |   | 2950 |   |   |   |   | 2955 |   |   |   |   | 2960 |   |

| AGG | AGG | ATC | CGC | CCA | GAG | TCA | CTC | CAG | GGT | GCT | GAC | CAC | CGG | CCC | TAC | 8928 |
| --- | --- | --- | --- | --- | --- | --- | --- | --- | --- | --- | --- | --- | --- | --- | --- | ---- |
| Arg | Arg | Ile | Arg | Pro | Glu | Ser | Leu | Gln | Gly | Ala | Asp | His | Arg | Pro | Tyr |      |
|     |     |     |     | 2965 |   |   |   |   | 2970 |   |   |   |   | 2975 |   |   |

| ACC | TTC | TTC | ATT | TCC | CCG | GGG | AGC | AGA | GAC | CCA | GCG | GGG | AGT | TAC | CAT | 8976 |
| --- | --- | --- | --- | --- | --- | --- | --- | --- | --- | --- | --- | --- | --- | --- | --- | ---- |
| Thr | Phe | Phe | Ile | Ser | Pro | Gly | Ser | Arg | Asp | Pro | Ala | Gly | Ser | Tyr | His |      |
|     |     |     | 2980 |   |   |   |   | 2985 |   |   |   |   | 2990 |   |   |   |

| CTG | AAC | CTC | TCC | AGC | CAC | TTC | CGC | TGG | TCG | GCG | CTG | CAG | GTG | TCC | GTG | 9024 |
| --- | --- | --- | --- | --- | --- | --- | --- | --- | --- | --- | --- | --- | --- | --- | --- | ---- |
| Leu | Asn | Leu | Ser | Ser | His | Phe | Arg | Trp | Ser | Ala | Leu | Gln | Val | Ser | Val |      |
|     |     |     | 2995 |   |   |   |   | 3000 |   |   |   |   | 3005 |   |   |   |

| GGC | CTG | TAC | ACG | TCC | CTG | TGC | CAG | TAC | TTC | AGC | GAG | GAG | GAC | ATG | GTG | 9072 |
| --- | --- | --- | --- | --- | --- | --- | --- | --- | --- | --- | --- | --- | --- | --- | --- | ---- |
| Gly | Leu | Tyr | Thr | Ser | Leu | Cys | Gln | Tyr | Phe | Ser | Glu | Glu | Asp | Met | Val |      |
|     |     | 3010 |   |   |   |   | 3015 |   |   |   |   | 3020 |   |   |   |   |

| TGG | CGG | ACA | GAG | GGG | CTG | CTG | CCC | CTG | GAG | GAG | ACC | TCG | CCC | CGC | CAG | 9120 |
| --- | --- | --- | --- | --- | --- | --- | --- | --- | --- | --- | --- | --- | --- | --- | --- | ---- |
| Trp | Arg | Thr | Glu | Gly | Leu | Leu | Pro | Leu | Glu | Glu | Thr | Ser | Pro | Arg | Gln |      |
| 3025 |   |   |   |   | 3030 |   |   |   |   | 3035 |   |   |   |   | 3040 |   |

| GCC | GTC | TGC | CTC | ACC | CGC | CAC | CTC | ACC | GCC | TTC | GGC | GCC | AGC | CTC | TTC | 9168 |
| --- | --- | --- | --- | --- | --- | --- | --- | --- | --- | --- | --- | --- | --- | --- | --- | ---- |
| Ala | Val | Cys | Leu | Thr | Arg | His | Leu | Thr | Ala | Phe | Gly | Ala | Ser | Leu | Phe |      |
|     |     |     |     | 3045 |   |   |   |   | 3050 |   |   |   |   | 3055 |   |   |

| GTG | CCC | CCA | AGC | CAT | GTC | CGC | TTT | GTG | TTT | CCT | GAG | CCG | ACA | GCG | GAT | 9216 |
| --- | --- | --- | --- | --- | --- | --- | --- | --- | --- | --- | --- | --- | --- | --- | --- | ---- |
| Val | Pro | Pro | Ser | His | Val | Arg | Phe | Val | Phe | Pro | Glu | Pro | Thr | Ala | Asp |      |
|     |     |     | 3060 |   |   |   |   | 3065 |   |   |   |   | 3070 |   |   |   |

| GTA | AAC | TAC | ATC | GTC | ATG | CTG | ACA | TGT | GCT | GTG | TGC | CTG | GTG | ACC | TAC | 9264 |
| --- | --- | --- | --- | --- | --- | --- | --- | --- | --- | --- | --- | --- | --- | --- | --- | ---- |
| Val | Asn | Tyr | Ile | Val | Met | Leu | Thr | Cys | Ala | Val | Cys | Leu | Val | Thr | Tyr |      |
|     |     |     | 3075 |   |   |   |   | 3080 |   |   |   |   | 3085 |   |   |   |

| ATG | GTC | ATG | GCC | GCC | ATC | CTG | CAC | AAG | CTG | GAC | CAG | TTG | GAT | GCC | AGC | 9312 |
| --- | --- | --- | --- | --- | --- | --- | --- | --- | --- | --- | --- | --- | --- | --- | --- | ---- |
| Met | Val | Met | Ala | Ala | Ile | Leu | His | Lys | Leu | Asp | Gln | Leu | Asp | Ala | Ser |      |
|     |     | 3090 |   |   |   |   | 3095 |   |   |   |   | 3100 |   |   |   |   |

```
CGG GGC CGC GCC ATC CCT TTC TGT GGG CAG CGG GGC CGC TTC AAG TAC     9360
Arg Gly Arg Ala Ile Pro Phe Cys Gly Gln Arg Gly Arg Phe Lys Tyr
3105            3110                3115                3120

GAG ATC CTC GTC AAG ACA GGC TGG GGC CGG GGC TCA GGT ACC ACG GCC     9408
Glu Ile Leu Val Lys Thr Gly Trp Gly Arg Gly Ser Gly Thr Thr Ala
        3125                3130                3135

CAC GTG GGC ATC ATG CTG TAT GGG GTG GAC AGC CGG AGC GGC CAC CGG     9456
His Val Gly Ile Met Leu Tyr Gly Val Asp Ser Arg Ser Gly His Arg
                3140                3145                3150

CAC CTG GAC GGC GAC AGA GCC TTC CAC CGC AAC AGC CTG GAC ATC TTC     9504
His Leu Asp Gly Asp Arg Ala Phe His Arg Asn Ser Leu Asp Ile Phe
            3155                3160                3165

CGG ATC GCC ACC CCG CAC AGC CTG GGT AGC GTG TGG AAG ATC CGA GTG     9552
Arg Ile Ala Thr Pro His Ser Leu Gly Ser Val Trp Lys Ile Arg Val
    3170                3175                3180

TGG CAC GAC AAC AAA GGG CTC AGC CCT GCC TGG TTC CTG CAG CAC GTC     9600
Trp His Asp Asn Lys Gly Leu Ser Pro Ala Trp Phe Leu Gln His Val
3185            3190                3195                3200

ATC GTC AGG GAC CTG CAG ACG GCA CGC AGC GCC TTC TTC CTG GTC AAT     9648
Ile Val Arg Asp Leu Gln Thr Ala Arg Ser Ala Phe Phe Leu Val Asn
                3205                3210                3215

GAC TGG CTT TCG GTG GAG ACG GAG GCC AAC GGG GGC CTG GTG GAG AAG     9696
Asp Trp Leu Ser Val Glu Thr Glu Ala Asn Gly Gly Leu Val Glu Lys
            3220                3225                3230

GAG GTG CTG GCC GCG AGC GAC GCA GCC CTT TTG CGC TTC CGG CGC CTG     9744
Glu Val Leu Ala Ala Ser Asp Ala Ala Leu Leu Arg Phe Arg Arg Leu
    3235                3240                3245

CTG GTG GCT GAG CTG CAG CGT GGC TTC TTT GAC AAG CAC ATC TGG CTC     9792
Leu Val Ala Glu Leu Gln Arg Gly Phe Phe Asp Lys His Ile Trp Leu
3250            3255                3260

TCC ATA TGG GAC CGG CCG CCT CGT AGC CGT TTC ACT CGC ATC CAG AGG     9840
Ser Ile Trp Asp Arg Pro Pro Arg Ser Arg Phe Thr Arg Ile Gln Arg
3265            3270                3275                3280

GCC ACC TGC TGC GTT CTC CTC ATC TGC CTC TTC CTG GGC GCC AAC GCC     9888
Ala Thr Cys Cys Val Leu Leu Ile Cys Leu Phe Leu Gly Ala Asn Ala
                3285                3290                3295

GTG TGG TAC GGG GCT GTT GGC GAC TCT GCC TAC AGC ACG GGG CAT GTG     9936
Val Trp Tyr Gly Ala Val Gly Asp Ser Ala Tyr Ser Thr Gly His Val
            3300                3305                3310

TCC AGG CTG AGC CCG CTG AGC GTC GAC ACA GTC GCT GTT GGC CTG GTG     9984
Ser Arg Leu Ser Pro Leu Ser Val Asp Thr Val Ala Val Gly Leu Val
    3315                3320                3325

TCC AGC GTG GTT GTC TAT CCC GTC TAC CTG GCC ATC CTT TTT CTC TTC     10032
Ser Ser Val Val Val Tyr Pro Val Tyr Leu Ala Ile Leu Phe Leu Phe
3330            3335                3340

CGG ATG TCC CGG AGC AAG GTG GCT GGG AGC CCG AGC CCC ACA CCT GCC     10080
Arg Met Ser Arg Ser Lys Val Ala Gly Ser Pro Ser Pro Thr Pro Ala
3345            3350                3355                3360

GGG CAG CAG GTG CTG GAC ATC GAC AGC TGC CTG GAC TCG TCC GTG CTG     10128
Gly Gln Gln Val Leu Asp Ile Asp Ser Cys Leu Asp Ser Ser Val Leu
                3365                3370                3375

GAC AGC TCC TTC CTC ACG TTC TCA GGC CTC CAC GCT GAG CAG GCC TTT     10176
Asp Ser Ser Phe Leu Thr Phe Ser Gly Leu His Ala Glu Gln Ala Phe
            3380                3385                3390

GTT GGA CAG ATG AAG AGT GAC TTG TTT CTG GAT GAT TCT AAG AGT CTG     10224
Val Gly Gln Met Lys Ser Asp Leu Phe Leu Asp Asp Ser Lys Ser Leu
    3395                3400                3405

GTG TGC TGG CCC TCC GGC GAG GGA ACG CTC AGT TGG CCG GAC CTG CTC     10272
Val Cys Trp Pro Ser Gly Glu Gly Thr Leu Ser Trp Pro Asp Leu Leu
3410            3415                3420
```

```
AGT GAC CCG TCC ATT GTG GGT AGC AAT CTG CGG CAG CTG GCA CGG GGC       10320
Ser Asp Pro Ser Ile Val Gly Ser Asn Leu Arg Gln Leu Ala Arg Gly
3425        3430                3435                3440

CAG GCG GGC CAT GGG CTG GGC CCA GAG GAG GAC GGC TTC TCC CTG GCC       10368
Gln Ala Gly His Gly Leu Gly Pro Glu Glu Asp Gly Phe Ser Leu Ala
            3445                3450                3455

AGC CCC TAC TCG CCT GCC AAA TCC TTC TCA GCA TCA GAT GAA GAC CTG       10416
Ser Pro Tyr Ser Pro Ala Lys Ser Phe Ser Ala Ser Asp Glu Asp Leu
        3460                3465                3470

ATC CAG CAG GTC CTT GCC GAG GGG GTC AGC AGC CCA GCC CCT ACC CAA       10464
Ile Gln Gln Val Leu Ala Glu Gly Val Ser Ser Pro Ala Pro Thr Gln
3475                3480                3485

GAC ACC CAC ATG GAA ACG GAC CTG CTC AGC AGC CTG TCC AGC ACT CCT       10512
Asp Thr His Met Glu Thr Asp Leu Leu Ser Ser Leu Ser Ser Thr Pro
        3490                3495                3500

GGG GAG AAG ACA GAG ACG CTG GCG CTG CAG AGG CTG GGG GAG CTG GGG       10560
Gly Glu Lys Thr Glu Thr Leu Ala Leu Gln Arg Leu Gly Glu Leu Gly
3505                3510                3515                3520

CCA CCC AGC CCA GGC CTG AAC TGG GAA CAG CCC CAG GCA GCG AGG CTG       10608
Pro Pro Ser Pro Gly Leu Asn Trp Glu Gln Pro Gln Ala Ala Arg Leu
            3525                3530                3535

TCC AGG ACA GGA CTG GTG GAG GGT CTG CGG AAG CGC CTG CTG CCG GCC       10656
Ser Arg Thr Gly Leu Val Glu Gly Leu Arg Lys Arg Leu Leu Pro Ala
        3540                3545                3550

TGG TGT GCC TCC CTG GCC CAC GGG CTC AGC CTG CTC CTG GTG GCT GTG       10704
Trp Cys Ala Ser Leu Ala His Gly Leu Ser Leu Leu Leu Val Ala Val
3555                3560                3565

GCT GTG GCT GTC TCA GGG TGG GTG GGT GCG AGC TTC CCC CCG GGC GTG       10752
Ala Val Ala Val Ser Gly Trp Val Gly Ala Ser Phe Pro Pro Gly Val
            3570                3575                3580

AGT GTT GCG TGG CTC CTG TCC AGC AGC GCC AGC TTC CTG GCC TCA TTC       10800
Ser Val Ala Trp Leu Leu Ser Ser Ser Ala Ser Phe Leu Ala Ser Phe
3585                3590                3595                3600

CTC GGC TGG GAG CCA CTG AAG GTC TTG CTG GAA GCC CTG TAC TTC TCA       10848
Leu Gly Trp Glu Pro Leu Lys Val Leu Leu Glu Ala Leu Tyr Phe Ser
            3605                3610                3615

CTG GTG GCC AAG CGG CTG CAC CCG GAT GAA GAT GAC ACC CTG GTA GAG       10896
Leu Val Ala Lys Arg Leu His Pro Asp Glu Asp Asp Thr Leu Val Glu
        3620                3625                3630

AGC CCG GCT GTG ACG CCT GTG AGC GCA CGT GTG CCC CGC GTA CGG CCA       10944
Ser Pro Ala Val Thr Pro Val Ser Ala Arg Val Pro Arg Val Arg Pro
            3635                3640                3645

CCC CAC GGC TTT GCA CTC TTC CTG GCC AAG GAA GAA GCC CGC AAG GTC       10992
Pro His Gly Phe Ala Leu Phe Leu Ala Lys Glu Glu Ala Arg Lys Val
        3650                3655                3660

AAG AGG CTA CAT GGC ATG CTG CGG AGC CTC CTG GTG TAC ATG CTT TTT       11040
Lys Arg Leu His Gly Met Leu Arg Ser Leu Leu Val Tyr Met Leu Phe
3665                3670                3675                3680

CTG CTG GTG ACC CTG CTG GCC AGC TAT GGG GAT GCC TCA TGC CAT GGG       11088
Leu Leu Val Thr Leu Leu Ala Ser Tyr Gly Asp Ala Ser Cys His Gly
            3685                3690                3695

CAC GCC TAC CGT CTG CAA AGC GCC ATC AAG CAG GAG CTG CAC AGC CGG       11136
His Ala Tyr Arg Leu Gln Ser Ala Ile Lys Gln Glu Leu His Ser Arg
        3700                3705                3710

GCC TTC CTG GCC ATC ACG CGG TCT GAG GAG CTC TGG CCA TGG ATG GCC       11184
Ala Phe Leu Ala Ile Thr Arg Ser Glu Glu Leu Trp Pro Trp Met Ala
            3715                3720                3725

CAC GTG CTG CTG CCC TAC GTC CAC GGG AAC CAG TCC AGC CCA GAG CTG       11232
His Val Leu Leu Pro Tyr Val His Gly Asn Gln Ser Ser Pro Glu Leu
        3730                3735                3740
```

| | | | | | | | | | | | | | | | | |
|---|---|---|---|---|---|---|---|---|---|---|---|---|---|---|---|---|
| GGG | CCC | CCA | CGG | CTG | CGG | CAG | GTG | CGG | CTG | CAG | GAA | GCA | CTC | TAC | CCA | 11280 |
| Gly | Pro | Pro | Arg | Leu | Arg | Gln | Val | Arg | Leu | Gln | Glu | Ala | Leu | Tyr | Pro | |
| 3745 | | | | 3750 | | | | | 3755 | | | | | | 3760 | |
| GAC | CCT | CCC | GGC | CCC | AGG | GTC | CAC | ACG | TGC | TCG | GCC | GCA | GGA | GGC | TTC | 11328 |
| Asp | Pro | Pro | Gly | Pro | Arg | Val | His | Thr | Cys | Ser | Ala | Ala | Gly | Gly | Phe | |
| | | | | 3765 | | | | | 3770 | | | | | | 3775 | |
| AGC | ACC | AGC | GAT | TAC | GAC | GTT | GGC | TGG | GAG | AGT | CCT | CAC | AAT | GGC | TCG | 11376 |
| Ser | Thr | Ser | Asp | Tyr | Asp | Val | Gly | Trp | Glu | Ser | Pro | His | Asn | Gly | Ser | |
| | | | 3780 | | | | | 3785 | | | | | | 3790 | | |
| GGG | ACG | TGG | GCC | TAT | TCA | GCG | CCG | GAT | CTG | CTG | GGG | GCA | TGG | TCC | TGG | 11424 |
| Gly | Thr | Trp | Ala | Tyr | Ser | Ala | Pro | Asp | Leu | Leu | Gly | Ala | Trp | Ser | Trp | |
| | | | 3795 | | | | | 3800 | | | | | | 3805 | | |
| GGC | TCC | TGT | GCC | GTG | TAT | GAC | AGC | GGG | GGC | TAC | GTG | CAG | GAG | CTG | GGC | 11472 |
| Gly | Ser | Cys | Ala | Val | Tyr | Asp | Ser | Gly | Gly | Tyr | Val | Gln | Glu | Leu | Gly | |
| | | 3810 | | | | | 3815 | | | | | 3820 | | | | |
| CTG | AGC | CTG | GAG | GAG | AGC | CGC | GAC | CGG | CTG | CGC | TTC | CTG | CAG | CTG | CAC | 11520 |
| Leu | Ser | Leu | Glu | Glu | Ser | Arg | Asp | Arg | Leu | Arg | Phe | Leu | Gln | Leu | His | |
| 3825 | | | | | 3830 | | | | | 3835 | | | | | 3840 | |
| AAC | TGG | CTG | GAC | AAC | AGG | AGC | CGC | GCT | GTG | TTC | CTG | GAG | CTC | ACG | CGC | 11568 |
| Asn | Trp | Leu | Asp | Asn | Arg | Ser | Arg | Ala | Val | Phe | Leu | Glu | Leu | Thr | Arg | |
| | | | | 3845 | | | | | 3850 | | | | | | 3855 | |
| TAC | AGC | CCG | GCC | GTG | GGG | CTG | CAC | GCC | GCC | GTC | ACG | CTG | CGC | CTC | GAG | 11616 |
| Tyr | Ser | Pro | Ala | Val | Gly | Leu | His | Ala | Ala | Val | Thr | Leu | Arg | Leu | Glu | |
| | | | | 3860 | | | | | 3865 | | | | | 3870 | | |
| TTC | CCG | GCG | GCC | GGC | CGC | GCC | CTG | GCC | GCC | CTC | AGC | GTC | CGC | CCC | TTT | 11664 |
| Phe | Pro | Ala | Ala | Gly | Arg | Ala | Leu | Ala | Ala | Leu | Ser | Val | Arg | Pro | Phe | |
| | | | 3875 | | | | | 3880 | | | | | | 3885 | | |
| GCG | CTG | CGC | CGC | CTC | AGC | GCG | GGC | CTC | TCG | CTG | CCT | CTG | CTC | ACC | TCG | 11712 |
| Ala | Leu | Arg | Arg | Leu | Ser | Ala | Gly | Leu | Ser | Leu | Pro | Leu | Leu | Thr | Ser | |
| | | 3890 | | | | | 3895 | | | | | 3900 | | | | |
| GTG | TGC | CTG | CTG | CTG | TTC | GCC | GTG | CAC | TTC | GCC | GTG | GCC | GAG | GCC | CGT | 11760 |
| Val | Cys | Leu | Leu | Leu | Phe | Ala | Val | His | Phe | Ala | Val | Ala | Glu | Ala | Arg | |
| 3905 | | | | | 3910 | | | | | 3915 | | | | | 3920 | |
| ACT | TGG | CAC | AGG | GAA | GGG | CGC | TGG | CGC | GTG | CTG | CGG | CTC | GGA | GCC | TGG | 11808 |
| Thr | Trp | His | Arg | Glu | Gly | Arg | Trp | Arg | Val | Leu | Arg | Leu | Gly | Ala | Trp | |
| | | | | 3925 | | | | | 3930 | | | | | | 3935 | |
| GCG | CGG | TGG | CTG | CTG | GTG | GCG | CTG | ACG | GCG | GCC | ACG | GCA | CTG | GTA | CGC | 11856 |
| Ala | Arg | Trp | Leu | Leu | Val | Ala | Leu | Thr | Ala | Ala | Thr | Ala | Leu | Val | Arg | |
| | | | | 3940 | | | | | 3945 | | | | | 3950 | | |
| CTC | GCC | CAG | CTG | GGT | GCC | GCT | GAC | CGC | CAG | TGG | ACC | CGT | TTC | GTG | CGC | 11904 |
| Leu | Ala | Gln | Leu | Gly | Ala | Ala | Asp | Arg | Gln | Trp | Thr | Arg | Phe | Val | Arg | |
| | | 3955 | | | | | 3960 | | | | | 3965 | | | | |
| GGC | CGC | CCG | CGC | CGC | TTC | ACT | AGC | TTC | GAC | CAG | GTG | GCG | CAC | GTG | AGC | 11952 |
| Gly | Arg | Pro | Arg | Arg | Phe | Thr | Ser | Phe | Asp | Gln | Val | Ala | His | Val | Ser | |
| | | 3970 | | | | | 3975 | | | | | 3980 | | | | |
| TCC | GCA | GCC | CGT | GGC | CTG | GCG | GCC | TCG | CTG | CTC | TTC | CTG | CTT | TTG | GTC | 12000 |
| Ser | Ala | Ala | Arg | Gly | Leu | Ala | Ala | Ser | Leu | Leu | Phe | Leu | Leu | Leu | Val | |
| 3985 | | | | | 3990 | | | | | 3995 | | | | | 4000 | |
| AAG | GCT | GCC | CAG | CAC | GTA | CGC | TTC | GTG | CGC | CAG | TGG | TCC | GTC | TTT | GGC | 12048 |
| Lys | Ala | Ala | Gln | His | Val | Arg | Phe | Val | Arg | Gln | Trp | Ser | Val | Phe | Gly | |
| | | | | 4005 | | | | | 4010 | | | | | | 4015 | |
| AAG | ACA | TTA | TGC | CGA | GCT | CTG | CCA | GAG | CTC | CTG | GGG | GTC | ACC | TTG | GGC | 12096 |
| Lys | Thr | Leu | Cys | Arg | Ala | Leu | Pro | Glu | Leu | Leu | Gly | Val | Thr | Leu | Gly | |
| | | | | 4020 | | | | | 4025 | | | | | 4030 | | |
| CTG | GTG | GTG | CTC | GGG | GTA | GCC | TAC | GCC | CAG | CTG | GCC | ATC | CTG | CTC | GTG | 12144 |
| Leu | Val | Val | Leu | Gly | Val | Ala | Tyr | Ala | Gln | Leu | Ala | Ile | Leu | Leu | Val | |
| | | | 4035 | | | | | 4040 | | | | | 4045 | | | |
| TCT | TCC | TGT | GTG | GAC | TCC | CTC | TGG | AGC | GTG | GCC | CAG | GCC | CTG | TTG | GTG | 12192 |
| Ser | Ser | Cys | Val | Asp | Ser | Leu | Trp | Ser | Val | Ala | Gln | Ala | Leu | Leu | Val | |
| | | | 4050 | | | | | 4055 | | | | | 4060 | | | |

```
CTG  TGC  CCT  GGG  ACT  GGG  CTC  TCT  ACC  CTG  TGT  CCT  GCC  GAG  TCC  TGG      12240
Leu  Cys  Pro  Gly  Thr  Gly  Leu  Ser  Thr  Leu  Cys  Pro  Ala  Glu  Ser  Trp
4065                4070                4075                     4080

CAC  CTG  TCA  CCC  CTG  CTG  TGT  GTG  GGG  CTC  TGG  GCA  CTG  CGG  CTG  TGG      12288
His  Leu  Ser  Pro  Leu  Leu  Cys  Val  Gly  Leu  Trp  Ala  Leu  Arg  Leu  Trp
               4085                4090                     4095

GGC  GCC  CTA  CGG  CTG  GGG  GCT  GTT  ATT  CTC  CGC  TGG  CGC  TAC  CAC  GCC      12336
Gly  Ala  Leu  Arg  Leu  Gly  Ala  Val  Ile  Leu  Arg  Trp  Arg  Tyr  His  Ala
          4100                4105                     4110

TTG  CGT  GGA  GAG  CTG  TAC  CGG  CCG  GCC  TGG  GAG  CCC  CAG  GAC  TAC  GAG      12384
Leu  Arg  Gly  Glu  Leu  Tyr  Arg  Pro  Ala  Trp  Glu  Pro  Gln  Asp  Tyr  Glu
          4115                4120                     4125

ATG  GTG  GAG  TTG  TTC  CTG  CGC  AGG  CTG  CGC  CTC  TGG  ATG  GGC  CTC  AGC      12432
Met  Val  Glu  Leu  Phe  Leu  Arg  Arg  Leu  Arg  Leu  Trp  Met  Gly  Leu  Ser
4130                4135                     4140

AAG  GTC  AAG  GAG  TTC  CGC  CAC  AAA  GTC  CGC  TTT  GAA  GGG  ATG  GAG  CCG      12480
Lys  Val  Lys  Glu  Phe  Arg  His  Lys  Val  Arg  Phe  Glu  Gly  Met  Glu  Pro
4145                4150                     4155                4160

CTG  CCC  TCT  CGC  TCC  TCC  AGG  GGC  TCC  AAG  GTA  TCC  CCG  GAT  GTG  CCC      12528
Leu  Pro  Ser  Arg  Ser  Ser  Arg  Gly  Ser  Lys  Val  Ser  Pro  Asp  Val  Pro
               4165                4170                     4175

CCA  CCC  AGC  GCT  GGC  TCC  GAT  GCC  TCG  CAC  CCC  TCC  ACC  TCC  TCC  AGC      12576
Pro  Pro  Ser  Ala  Gly  Ser  Asp  Ala  Ser  His  Pro  Ser  Thr  Ser  Ser  Ser
               4180                4185                     4190

CAG  CTG  GAT  GGG  CTG  AGC  GTG  AGC  CTG  GGC  CGG  CTG  GGG  ACA  AGG  TGT      12624
Gln  Leu  Asp  Gly  Leu  Ser  Val  Ser  Leu  Gly  Arg  Leu  Gly  Thr  Arg  Cys
          4195                4200                     4205

GAG  CCT  GAG  CCC  TCC  CGC  CTC  CAA  GCC  GTG  TTC  GAG  GCC  CTG  CTC  ACC      12672
Glu  Pro  Glu  Pro  Ser  Arg  Leu  Gln  Ala  Val  Phe  Glu  Ala  Leu  Leu  Thr
          4210                4215                     4220

CAG  TTT  GAC  CGA  CTC  AAC  CAG  GCC  ACA  GAG  GAC  GTC  TAC  CAG  CTG  GAG      12720
Gln  Phe  Asp  Arg  Leu  Asn  Gln  Ala  Thr  Glu  Asp  Val  Tyr  Gln  Leu  Glu
4225                4230                     4235                4240

CAG  CAG  CTG  CAC  AGC  CTG  CAA  GGC  CGC  AGG  AGC  AGC  CGG  GCG  CCC  GCC      12768
Gln  Gln  Leu  His  Ser  Leu  Gln  Gly  Arg  Arg  Ser  Ser  Arg  Ala  Pro  Ala
               4245                4250                     4255

GGA  TCT  TCC  CGT  GGC  CCA  TCC  CCG  GGC  CTG  CGG  CCA  GCA  CTG  CCC  AGC      12816
Gly  Ser  Ser  Arg  Gly  Pro  Ser  Pro  Gly  Leu  Arg  Pro  Ala  Leu  Pro  Ser
          4260                4265                     4270

CGC  CTT  GCC  CGG  GCC  AGT  CGG  GGT  GTG  GAC  CTG  GCC  ACT  GGC  CCC  AGC      12864
Arg  Leu  Ala  Arg  Ala  Ser  Arg  Gly  Val  Asp  Leu  Ala  Thr  Gly  Pro  Ser
          4275                4280                     4285

AGG  ACA  CCC  CTT  CGG  GCC  AAG  AAC  AAG  GTC  CAC  CCC  AGC  AGC  ACT  TAG      12912
Arg  Thr  Pro  Leu  Arg  Ala  Lys  Asn  Lys  Val  His  Pro  Ser  Ser  Thr   *
          4290                4295                     4300
```

( 2 ) INFORMATION FOR SEQ ID NO:2:

( i ) SEQUENCE CHARACTERISTICS:
        ( A ) LENGTH: 4303 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:2:

```
Met  Pro  Pro  Ala  Ala  Pro  Ala  Arg  Leu  Ala  Leu  Ala  Leu  Gly  Leu  Gly
1                   5                   10                      15

Leu  Trp  Leu  Gly  Ala  Leu  Ala  Gly  Gly  Pro  Gly  Arg  Gly  Cys  Gly  Pro
               20                  25                      30

Cys  Glu  Pro  Pro  Cys  Leu  Cys  Gly  Pro  Ala  Pro  Gly  Ala  Ala  Cys  Arg
          35                  40                      45
```

-continued

```
Val  Asn  Cys  Ser  Gly  Arg  Gly  Leu  Arg  Thr  Leu  Gly  Pro  Ala  Leu  Arg
          50                       55                       60

Ile  Pro  Ala  Asp  Ala  Thr  Glu  Leu  Asp  Val  Ser  His  Asn  Leu  Leu  Arg
65                       70                       75                         80

Ala  Leu  Asp  Val  Gly  Leu  Leu  Ala  Asn  Leu  Ser  Ala  Leu  Ala  Glu  Leu
                         85                       90                       95

Asp  Ile  Ser  Asn  Asn  Lys  Ile  Ser  Thr  Leu  Glu  Glu  Gly  Ile  Phe  Ala
                    100                      105                      110

Asn  Leu  Phe  Asn  Leu  Ser  Glu  Ile  Asn  Leu  Ser  Gly  Asn  Pro  Phe  Glu
               115                      120                      125

Cys  Asp  Cys  Gly  Leu  Ala  Trp  Leu  Pro  Gln  Trp  Ala  Glu  Glu  Gln  Gln
          130                      135                      140

Val  Arg  Val  Val  Gln  Pro  Glu  Ala  Ala  Thr  Cys  Ala  Gly  Pro  Gly  Ser
145                      150                      155                         160

Leu  Ala  Gly  Gln  Pro  Leu  Leu  Gly  Ile  Pro  Leu  Leu  Asp  Ser  Gly  Cys
                    165                      170                      175

Gly  Glu  Glu  Tyr  Val  Ala  Cys  Leu  Pro  Asp  Asn  Ser  Ser  Gly  Thr  Val
               180                      185                      190

Ala  Ala  Val  Ser  Phe  Ser  Ala  Ala  His  Glu  Gly  Leu  Leu  Gln  Pro  Glu
               195                      200                      205

Ala  Cys  Ser  Ala  Phe  Cys  Phe  Ser  Thr  Gly  Gln  Gly  Leu  Ala  Ala  Leu
          210                      215                      220

Ser  Glu  Gln  Gly  Trp  Cys  Leu  Cys  Gly  Ala  Ala  Gln  Pro  Ser  Ser  Ala
225                      230                      235                         240

Ser  Phe  Ala  Cys  Leu  Ser  Leu  Cys  Ser  Gly  Pro  Pro  Ala  Pro  Pro  Ala
               245                      250                      255

Pro  Thr  Cys  Arg  Gly  Pro  Thr  Leu  Leu  Gln  His  Val  Phe  Pro  Ala  Ser
               260                      265                      270

Pro  Gly  Ala  Thr  Leu  Val  Gly  Pro  His  Gly  Pro  Leu  Ala  Ser  Gly  Gln
               275                      280                      285

Leu  Ala  Ala  Phe  His  Ile  Ala  Ala  Pro  Leu  Pro  Val  Thr  Asp  Thr  Arg
290                      295                      300

Trp  Asp  Phe  Gly  Asp  Gly  Ser  Ala  Glu  Val  Asp  Ala  Ala  Gly  Pro  Ala
305                      310                      315                         320

Ala  Ser  His  Arg  Tyr  Val  Leu  Pro  Gly  Arg  Tyr  His  Val  Thr  Ala  Val
               325                      330                      335

Leu  Ala  Leu  Gly  Ala  Gly  Ser  Ala  Leu  Leu  Gly  Thr  Asp  Val  Gln  Val
               340                      345                      350

Glu  Ala  Ala  Pro  Ala  Ala  Leu  Glu  Leu  Val  Cys  Pro  Ser  Ser  Val  Gln
               355                      360                      365

Ser  Asp  Glu  Ser  Leu  Asp  Leu  Ser  Ile  Gln  Asn  Arg  Gly  Gly  Ser  Gly
     370                      375                      380

Leu  Glu  Ala  Ala  Tyr  Ser  Ile  Val  Ala  Leu  Gly  Glu  Glu  Pro  Ala  Arg
385                      390                      395                         400

Ala  Val  His  Pro  Leu  Cys  Pro  Ser  Asp  Thr  Glu  Ile  Phe  Pro  Gly  Asn
               405                      410                      415

Gly  His  Cys  Tyr  Arg  Leu  Val  Val  Glu  Lys  Ala  Ala  Trp  Leu  Gln  Ala
               420                      425                      430

Gln  Glu  Gln  Cys  Gln  Ala  Trp  Ala  Gly  Ala  Ala  Leu  Ala  Met  Val  Asp
          435                      440                      445

Ser  Pro  Ala  Val  Gln  Arg  Phe  Leu  Val  Ser  Arg  Val  Thr  Arg  Ser  Leu
     450                      455                      460

Asp  Val  Trp  Ile  Gly  Phe  Ser  Thr  Val  Gln  Gly  Val  Glu  Val  Gly  Pro
```

```
465                    470                    475                    480
Ala  Pro  Gln  Gly  Glu  Ala  Phe  Ser  Leu  Glu  Ser  Cys  Gln  Asn  Trp  Leu
                         485                    490                    495
Pro  Gly  Glu  Pro  His  Pro  Ala  Thr  Ala  Glu  His  Cys  Val  Arg  Leu  Gly
               500                    505                    510
Pro  Thr  Gly  Trp  Cys  Asn  Thr  Asp  Leu  Cys  Ser  Ala  Pro  His  Ser  Tyr
               515                    520                    525
Val  Cys  Glu  Leu  Gln  Pro  Gly  Gly  Pro  Val  Gln  Asp  Ala  Glu  Asn  Leu
     530                    535                    540
Leu  Val  Gly  Ala  Pro  Ser  Gly  Asp  Leu  Gln  Gly  Pro  Leu  Thr  Pro  Leu
545                    550                    555                    560
Ala  Gln  Gln  Asp  Gly  Leu  Ser  Ala  Pro  His  Glu  Pro  Val  Glu  Val  Met
                    565                    570                    575
Val  Phe  Pro  Gly  Leu  Arg  Leu  Ser  Arg  Glu  Ala  Phe  Leu  Thr  Thr  Ala
               580                    585                    590
Glu  Phe  Gly  Thr  Gln  Glu  Leu  Arg  Arg  Pro  Ala  Gln  Leu  Arg  Leu  Gln
               595                    600                    605
Val  Tyr  Arg  Leu  Leu  Ser  Thr  Ala  Gly  Thr  Pro  Glu  Asn  Gly  Ser  Glu
          610                    615                    620
Pro  Glu  Ser  Arg  Ser  Pro  Asp  Asn  Arg  Thr  Gln  Leu  Ala  Pro  Ala  Cys
625                    630                    635                    640
Met  Pro  Gly  Gly  Arg  Trp  Cys  Pro  Gly  Ala  Asn  Ile  Cys  Leu  Pro  Leu
                    645                    650                    655
Asp  Ala  Ser  Cys  His  Pro  Gln  Ala  Cys  Ala  Asn  Gly  Cys  Thr  Ser  Gly
               660                    665                    670
Pro  Gly  Leu  Pro  Gly  Ala  Pro  Tyr  Ala  Leu  Trp  Arg  Glu  Phe  Leu  Phe
          675                    680                    685
Ser  Val  Pro  Ala  Gly  Pro  Pro  Ala  Gln  Tyr  Ser  Val  Thr  Leu  His  Gly
     690                    695                    700
Gln  Asp  Val  Leu  Met  Leu  Pro  Gly  Asp  Leu  Val  Gly  Leu  Gln  His  Asp
705                    710                    715                    720
Ala  Gly  Pro  Gly  Ala  Leu  Leu  His  Cys  Ser  Pro  Ala  Pro  Gly  His  Pro
                    725                    730                    735
Gly  Pro  Arg  Ala  Pro  Tyr  Leu  Ser  Ala  Asn  Ala  Ser  Ser  Trp  Leu  Pro
               740                    745                    750
His  Leu  Pro  Ala  Gln  Leu  Glu  Gly  Thr  Trp  Gly  Cys  Pro  Ala  Cys  Ala
          755                    760                    765
Leu  Arg  Leu  Leu  Ala  Gln  Arg  Glu  Gln  Leu  Thr  Val  Leu  Leu  Gly  Leu
     770                    775                    780
Arg  Pro  Asn  Pro  Gly  Leu  Arg  Leu  Pro  Gly  Arg  Tyr  Glu  Val  Arg  Ala
785                    790                    795                    800
Glu  Val  Gly  Asn  Gly  Val  Ser  Arg  His  Asn  Leu  Ser  Cys  Ser  Phe  Asp
                    805                    810                    815
Val  Val  Ser  Pro  Val  Ala  Gly  Leu  Arg  Val  Ile  Tyr  Pro  Ala  Pro  Arg
               820                    825                    830
Asp  Gly  Arg  Leu  Tyr  Val  Pro  Thr  Asn  Gly  Ser  Ala  Leu  Val  Leu  Gln
          835                    840                    845
Val  Asp  Ser  Gly  Ala  Asn  Ala  Thr  Ala  Thr  Ala  Arg  Trp  Pro  Gly  Gly
     850                    855                    860
Ser  Leu  Ser  Ala  Arg  Phe  Glu  Asn  Val  Cys  Pro  Ala  Leu  Val  Ala  Thr
865                    870                    875                    880
Phe  Val  Pro  Ala  Cys  Pro  Trp  Glu  Thr  Asn  Asp  Thr  Leu  Phe  Ser  Val
                    885                    890                    895
```

```
Val  Ala  Leu  Pro  Trp  Leu  Ser  Glu  Gly  Glu  His  Val  Val  Asp  Val  Val
               900                 905                 910

Val  Glu  Asn  Ser  Ala  Ser  Arg  Ala  Asn  Leu  Ser  Leu  Arg  Val  Thr  Ala
          915                 920                 925

Glu  Glu  Pro  Ile  Cys  Gly  Leu  Arg  Ala  Thr  Pro  Ser  Pro  Glu  Ala  Arg
     930                 935                 940

Val  Leu  Gln  Gly  Val  Leu  Val  Arg  Tyr  Ser  Pro  Val  Val  Glu  Ala  Gly
945                 950                 955                           960

Ser  Asp  Met  Val  Phe  Arg  Trp  Thr  Ile  Asn  Asp  Lys  Gln  Ser  Leu  Thr
               965                 970                      975

Phe  Gln  Asn  Val  Val  Phe  Asn  Val  Ile  Tyr  Gln  Ser  Ala  Ala  Val  Phe
               980                 985                      990

Lys  Leu  Ser  Leu  Thr  Ala  Ser  Asn  His  Val  Ser  Asn  Val  Thr  Val  Asn
          995                 1000                1005

Tyr  Asn  Val  Thr  Val  Glu  Arg  Met  Asn  Arg  Met  Gln  Gly  Leu  Gln  Val
     1010                1015                1020

Ser  Thr  Val  Pro  Ala  Val  Leu  Ser  Pro  Asn  Ala  Thr  Leu  Ala  Leu  Thr
1025                1030                1035                          1040

Ala  Gly  Val  Leu  Val  Asp  Ser  Ala  Val  Glu  Val  Ala  Phe  Leu  Trp  Thr
                    1045                1050                1055

Phe  Gly  Asp  Gly  Glu  Gln  Ala  Leu  His  Gln  Phe  Gln  Pro  Pro  Tyr  Asn
               1060                1065                1070

Glu  Ser  Phe  Pro  Val  Pro  Asp  Pro  Ser  Val  Ala  Gln  Val  Leu  Val  Glu
          1075                1080                     1085

His  Asn  Val  Thr  His  Thr  Tyr  Ala  Ala  Pro  Gly  Glu  Tyr  Leu  Leu  Thr
          1090                1095                1100

Val  Leu  Ala  Ser  Asn  Ala  Phe  Glu  Asn  Leu  Thr  Gln  Gln  Val  Pro  Val
1105                1110                1115                          1120

Ser  Val  Arg  Ala  Ser  Leu  Pro  Ser  Val  Ala  Val  Gly  Val  Ser  Asp  Gly
                    1125                1130                1135

Val  Leu  Val  Ala  Gly  Arg  Pro  Val  Thr  Phe  Tyr  Pro  His  Pro  Leu  Pro
                    1140                1145                1150

Ser  Pro  Gly  Gly  Val  Leu  Tyr  Thr  Trp  Asp  Phe  Gly  Asp  Gly  Ser  Pro
          1155                1160                1165

Val  Leu  Thr  Gln  Ser  Gln  Pro  Ala  Ala  Asn  His  Thr  Tyr  Ala  Ser  Arg
     1170                1175                1180

Gly  Thr  Tyr  His  Val  Arg  Leu  Glu  Val  Asn  Asn  Thr  Val  Ser  Gly  Ala
1185                1190                1195                          1200

Ala  Ala  Gln  Ala  Asp  Val  Arg  Val  Phe  Glu  Glu  Leu  Arg  Gly  Leu  Ser
               1205                1210                     1215

Val  Asp  Met  Ser  Leu  Ala  Val  Glu  Gln  Gly  Ala  Pro  Val  Val  Val  Ser
               1220                1225                1230

Ala  Ala  Val  Gln  Thr  Gly  Asp  Asn  Ile  Thr  Trp  Thr  Phe  Asp  Met  Gly
          1235                1240                1245

Asp  Gly  Thr  Val  Leu  Ser  Gly  Pro  Glu  Ala  Thr  Val  Glu  His  Val  Tyr
     1250                1255                1260

Leu  Arg  Ala  Gln  Asn  Cys  Thr  Val  Thr  Val  Gly  Ala  Gly  Ser  Pro  Ala
1265                1270                1275                          1280

Gly  His  Leu  Ala  Arg  Ser  Leu  His  Val  Leu  Val  Phe  Val  Leu  Glu  Val
                    1285                1290                1295

Leu  Arg  Val  Glu  Pro  Ala  Ala  Cys  Ile  Pro  Thr  Gln  Pro  Asp  Ala  Arg
                    1300                1305                1310

Leu  Thr  Ala  Tyr  Val  Thr  Gly  Asn  Pro  Ala  His  Tyr  Leu  Phe  Asp  Trp
               1315                1320                1325
```

```
Thr  Phe  Gly  Asp  Gly  Ser  Ser  Asn  Thr  Thr  Val  Arg  Gly  Cys  Pro  Thr
     1330                1335                1340
Val  Thr  His  Asn  Phe  Thr  Arg  Ser  Gly  Thr  Phe  Pro  Leu  Ala  Leu  Val
1345                1350                1355                          1360
Leu  Ser  Ser  Arg  Val  Asn  Arg  Ala  His  Tyr  Phe  Thr  Ser  Ile  Cys  Val
               1365                1370                          1375
Glu  Pro  Glu  Val  Gly  Asn  Val  Thr  Leu  Gln  Pro  Glu  Arg  Gln  Phe  Val
          1380                1385                          1390
Gln  Leu  Gly  Asp  Glu  Ala  Trp  Leu  Val  Ala  Cys  Ala  Trp  Pro  Pro  Phe
               1395                1400                1405
Pro  Tyr  Arg  Tyr  Thr  Trp  Asp  Phe  Gly  Thr  Glu  Glu  Ala  Ala  Pro  Thr
          1410                1415                1420
Arg  Ala  Arg  Gly  Pro  Glu  Val  Thr  Phe  Ile  Tyr  Arg  Asp  Pro  Gly  Ser
1425                1430                1435                          1440
Tyr  Leu  Val  Thr  Val  Thr  Ala  Ser  Asn  Asn  Ile  Ser  Ala  Ala  Asn  Asp
               1445                1450                          1455
Ser  Ala  Leu  Val  Glu  Val  Gln  Glu  Pro  Val  Leu  Val  Thr  Ser  Ile  Lys
               1460                1465                          1470
Val  Asn  Gly  Ser  Leu  Gly  Leu  Glu  Leu  Gln  Gln  Pro  Tyr  Leu  Phe  Ser
          1475                1480                          1485
Ala  Val  Gly  Arg  Gly  Arg  Pro  Ala  Ser  Tyr  Leu  Trp  Asp  Leu  Gly  Asp
     1490                1495                          1500
Gly  Gly  Trp  Leu  Glu  Gly  Pro  Glu  Val  Thr  His  Ala  Tyr  Asn  Ser  Thr
1505                1510                1515                          1520
Gly  Asp  Phe  Thr  Val  Arg  Val  Ala  Gly  Trp  Asn  Glu  Val  Ser  Arg  Ser
               1525                1530                          1535
Glu  Ala  Trp  Leu  Asn  Val  Thr  Val  Lys  Arg  Arg  Val  Arg  Gly  Leu  Val
               1540                1545                          1550
Val  Asn  Ala  Ser  Arg  Thr  Val  Val  Pro  Leu  Asn  Gly  Ser  Val  Ser  Phe
          1555                1560                          1565
Ser  Thr  Ser  Leu  Glu  Ala  Gly  Ser  Asp  Val  Arg  Tyr  Ser  Trp  Val  Leu
          1570                1575                          1580
Cys  Asp  Arg  Cys  Thr  Pro  Ile  Pro  Gly  Gly  Pro  Thr  Ile  Ser  Tyr  Thr
1585                1590                1595                          1600
Phe  Arg  Ser  Val  Gly  Thr  Phe  Asn  Ile  Ile  Val  Thr  Ala  Glu  Asn  Glu
                    1605                1610                     1615
Val  Gly  Ser  Ala  Gln  Asp  Ser  Ile  Phe  Val  Tyr  Val  Leu  Gln  Leu  Ile
               1620                1625                          1630
Glu  Gly  Leu  Gln  Val  Val  Gly  Gly  Gly  Arg  Tyr  Phe  Pro  Thr  Asn  His
               1635                1640                          1645
Thr  Val  Gln  Leu  Gln  Ala  Val  Val  Arg  Asp  Gly  Thr  Asn  Val  Ser  Tyr
1650                1655                          1660
Ser  Trp  Thr  Ala  Trp  Arg  Asp  Arg  Gly  Pro  Ala  Leu  Ala  Gly  Ser  Gly
1665                1670                1675                          1680
Lys  Gly  Phe  Ser  Leu  Thr  Val  Leu  Glu  Ala  Gly  Thr  Tyr  His  Val  Gln
               1685                1690                          1695
Leu  Arg  Ala  Thr  Asn  Met  Leu  Gly  Ser  Ala  Trp  Ala  Asp  Cys  Thr  Met
               1700                1705                          1710
Asp  Phe  Val  Glu  Pro  Val  Gly  Trp  Leu  Met  Val  Ala  Ala  Ser  Pro  Asn
          1715                1720                          1725
Pro  Ala  Ala  Val  Asn  Thr  Ser  Val  Thr  Leu  Ser  Ala  Glu  Leu  Ala  Gly
          1730                1735                          1740
Gly  Ser  Gly  Val  Val  Tyr  Thr  Trp  Ser  Leu  Glu  Glu  Gly  Leu  Ser  Trp
```

```
          1745                1750                1755                1760
Glu  Thr  Ser  Glu  Pro  Phe  Thr  Thr  His  Ser  Phe  Pro  Thr  Pro  Gly  Leu
                    1765                1770                1775

His  Leu  Val  Thr  Met  Thr  Ala  Gly  Asn  Pro  Leu  Gly  Ser  Ala  Asn  Ala
                    1780                1785                1790

Thr  Val  Glu  Val  Asp  Val  Gln  Val  Pro  Val  Ser  Gly  Leu  Ser  Ile  Arg
                    1795                1800                1805

Ala  Ser  Glu  Pro  Gly  Gly  Ser  Phe  Val  Ala  Ala  Gly  Ser  Ser  Val  Pro
          1810                1815                1820

Phe  Trp  Gly  Gln  Leu  Ala  Thr  Gly  Thr  Asn  Val  Ser  Trp  Cys  Trp  Ala
1825                1830                1835                1840

Val  Pro  Gly  Gly  Ser  Ser  Lys  Arg  Gly  Pro  His  Val  Thr  Met  Val  Phe
               1845                1850                1855

Pro  Asp  Ala  Gly  Thr  Phe  Ser  Ile  Arg  Leu  Asn  Ala  Ser  Asn  Ala  Val
               1860                1865                1870

Ser  Trp  Val  Ser  Ala  Thr  Tyr  Asn  Leu  Thr  Ala  Glu  Glu  Pro  Ile  Val
               1875                1880                1885

Gly  Leu  Val  Leu  Trp  Ala  Ser  Ser  Lys  Val  Val  Ala  Pro  Gly  Gln  Leu
          1890                1895                1900

Val  His  Phe  Gln  Ile  Leu  Leu  Ala  Ala  Gly  Ser  Ala  Val  Thr  Phe  Arg
1905                1910                1915                1920

Leu  Gln  Val  Gly  Gly  Ala  Asn  Pro  Glu  Val  Leu  Pro  Gly  Pro  Arg  Phe
                    1925                1930                1935

Ser  His  Ser  Phe  Pro  Arg  Val  Gly  Asp  His  Val  Val  Ser  Val  Arg  Gly
               1940                1945                1950

Lys  Asn  His  Val  Ser  Trp  Ala  Gln  Ala  Gln  Val  Arg  Ile  Val  Val  Leu
          1955                1960                1965

Glu  Ala  Val  Ser  Gly  Leu  Gln  Val  Pro  Asn  Cys  Cys  Glu  Pro  Gly  Ile
     1970                1975                1980

Ala  Thr  Gly  Thr  Glu  Arg  Asn  Phe  Thr  Ala  Arg  Val  Gln  Arg  Gly  Ser
1985                1990                1995                2000

Arg  Val  Ala  Tyr  Ala  Trp  Tyr  Phe  Ser  Leu  Gln  Lys  Val  Gln  Gly  Asp
               2005                2010                2015

Ser  Leu  Val  Ile  Leu  Ser  Gly  Arg  Asp  Val  Thr  Tyr  Thr  Pro  Val  Ala
               2020                2025                2030

Ala  Gly  Leu  Leu  Glu  Ile  Gln  Val  Arg  Ala  Phe  Asn  Ala  Leu  Gly  Ser
               2035                2040                2045

Glu  Asn  Arg  Thr  Leu  Val  Leu  Glu  Val  Gln  Asp  Ala  Val  Gln  Tyr  Val
          2050                2055                2060

Ala  Leu  Gln  Ser  Gly  Pro  Cys  Phe  Thr  Asn  Arg  Ser  Ala  Gln  Phe  Glu
2065                2070                2075                2080

Ala  Ala  Thr  Ser  Pro  Ser  Pro  Arg  Arg  Val  Ala  Tyr  His  Trp  Asp  Phe
                    2085                2090                2095

Gly  Asp  Gly  Ser  Pro  Gly  Gln  Asp  Thr  Asp  Glu  Pro  Arg  Ala  Glu  His
               2100                2105                2110

Ser  Tyr  Leu  Arg  Pro  Gly  Asp  Tyr  Arg  Val  Gln  Val  Asn  Ala  Ser  Asn
               2115                2120                2125

Leu  Val  Ser  Phe  Phe  Val  Ala  Gln  Ala  Thr  Val  Thr  Val  Gln  Val  Leu
     2130                2135                2140

Ala  Cys  Arg  Glu  Pro  Glu  Val  Asp  Val  Val  Leu  Pro  Leu  Gln  Val  Leu
2145                2150                2155                2160

Met  Arg  Arg  Ser  Gln  Arg  Asn  Tyr  Leu  Glu  Ala  His  Val  Asp  Leu  Arg
                    2165                2170                2175
```

```
Asp Cys Val Thr Tyr Gln Thr Glu Tyr Arg Trp Glu Val Tyr Arg Thr
                2180                2185                2190
Ala Ser Cys Gln Arg Pro Gly Arg Pro Ala Arg Val Ala Leu Pro Gly
                2195                2200                2205
Val Asp Val Ser Arg Pro Arg Leu Val Leu Pro Arg Leu Ala Leu Pro
2210                2215                2220
Val Gly His Tyr Cys Phe Val Phe Val Val Ser Phe Gly Asp Thr Pro
2225                2230                2235                2240
Leu Thr Gln Ser Ile Gln Ala Asn Val Thr Val Ala Pro Glu Arg Leu
                2245                2250                2255
Val Pro Ile Ile Glu Gly Gly Ser Tyr Arg Val Trp Ser Asp Thr Arg
                2260                2265                2270
Asp Leu Val Leu Asp Gly Ser Glu Ser Tyr Asp Pro Asn Leu Glu Asp
                2275                2280                2285
Gly Asp Gln Thr Pro Leu Ser Phe His Trp Ala Cys Val Ala Ser Thr
                2290                2295                2300
Gln Arg Glu Ala Gly Gly Cys Ala Leu Asn Phe Gly Pro Arg Gly Ser
2305                2310                2315                2320
Ser Thr Val Thr Ile Pro Arg Glu Arg Leu Ala Ala Gly Val Glu Tyr
                2325                2330                2335
Thr Phe Ser Leu Thr Val Trp Lys Ala Gly Arg Lys Glu Ala Thr
                2340                2345                2350
Asn Gln Thr Val Leu Ile Arg Ser Gly Arg Val Pro Ile Val Ser Leu
                2355                2360                2365
Glu Cys Val Ser Cys Lys Ala Gln Ala Val Tyr Glu Val Ser Arg Ser
                2370                2375                2380
Ser Tyr Val Tyr Leu Glu Gly Arg Cys Leu Asn Cys Ser Ser Gly Ser
2385                2390                2395                2400
Lys Arg Gly Arg Trp Ala Ala Arg Thr Phe Ser Asn Lys Thr Leu Val
                2405                2410                2415
Leu Asp Glu Thr Thr Thr Ser Thr Gly Ser Ala Gly Met Arg Leu Val
                2420                2425                2430
Leu Arg Arg Gly Val Leu Arg Asp Gly Glu Gly Tyr Thr Phe Thr Leu
                2435                2440                2445
Thr Val Leu Gly Arg Ser Gly Glu Glu Glu Gly Cys Ala Ser Ile Arg
                2450                2455                2460
Leu Ser Pro Asn Arg Pro Pro Leu Gly Gly Ser Cys Arg Leu Phe Pro
2465                2470                2475                2480
Leu Gly Ala Val His Ala Leu Thr Thr Lys Val His Phe Glu Cys Thr
                2485                2490                2495
Gly Trp His Asp Ala Glu Asp Ala Gly Ala Pro Leu Val Tyr Ala Leu
                2500                2505                2510
Leu Leu Arg Arg Cys Arg Gln Gly His Cys Glu Glu Phe Cys Val Tyr
                2515                2520                2525
Lys Gly Ser Leu Ser Ser Tyr Gly Ala Val Leu Pro Pro Gly Phe Arg
                2530                2535                2540
Pro His Phe Glu Val Gly Leu Ala Val Val Val Gln Asp Gln Leu Gly
2545                2550                2555                2560
Ala Ala Val Val Ala Leu Asn Arg Ser Leu Ala Ile Thr Leu Pro Glu
                2565                2570                2575
Pro Asn Gly Ser Ala Thr Gly Leu Thr Val Trp Leu His Gly Leu Thr
                2580                2585                2590
Ala Ser Val Leu Pro Gly Leu Leu Arg Gln Ala Asp Pro Gln His Val
                2595                2600                2605
```

```
Ile Glu Tyr Ser Leu Ala Leu Val Thr Val Leu Asn Glu Tyr Glu Arg
    2610                2615                2620

Ala Leu Asp Val Ala Ala Glu Pro Lys His Glu Arg Gln His Arg Ala
2625                2630                2635                2640

Gln Ile Arg Lys Asn Ile Thr Glu Thr Leu Val Ser Leu Arg Val His
                2645                2650                2655

Thr Val Asp Asp Ile Gln Gln Ile Ala Ala Ala Leu Ala Gln Cys Met
            2660                2665                2670

Gly Pro Ser Arg Glu Leu Val Cys Arg Ser Cys Leu Lys Gln Thr Leu
            2675                2680                2685

His Lys Leu Glu Ala Met Met Leu Ile Leu Gln Ala Glu Thr Thr Ala
            2690                2695                2700

Gly Thr Val Thr Pro Thr Ala Ile Gly Asp Ser Ile Leu Asn Ile Thr
2705                2710                2715                2720

Gly Asp Leu Ile His Leu Ala Ser Ser Asp Val Arg Ala Pro Gln Pro
                2725                2730                2735

Ser Glu Leu Gly Ala Glu Ser Pro Ser Arg Met Val Ala Ser Gln Ala
            2740                2745                2750

Tyr Asn Leu Thr Ser Ala Leu Met Arg Ile Leu Met Arg Ser Arg Val
            2755                2760                2765

Leu Asn Glu Glu Pro Leu Thr Leu Ala Gly Glu Glu Ile Val Ala Gln
    2770                2775                2780

Gly Lys Arg Ser Asp Pro Arg Ser Leu Leu Cys Tyr Gly Gly Ala Pro
2785                2790                2795                2800

Gly Pro Gly Cys His Phe Ser Ile Pro Glu Ala Phe Ser Gly Ala Leu
                2805                2810                2815

Ala Asn Leu Ser Asp Val Val Gln Leu Ile Phe Leu Val Asp Ser Asn
            2820                2825                2830

Pro Phe Pro Phe Gly Tyr Ile Ser Asn Tyr Thr Val Ser Thr Lys Val
            2835                2840                2845

Ala Ser Met Ala Phe Gln Thr Gln Ala Gly Ala Gln Ile Pro Ile Glu
    2850                2855                2860

Arg Leu Ala Ser Glu Arg Ala Ile Thr Val Lys Val Pro Asn Asn Ser
2865                2870                2875                2880

Asp Trp Ala Ala Arg Gly His Arg Ser Ser Ala Asn Ser Ala Asn Ser
                2885                2890                2895

Val Val Val Gln Pro Gln Ala Ser Val Gly Ala Val Val Thr Leu Asp
            2900                2905                2910

Ser Ser Asn Pro Ala Ala Gly Leu His Leu Gln Leu Asn Tyr Thr Leu
            2915                2920                2925

Leu Asp Gly His Tyr Leu Ser Glu Glu Pro Glu Pro Tyr Leu Ala Val
    2930                2935                2940

Tyr Leu His Ser Glu Pro Arg Pro Asn Glu His Asn Cys Ser Ala Ser
2945                2950                2955                2960

Arg Arg Ile Arg Pro Glu Ser Leu Gln Gly Ala Asp His Arg Pro Tyr
                2965                2970                2975

Thr Phe Phe Ile Ser Pro Gly Ser Arg Asp Pro Ala Gly Ser Tyr His
            2980                2985                2990

Leu Asn Leu Ser Ser His Phe Arg Trp Ser Ala Leu Gln Val Ser Val
    2995                3000                3005

Gly Leu Tyr Thr Ser Leu Cys Gln Tyr Phe Ser Glu Glu Asp Met Val
    3010                3015                3020

Trp Arg Thr Glu Gly Leu Leu Pro Leu Glu Glu Thr Ser Pro Arg Gln
```

```
                3025                    3030                    3035                    3040
Ala  Val  Cys  Leu  Thr  Arg  His  Leu  Thr  Ala  Phe  Gly  Ala  Ser  Leu  Phe
                         3045                    3050                    3055
Val  Pro  Pro  Ser  His  Val  Arg  Phe  Val  Phe  Pro  Glu  Pro  Thr  Ala  Asp
     3060                         3065                    3070
Val  Asn  Tyr  Ile  Val  Met  Leu  Thr  Cys  Ala  Val  Cys  Leu  Val  Thr  Tyr
          3075                    3080                    3085
Met  Val  Met  Ala  Ala  Ile  Leu  His  Lys  Leu  Asp  Gln  Leu  Asp  Ala  Ser
3090                         3095                    3100
Arg  Gly  Arg  Ala  Ile  Pro  Phe  Cys  Gly  Gln  Arg  Gly  Arg  Phe  Lys  Tyr
3105                    3110                    3115                         3120
Glu  Ile  Leu  Val  Lys  Thr  Gly  Trp  Gly  Arg  Gly  Ser  Gly  Thr  Thr  Ala
                    3125                    3130                    3135
His  Val  Gly  Ile  Met  Leu  Tyr  Gly  Val  Asp  Ser  Arg  Ser  Gly  His  Arg
               3140                    3145                    3150
His  Leu  Asp  Gly  Asp  Arg  Ala  Phe  His  Arg  Asn  Ser  Leu  Asp  Ile  Phe
          3155                    3160                    3165
Arg  Ile  Ala  Thr  Pro  His  Ser  Leu  Gly  Ser  Val  Trp  Lys  Ile  Arg  Val
               3170                    3175                    3180
Trp  His  Asp  Asn  Lys  Gly  Leu  Ser  Pro  Ala  Trp  Phe  Leu  Gln  His  Val
3185                    3190                    3195                         3200
Ile  Val  Arg  Asp  Leu  Gln  Thr  Ala  Arg  Ser  Ala  Phe  Phe  Leu  Val  Asn
               3205                    3210                    3215
Asp  Trp  Leu  Ser  Val  Glu  Thr  Glu  Ala  Asn  Gly  Gly  Leu  Val  Glu  Lys
               3220                    3225                    3230
Glu  Val  Leu  Ala  Ala  Ser  Asp  Ala  Ala  Leu  Leu  Arg  Phe  Arg  Arg  Leu
          3235                    3240                    3245
Leu  Val  Ala  Glu  Leu  Gln  Arg  Gly  Phe  Phe  Asp  Lys  His  Ile  Trp  Leu
     3250                    3255                    3260
Ser  Ile  Trp  Asp  Arg  Pro  Pro  Arg  Ser  Arg  Phe  Thr  Arg  Ile  Gln  Arg
3265                    3270                    3275                         3280
Ala  Thr  Cys  Cys  Val  Leu  Leu  Ile  Cys  Leu  Phe  Leu  Gly  Ala  Asn  Ala
                    3285                    3290                    3295
Val  Trp  Tyr  Gly  Ala  Val  Gly  Asp  Ser  Ala  Tyr  Ser  Thr  Gly  His  Val
               3300                    3305                    3310
Ser  Arg  Leu  Ser  Pro  Leu  Ser  Val  Asp  Thr  Val  Ala  Val  Gly  Leu  Val
          3315                    3320                    3325
Ser  Ser  Val  Val  Val  Tyr  Pro  Val  Tyr  Leu  Ala  Ile  Leu  Phe  Leu  Phe
     3330                    3335                    3340
Arg  Met  Ser  Arg  Ser  Lys  Val  Ala  Gly  Ser  Pro  Ser  Pro  Thr  Pro  Ala
3345                    3350                    3355                         3360
Gly  Gln  Gln  Val  Leu  Asp  Ile  Asp  Ser  Cys  Leu  Asp  Ser  Ser  Val  Leu
                    3365                    3370                    3375
Asp  Ser  Ser  Phe  Leu  Thr  Phe  Ser  Gly  Leu  His  Ala  Glu  Gln  Ala  Phe
               3380                    3385                    3390
Val  Gly  Gln  Met  Lys  Ser  Asp  Leu  Phe  Leu  Asp  Asp  Ser  Lys  Ser  Leu
          3395                    3400                    3405
Val  Cys  Trp  Pro  Ser  Gly  Glu  Gly  Thr  Leu  Ser  Trp  Pro  Asp  Leu  Leu
     3410                    3415                    3420
Ser  Asp  Pro  Ser  Ile  Val  Gly  Ser  Asn  Leu  Arg  Gln  Leu  Ala  Arg  Gly
3425                    3430                    3435                         3440
Gln  Ala  Gly  His  Gly  Leu  Gly  Pro  Glu  Glu  Asp  Gly  Phe  Ser  Leu  Ala
                    3445                    3450                    3455
```

```
Ser  Pro  Tyr  Ser  Pro  Ala  Lys  Ser  Phe  Ser  Ala  Ser  Asp  Glu  Asp  Leu
              3460                 3465                3470

Ile  Gln  Gln  Val  Leu  Ala  Glu  Gly  Val  Ser  Ser  Pro  Ala  Pro  Thr  Gln
              3475                 3480                3485

Asp  Thr  His  Met  Glu  Thr  Asp  Leu  Leu  Ser  Ser  Ser  Ser  Thr  Pro
         3490                3495                     3500

Gly  Glu  Lys  Thr  Glu  Thr  Leu  Ala  Leu  Gln  Arg  Leu  Gly  Glu  Leu  Gly
3505                3510                     3515                          3520

Pro  Pro  Ser  Pro  Gly  Leu  Asn  Trp  Glu  Gln  Pro  Gln  Ala  Ala  Arg  Leu
              3525                 3530                3535

Ser  Arg  Thr  Gly  Leu  Val  Glu  Gly  Leu  Arg  Lys  Arg  Leu  Leu  Pro  Ala
              3540                 3545                3550

Trp  Cys  Ala  Ser  Leu  Ala  His  Gly  Leu  Ser  Leu  Leu  Leu  Val  Ala  Val
              3555                 3560                3565

Ala  Val  Ala  Val  Ser  Gly  Trp  Val  Gly  Ala  Ser  Phe  Pro  Pro  Gly  Val
              3570                 3575                3580

Ser  Val  Ala  Trp  Leu  Leu  Ser  Ser  Ser  Ala  Ser  Phe  Leu  Ala  Ser  Phe
3585                3590                     3595                          3600

Leu  Gly  Trp  Glu  Pro  Leu  Lys  Val  Leu  Leu  Glu  Ala  Leu  Tyr  Phe  Ser
                   3605                3610                     3615

Leu  Val  Ala  Lys  Arg  Leu  His  Pro  Asp  Glu  Asp  Thr  Leu  Val  Glu
              3620                 3625                3630

Ser  Pro  Ala  Val  Thr  Pro  Val  Ser  Ala  Arg  Val  Pro  Arg  Val  Arg  Pro
              3635                 3640                3645

Pro  His  Gly  Phe  Ala  Leu  Phe  Leu  Ala  Lys  Glu  Glu  Ala  Arg  Lys  Val
              3650                 3655                3660

Lys  Arg  Leu  His  Gly  Met  Leu  Arg  Ser  Leu  Leu  Val  Tyr  Met  Leu  Phe
3665                3670                     3675                          3680

Leu  Leu  Val  Thr  Leu  Leu  Ala  Ser  Tyr  Gly  Asp  Ala  Ser  Cys  His  Gly
              3685                 3690                3695

His  Ala  Tyr  Arg  Leu  Gln  Ser  Ala  Ile  Lys  Gln  Glu  Leu  His  Ser  Arg
              3700                 3705                3710

Ala  Phe  Leu  Ala  Ile  Thr  Arg  Ser  Glu  Glu  Leu  Trp  Pro  Trp  Met  Ala
              3715                 3720                3725

His  Val  Leu  Leu  Pro  Tyr  Val  His  Gly  Asn  Gln  Ser  Ser  Pro  Glu  Leu
3730                3735                     3740

Gly  Pro  Pro  Arg  Leu  Arg  Gln  Val  Arg  Leu  Gln  Glu  Ala  Leu  Tyr  Pro
3745                3750                     3755                          3760

Asp  Pro  Pro  Gly  Pro  Arg  Val  His  Thr  Cys  Ser  Ala  Ala  Gly  Gly  Phe
                   3765                3770                     3775

Ser  Thr  Ser  Asp  Tyr  Asp  Val  Gly  Trp  Glu  Ser  Pro  His  Asn  Gly  Ser
              3780                 3785                3790

Gly  Thr  Trp  Ala  Tyr  Ser  Ala  Pro  Asp  Leu  Leu  Gly  Ala  Trp  Ser  Trp
              3795                 3800                3805

Gly  Ser  Cys  Ala  Val  Tyr  Asp  Ser  Gly  Gly  Tyr  Val  Gln  Glu  Leu  Gly
              3810                 3815                3820

Leu  Ser  Leu  Glu  Glu  Ser  Arg  Asp  Arg  Leu  Arg  Phe  Leu  Gln  Leu  His
3825                3830                     3835                          3840

Asn  Trp  Leu  Asp  Asn  Arg  Ser  Arg  Ala  Val  Phe  Leu  Glu  Leu  Thr  Arg
                   3845                3850                     3855

Tyr  Ser  Pro  Ala  Val  Gly  Leu  His  Ala  Ala  Val  Thr  Leu  Arg  Leu  Glu
              3860                 3865                3870

Phe  Pro  Ala  Ala  Gly  Arg  Ala  Leu  Ala  Ala  Leu  Ser  Val  Arg  Pro  Phe
              3875                 3880                3885
```

```
Ala  Leu  Arg  Arg  Leu  Ser  Ala  Gly  Leu  Ser  Leu  Pro  Leu  Leu  Thr  Ser
     3890                3895                3900

Val  Cys  Leu  Leu  Leu  Phe  Ala  Val  His  Phe  Ala  Val  Ala  Glu  Ala  Arg
3905                3910                3915                          3920

Thr  Trp  His  Arg  Glu  Gly  Arg  Trp  Arg  Val  Leu  Arg  Leu  Gly  Ala  Trp
               3925                3930                          3935

Ala  Arg  Trp  Leu  Val  Ala  Leu  Thr  Ala  Ala  Thr  Ala  Leu  Val  Arg
          3940                3945                          3950

Leu  Ala  Gln  Leu  Gly  Ala  Ala  Asp  Arg  Gln  Trp  Thr  Arg  Phe  Val  Arg
          3955                3960                     3965

Gly  Arg  Pro  Arg  Arg  Phe  Thr  Ser  Phe  Asp  Gln  Val  Ala  His  Val  Ser
          3970                3975                3980

Ser  Ala  Ala  Arg  Gly  Leu  Ala  Ala  Ser  Leu  Leu  Phe  Leu  Leu  Leu  Val
3985                3990                     3995                          4000

Lys  Ala  Ala  Gln  His  Val  Arg  Phe  Val  Arg  Gln  Trp  Ser  Val  Phe  Gly
               4005                4010                     4015

Lys  Thr  Leu  Cys  Arg  Ala  Leu  Pro  Glu  Leu  Leu  Gly  Val  Thr  Leu  Gly
               4020                4025                     4030

Leu  Val  Val  Leu  Gly  Val  Ala  Tyr  Ala  Gln  Leu  Ala  Ile  Leu  Leu  Val
               4035                4040                     4045

Ser  Ser  Cys  Val  Asp  Ser  Leu  Trp  Ser  Val  Ala  Gln  Ala  Leu  Leu  Val
     4050                4055                     4060

Leu  Cys  Pro  Gly  Thr  Gly  Leu  Ser  Thr  Leu  Cys  Pro  Ala  Glu  Ser  Trp
4065                4070                4075                          4080

His  Leu  Ser  Pro  Leu  Leu  Cys  Val  Gly  Leu  Trp  Ala  Leu  Arg  Leu  Trp
               4085                4090                     4095

Gly  Ala  Leu  Arg  Leu  Gly  Ala  Val  Ile  Leu  Arg  Trp  Arg  Tyr  His  Ala
               4100                4105                     4110

Leu  Arg  Gly  Glu  Leu  Tyr  Arg  Pro  Ala  Trp  Glu  Pro  Gln  Asp  Tyr  Glu
          4115                4120                     4125

Met  Val  Glu  Leu  Phe  Leu  Arg  Arg  Leu  Arg  Leu  Trp  Met  Gly  Leu  Ser
     4130                4135                     4140

Lys  Val  Lys  Glu  Phe  Arg  His  Lys  Val  Arg  Phe  Glu  Gly  Met  Glu  Pro
4145                4150                4155                          4160

Leu  Pro  Ser  Arg  Ser  Ser  Arg  Gly  Ser  Lys  Val  Ser  Pro  Asp  Val  Pro
               4165                4170                     4175

Pro  Pro  Ser  Ala  Gly  Ser  Asp  Ala  Ser  His  Pro  Ser  Thr  Ser  Ser  Ser
               4180                4185                     4190

Gln  Leu  Asp  Gly  Leu  Ser  Val  Ser  Leu  Gly  Arg  Leu  Gly  Thr  Arg  Cys
          4195                4200                     4205

Glu  Pro  Glu  Pro  Ser  Arg  Leu  Gln  Ala  Val  Phe  Glu  Ala  Leu  Leu  Thr
4210                     4215                     4220

Gln  Phe  Asp  Arg  Leu  Asn  Gln  Ala  Thr  Glu  Asp  Val  Tyr  Gln  Leu  Glu
4225                4230                4235                          4240

Gln  Gln  Leu  His  Ser  Leu  Gln  Gly  Arg  Arg  Ser  Ser  Arg  Ala  Pro  Ala
               4245                4250                          4255

Gly  Ser  Ser  Arg  Gly  Pro  Ser  Pro  Gly  Leu  Arg  Pro  Ala  Leu  Pro  Ser
               4260                4265                     4270

Arg  Leu  Ala  Arg  Ala  Ser  Arg  Gly  Val  Asp  Leu  Ala  Thr  Gly  Pro  Ser
          4275                4280                     4285

Arg  Thr  Pro  Leu  Arg  Ala  Lys  Asn  Lys  Val  His  Pro  Ser  Ser  Thr
          4290                4295                4300
```

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CTGCCGGCCT GGTGTCG                           17

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

AGGGTCCACA CGGGCTCGG                       19

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

CAGGGTGTCC GTGCGTGACT G                   21

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

GTCCAGCACT CCTGGGGAGA                    20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

ACGCAAGGAC AAGGGAGTAG                    20

( 2 ) INFORMATION FOR SEQ ID NO:8:

( i ) SEQUENCE CHARACTERISTICS:
        ( A ) LENGTH: 19 base pairs
        ( B ) TYPE: nucleic acid (C) STRANDEDNESS: single
(D) TOPOLOGY: linear (ii) MOLECULE TYPE: DNA (xi) SEQUENCE DESCRIPTION: SEQ ID NO:8:

AGTGCCGCGG CCTCCTGAC 19

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:9:

GCTGGCCTAG GCGGCTTCCA 20

(2) INFORMATION FOR SEQ ID NO:10:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:10:

CACCCCACGG CTTTGCACT 19

(2) INFORMATION FOR SEQ ID NO:11:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:11:

CCCAGGCAGC GAGGCTGTC 19

(2) INFORMATION FOR SEQ ID NO:12:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:12:

ACACCAGGCC AACAGCGACT G 21

(2) INFORMATION FOR SEQ ID NO:13:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA ( x i ) SEQUENCE DESCRIPTION: SEQ ID NO:13:

ACAGCCACCA GGAGCAGGCT GA     22

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

TGTAGCGCGT GAGCTCCAG     19

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

CACCCCACCC TACCCCAG     18

( 2 ) INFORMATION FOR SEQ ID NO:16:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

GGAGGCCACA GGTGAGGCT     19

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

CGGAGGAGTG AGGTGGGCTC C     21

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

AGCCATTGTG AGGACTCTCC C     21

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

AAGACCTGAT CCAGCAGGTC C      21

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

CAGCACGTCA TCGTCAGG      18

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

CTCCCAGCCA CCTTGCTC      18

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

GCAGCTGTCG ATGTCCAG      18

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

TCTGTCCAAC AAAGGCCTG      19

(2) INFORMATION FOR SEQ ID NO:24:

(i) SEQUENCE CHARACTERISTICS:
        (A) LENGTH: 21 base pairs
        (B) TYPE: nucleic acid ( C ) STRANDEDNESS: single
            ( D ) TOPOLOGY: linear ( i i ) MOLECULE TYPE: DNA ( x i ) SEQUENCE DESCRIPTION: SEQ ID NO:24:

TCTTCTCCAA CTTCACGGCT G 21

( 2 ) INFORMATION FOR SEQ ID NO:25:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:25:

AACCAGCCAG GTTTTGGTCC T 21

( 2 ) INFORMATION FOR SEQ ID NO:26:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:26:

CAAGTCCAGC TCCTCTCCC 19

( 2 ) INFORMATION FOR SEQ ID NO:27:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:27:

GCTCTTTAAG GCGTCCCTC 19

( 2 ) INFORMATION FOR SEQ ID NO:28:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:28:

GCGCTTTGCA GACGGTAGGC G 21

( 2 ) INFORMATION FOR SEQ ID NO:29:

( i ) SEQUENCE CHARACTERISTICS:
            ( A ) LENGTH: 28 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:29:

TTATCAATAC TCTGGCTGAC CATCGTCA                28

( 2 ) INFORMATION FOR SEQ ID NO:30:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

TCGGGGCAGC CTCTTCCTG                19

( 2 ) INFORMATION FOR SEQ ID NO:31:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

TACAGGGAGG GGCTAGGG                18

( 2 ) INFORMATION FOR SEQ ID NO:32:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

TGCAACTGCC TCCTGGAGG                19

( 2 ) INFORMATION FOR SEQ ID NO:33:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

GGTCTGTCTC TGCTTCCC                18

( 2 ) INFORMATION FOR SEQ ID NO:34:

( i ) SEQUENCE CHARACTERISTICS:
        ( A ) LENGTH: 10 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:34:

CTAACGATGC                10

(2) INFORMATION FOR SEQ ID NO:35:

(i) SEQUENCE CHARACTERISTICS:
        (A) LENGTH: 6 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:35:

Trp Asp Phe Gly Asp Gly
    1               5